US008226950B2

(12) United States Patent
Lobb et al.

(10) Patent No.: US 8,226,950 B2
(45) Date of Patent: *Jul. 24, 2012

(54) RECOMBINANT ANTI-VLA4 ANTIBODY MOLECULES

(75) Inventors: Roy R. Lobb, Westwood, MA (US); Frank J. Carr, Aberdeenshire (GB); Philip R. Tempest, Aberdeen (GB)

(73) Assignee: Biogen Idec MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/891,284

(22) Filed: Sep. 27, 2010

(65) Prior Publication Data

US 2012/0022236 A1 Jan. 26, 2012

Related U.S. Application Data

(63) Continuation of application No. 12/338,570, filed on Dec. 18, 2008, now Pat. No. 7,829,092, which is a continuation of application No. 11/606,388, filed on Nov. 29, 2006, now Pat. No. 7,482,003, which is a continuation of application No. 10/428,662, filed on May 2, 2003, now Pat. No. 7,157,086, which is a continuation of application No. 08/454,899, filed on May 31, 1995, now Pat. No. 6,602,503, which is a continuation-in-part of application No. PCT/US94/00266, filed on Jan. 7, 1994, which is a continuation-in-part of application No. 08/004,798, filed on Jan. 12, 1993, now abandoned.

(51) Int. Cl.
*A61K 39/395* (2006.01)
*C07K 16/28* (2006.01)

(52) U.S. Cl. ............... 424/144.1; 424/130.1; 424/133.1; 424/134.1; 424/136.1; 424/141.1; 424/143.1; 424/153.1; 424/154.1; 424/173.1; 530/387.1; 530/387.3; 530/388.2; 530/388.22; 530/388.7; 530/388.75

(58) Field of Classification Search ........................ None
See application file for complete search history.

(56) References Cited

U.S. PATENT DOCUMENTS

| | | | |
|---|---|---|---|
| 4,816,397 A | 3/1989 | Boss et al. | |
| 4,816,567 A | 3/1989 | Cabilly et al. | |
| 5,217,870 A | 6/1993 | Hession et al. | |
| 5,272,263 A | 12/1993 | Hession et al. | |
| 5,367,056 A | 11/1994 | Hession et al. | |
| 5,530,101 A | 6/1996 | Queen et al. | |
| 5,695,755 A | 12/1997 | Papayannopoulo | |
| 5,824,304 A | 10/1998 | Papayannopoulo | |
| 5,859,205 A | 1/1999 | Adair et al. | |
| 5,871,734 A | 2/1999 | Lobb et al. | |
| 5,888,507 A | 3/1999 | Burkly | |
| 5,932,214 A | 8/1999 | Lobb et al. | |
| 6,252,043 B1 | 6/2001 | Hession et al. | |
| 6,307,025 B1 | 10/2001 | Hession et al. | |
| 6,602,503 B1 | 8/2003 | Lobb et al. | |
| 7,157,086 B2 * | 1/2007 | Lobb et al. | 424/144.1 |
| 7,482,003 B2 * | 1/2009 | Lobb et al. | 424/144.1 |
| 7,829,092 B2 * | 11/2010 | Lobb et al. | 424/144.1 |

FOREIGN PATENT DOCUMENTS

| | | |
|---|---|---|
| EP | 0 120 694 | 10/1984 |
| EP | 0 125 023 | 11/1984 |
| EP | 0 239 400 | 9/1987 |
| EP | 0 330 506 | 8/1989 |
| EP | 0 519 596 | 12/1992 |
| WO | WO 86/01533 | 3/1986 |
| WO | WO 86/05807 | 10/1986 |
| WO | WO 87/04462 | 7/1987 |
| WO | WO 89/01036 | 2/1989 |
| WO | WO 89/07454 | 8/1989 |
| WO | WO 89/10404 | 11/1989 |
| WO | WO 90/07861 | 7/1990 |
| WO | WO 90/13300 | 11/1990 |
| WO | WO 91/09967 | 7/1991 |
| WO | WO 92/04381 | 3/1992 |
| WO | WO 95/19790 | 7/1995 |

OTHER PUBLICATIONS

Albelda, et al., FASEB J., 8:504-512 (1994).
Bebbington, et al., "High-Level Expression of a Recombinant Antibody from Myeloma Cells Using a Glutamine Synthetase Gene as an Amplifiable Selectable Marker," Bio/Technology, 10:169-175 (1992).
Bednarczyk, et al., "Monoclonal Antibody to VLAα Chain (CDw49d) Induce Homotypic Lymphocyte Aggregation," J. Immunol. 144:777-784 (1990).
Begent, et al., "Phase I/II Study of Chimeric B72.3 Antibody in Radioimmunology of Colorectal Carcinoma," Br. J. Cancer 62:487 (1990).
Bevilacqua, et al., "Endothelial Leukocyte Adhesion Molecule 1: An Inducible Receptor for Neutrophils Related to Complement Regulatory Proteins and Lectins," Science 243:1160-1165 (1989).
Bevilacqua, et al., "Identification of an Inducible Endothelial-Leukocyte Adhesion Molecule," Proc. Natl. Acad. Sci. USA 84:9238-9242 (1987).

(Continued)

*Primary Examiner* — Phillip Gambel
(74) *Attorney, Agent, or Firm* — Lando & Anastasi LLP

(57) ABSTRACT

The present invention disclosed recombinant anti-VLA-4 antibody molecules, including humanized recombinant anti-VLA-4 antibody molecules. These antibodies are useful in the treatment of specific and non-specific inflammation, including asthma and inflammatory bowel disease. In addition, the humanized recombinant anti-VLA-4 antibodies disclosed can be useful in methods of diagnosing and localizing sites of inflammation.

1 Claim, No Drawings

OTHER PUBLICATIONS

Bochner et al. (1991) "Adhesion of Human Basophils, Eosinophils, and Neutrophils to Interleukin 1-activated Human Vascular Endothelial Cells: Contributions of Endothelial Cell Adhesion Molecules" J. Exp. Med. 173:1553-1556.
Borrebaeck et al. (1990) "The Use of in Vitro Immunization, Cloning of Variable Regions, and SCID Mice for the Production of Human Monoclonal Antibodies" in Therapeutic Monoclonal Antibodies, Borrebaeck and Larrick (eds.), Stockton Press, Chp. 1:1-15.
Boyd et al. (1988) "Intercellular Adhesion Molecule 1 (ICAM-1) has a Central Role in Cell-Cell Contact-Mediated Immune Mechanisms" Proc. Natl. Acad. Sci. USA 85:3095-3099.
Bruggemann et al. (1989) "The Immunogenicity of Chimeric Antibodies" J. Exp. Med. 170:2153-2157.
Bulinski, "Peptide Antibodies: New Tools for Cell Biology" International Review of Cytology 103:281-302 (1986).
Burkly, et al. Eur. J. Immunol. 1991, 21;2871-2875.
Carlos et al. (1990) "Vascular Cell Adhesion Molecule-1 Mediates Lymphocyte Adherence to Cytokine-Activated Cultured Human Endothelial Cells" Blood 76:965-970.
Clayberger et al. (1987) "Identification and Characterization of Two Novel Lymphocyte Function-Associated Antigens, L24 and L25" J. Immunol. 138:1510-1514.
Co et al. (1991) "Humanized Antibodies for Antiviral Therapy" Proc. Natl. Acad. Sci. USA 88:2869-2873.
Collins et al. (1986) "Recombinant Human Tumor Necrosis Factor Increases mRNA Levels and Surface Expression of HLA-A,B Antigens in Vascular Endothelial Cells and Dermal Fibroblasts in Vitro" Proc. Natl. Acad. Sci. USA 83:446-450.
Cybulsky and Gimbrone, Jr. (1991) "Endothelial Expression of a Mononuclear Leukocyte Adhesion Molecule During Atherogenesis" Science 251:788-791.
Dobrina et al. (1991) "Mechanisms of Eosinophil Adherence to Cultured Vascular Endothelial Cells" J. Clin. Invest. 88:20-26.
Dustin and Springer (1988) "Lymphocyte Function-Associated Antigen-1 (LFA-1) Interaction with Intercellular Adhesion Molecule-1 (ICAM-1) is One of at Least Three Mechanisms for Lymphocyte Adhesion to Cultured Endothelial Cells" J. Cell. Biol. 107:321-331.
Dustin et al. (1986) "Induction by IL 1 and Interferon-γ: Tissue Distribution, Biochemistry, and Function of a Natural Adherence Molecule (ICAM-1)" J. Immunol. 137:245-254.
Edgington (1992) "How Sweet It Is: Selectin-Mediating Drugs" Bio/Technology 10:383-384.
Elices et al. (1990) "VACM-1 on Activated Endothelium Interacts with the Leukocyte Integrin VLA4 at a Site Distinct from the VLA4/Fibronectin Binding Site" Cell 60:577-584.
Favoloro et al. (1980) "Transcriptional Maps of Polyoma Virus Specific RNA: Analysis by Two-Dimensional Nuclease S1 Gel Mapping" Methods in Enzymology 65:718-749.
Flanagan and Rabbitts (1982) "Arrangement of Human Immunoglobulin Heavy Chain Construct Region Genes Implies Evolutionary Amplification of a Segment Containing γ, ε and α Genes" Nature 300:709-713.
Freedman et al. (1990) "Adhesion of Human B Cells to Germinal Centers In Vitro Involves VLA-4 and INCAM-110" Science 249:1030-1033.
Hale et al. (1988) "Remission Induction in Non-Hodgkin Lymphoma with Reshaped Human Monoclonal Antibody CAMPATH-1H", Lancet (Dec. 17, 1988) 1394-1398.
Harlan (1985) "Leukocyte-Endothelial Interactions" Blood 65:513-526.
Harlan, "Leukocyte-Endothelial Interactions" Blood (1985) 65:513-526.
Harris and Emery (1993) "Therapeutic antibodies—the coming of age" TIBTECH 11:42-44.
Hemler (1990) "VLA Proteins in the Integrin Family: Structures, Functions and Their Role on Leukocytes" Annu. Rev. Immunol. 8:365-400.
Hemler et al. (1987) "Characterization of the Cell Surface Heterodimer VLA4 and Related Peptides" J. Biol. Chem. 262:11478-11485.
Hession et al. (1991) "Cloning of an Alternate Form of Vascular Cell Adhesion Molecule-1 (VCAM-1)" J. Biol. Chem. 266:6682-6685.
Hieter et al. (1980) "Cloned Human and Mouse Kappa Immunoglobulin Constant and J Region Genes Conserve Homology in Functional Segments" Cell 22:197-207.
Ho et al. (1989) "Site-Directed Mutagenesis by Overlap Extension Using the Polymerase Chain Reaction" Gene 77:51-59.
Holzmann et al. (1989) "Identification of a Murine Peyer's Patch-Specific Lymphocyte Homing Receptor as an Integrin Molecule with an α Chain Homologous to Human VLA-4α" Cell 56:37-46.
Huse et al. (1989) "Generation of a Large Combinatorial Library of Immunoglobulin Repertoire in Phage Lambda" Science 246:1275-1281.
Hynes (1987) "Integrins: A Family of Cell Surface Receptors" Cell 48:549-554.
Issekutz (1991) "Inhibition of in Vivo Lymphocyte Migration to Inflammation and Homing to Lymphoid Tissues by the TA-2 Monoclonal Antibody" J. Immunol. 147:4178-4184.
Jones and Bendig (1991) "Rapid PCR-Cloning of Full-Length Mouse Immunoglobulin Variable Regions" Bio/Technology 9:88-89.
Kilmartin et al. (1982) "Rat Monoclonal Antitubulin Antibodies Derived by Using a New Non-Secreting Rat Cell Line" J. Cell. Biol. 93:576-582.
Kishimoto et al. (1989) "The Leukocyte Integrins" Adv. Immunol. 46:149-182.
Kohler and Milstein (1975) "Continuous Cultures of Fused Cells Secreting Antibody of Predefined Specificity" Nature 265:495-497.
Leeuwenberg et al. (1989) "Induction of an Activation Antigen on Human Endothelial Cells in vitro" Eur. J. Immunol. 19:715-729.
Lobb et al. (1991) "Expression and Functional Characterization of a Soluble Form of Vascular Cell Adhesion Molecule 1" Biochem. Biophys. Res. Comm. 178: 1498-1504.
Lobb et al. (1991) "Expression and Functional Characterization of a Soluble Form of Endothelial-Leukocyte Adhesion Molecule 1" J. Immunol. 147:124-129.
Marcantonio and Hynes (1988) "Antibodies to the Conserved Cytoplasmic Domain of the Integrin $\beta_1$ Subunit React with Proteins in Vertebrates, Invertebrates and Fungi" J. Cell. Biol. 106:1765-1772.
Marcantonio, et al., "Antibodies to the Conserved Cytoplasmic Domain of the Integrin β1 Subunit React with Proteins in Vertebrates, Invertebrates and Fungi" J. Cell. Biol. (1988) 106:1765-1772.
Miller et al., "Use of antibodies in the study of protein structure and function in lung diseases" Am. J. Physiol. 260(2):L1-L12 (1991).
Miyake et al. (1991) "A VCAM-like Adhesion Molecule on Murine Bone Marrow Stromal Cells Mediates Binding of Lymphocyte Precursors in Culture" J. Cell. Biol. 114:557-565.
Orlandi et al. (1989) "Cloning Immunoglobulin Variable Domains for Expression by the Polymerase Chain Reaction" Proc. Natl. Acad. Sci. USA 86:3833-3837.
Osborn (1990) "Leukocyte Adhesion to Endothelium in Inflammation" Cell 62:3-6.
Osborn et al. (1989) "Direct Expression Cloning of Vascular Cell Adhesion Molecule 1, a Cytokine-Induced Endothelial Protein That Binds to Lymphocytes" Cell 59:1203-1211.
Paul, Fundamental Immunology, Raven Press, NY (1993), p. 242 only.
Pober et al. (1986) "Overlapping Patterns of Activation of Human Endothelial Cells by Interleukin 1, Tumor Necrosis Factor, and Immune Interferon" J. Immunol. 137:1893-1896.
Pober, et al., "Overlapping Patterns of Activation of Human Endothelial Cells by Interleukin 1, Tumor of Necrosis Factor, and Immune Interferon" J. Immunol. (1986) 137:1893-1896.
Polte et al. (1990) "Full Length Vascular Cell Adhesion Molecule 1 (VCAM-1)" Nuc. Ac. Res. 18(19):5901.
Pulido et al. (1991) "Functional Evidence for Three Distinct and Independently Inhibitable Adhesion Activities Mediated by the Human Integrin VLA-4" J. Biol. Chem. 266:10241-10245.
Queen et al. (1989) "A Humanized Antibody That Binds to the Interleukin 2 Receptor" Proc. Natl. Acad. Sci. USA 86:10029-10033.
Rice and Bevilacqua (1989) "An Inducible Endothelial Cell Surface Glycoprotein Mediates Melanoma Adhesion" Science 246:1303-1306.
Riechmann et al. (1988) "Reshaping Human Antibodies for Therapy" Nature 332:323-327.

Ruoslahti (1988) "Fibronectin and Its Receptors" Annu. Rev. Biochem. 57:375-413.

Saiki et al. (1988) "Primer-Directed Enzymatic Amplification of DNA with a Thermostable DNA Polymerase" Science 239:487-491.

Saldanha JW et al. Mol Immunol Aug. 1999:36(11-12):709-19 (Abstract Only).

Sanchez-Madrid et al. (1986) "VLA-3: A Novel Polypeptide Association Within the VLA Molecular Complex: Cell Distribution and Biochemical Characterization" Eur. J. Immunol. 16:1343-1349.

Sanger et al. (1977) "DNA Sequencing with Chain-Terminating Inhibitors" Proc. Natl. Acad. Sci. USA 74:5463-5467.

Schroff et al. (1985) "Human-Antimurine Immunoglobulin Responses in Patients Receiving Monoclonal Antibody Therapy" Cancer Res. 45:879-885.

Takada et al. (1989) "The Primary Structure of the $\alpha_4$ Subunit of VLA4: Homology to Other Integrins and a Possible Cell-Cell Adhesion Function" EMBO J. 8:1361-1368.

Takahashi et al. (1982) "Structure of Human Immunoglobulin Gamma Genes: Implications for Evolution of a Gene Family" Cell 29:671-679.

Tempest et al. (1991) "Reshaping a Human Monoclonal Antibody to Inhibit Human Respiratory Syncytial Virus Infectioin in Vivo" Bio/Technology 9:266-271.

Verhoeyen et al. (1988) "Reshaping Human Antibodies: Grafting an Antilysozyme Activity" Science 239:1534-1536.

Verhoeyen et al. (1991) "Reshaping of Human Antibodies Using CDR-Grafting" in Monoclonal Antibodies, Chapman and Hall (eds.), 37-43.

von Andrian et al. N Engl J Med 348;68-72 (2003).

Walsh et al. (1991) "Human Eosinophil, but Not Neutrophil, Adherence to IL-1-Stimulated Human Umbilical Vascular Endothelial Cells Is $\alpha_4\beta_1$ (Very Late Antigen-4) Dependent" J. Immunol. 146:3419-3423.

Ward, et al., Therapeutic Immunology, 1:165-171 (1994).

Wayner et al. (1989) "Identification and Characterization of the Lymphocyte Adhesion Receptor for an Alternative Cell Attachment Domain (CS-1) in Plasma Fibronectin" J. Cell. Biol. 109:1321-1330.

Weller et al. (1991) "Human Eosinophil Adherence to Vascular Endothelium Mediated by Binding to Vascular Cell Adhesion Molecule 1 and Endothelial Leukocyte Adhesion Molecule 1" Proc. Natl. Acad. Sci. USA 88:7430-7433.

Winter and Harris (1993) "Antibody-based Therapy" TIPS 14:139-143.

Wu et al. (1970) "An Analysis of the Sequences of the Variable Regions of Bence Jones Proteins and Myeloma Light Chains and Their Implications for Antibody Complementarity" J. Exp. Med. 132:211-250.

\* cited by examiner

RECOMBINANT ANTI-VLA4 ANTIBODY MOLECULES

RELATED APPLICATIONS

This application is a continuation application of U.S. patent application Ser. No. 12/338,570, filed Dec. 18, 2008, now U.S. Pat. No. 7,829, 092,which is a continuation of U.S. patent application Ser. No. 11/606,388, filed on Nov. 29, 2006, now U.S. Pat. No. 7,482,003, which is a continuation application of U.S. patent application Ser. No. 10/428,662, filed on May 2, 2003, now U.S. Pat. No. 7,157,086, which is a continuation application of U.S. patent application Ser. No. 08/454,899, filed on May. 31, 1995, now U.S. Pat. No. 6,602, 503, which is a contination-in-part application U.S. patent application Ser. No. 08/004,798, filed Jan. 12,1993, now abandoned, and is a continuation-in-part application of International Patent Application Serial No. PCT/US94/00266, filed on Jan. 7, 1994. The contents of the prior applications are hereby incorporated by reference in their entirety for all purposes.

FIELD OF THE INVENTION

The present invention relates to recombinant anti-VLA-4 antibody molecules, including humanized recombinant anti-VLA-4 antibody molecules.

BACKGROUND OF THE INVENTION

A. Immunoglobulins and Monoclonal Antibodies

Natural immunoglobulins have been known for many years, as have the various fragments thereof, such as the Fab, (Fab')$_2$ and Fc fragments, which can be derived by enzymatic cleavage. Natural immunoglobulins comprise generally a Y-shaped molecule having an antigen-binding site towards the free end of each upper arm. The remainder of the structure, and particularly the stem of the Y, mediates the effector functions associated with immunoglobulins.

Specifically, immunoglobulin molecules are comprised of two heavy (H) and two light (L) polypeptide chains, held together by disulfide bonds. Each chain of an immunoglobulin chain is divided into regions or domains, each being approximately 110 amino acids. The light chain has two such domains while the heavy chain has four domains. The amino acid sequence of the amino-terminal domain of each polypeptide chain is highly variable (V region), while the sequences of the remaining domains are conserved or constant (C regions). A light chain is therefore composed of one variable ($V_L$) and one constant domain ($C_L$) while a heavy chain contains one variable ($V_H$) and three constant domains ($CH_1$, $CH_2$ and $CH_3$). An arm of the Y-shaped molecule consists of a light chain (V+$C_L$) and the variable domain ($V_H$) and one constant domain ($CH_1$) of a heavy chain. The tail of the Y is composed of the remaining heavy chain constant domains ($CH_2$+$CH_3$). The C-terminal ends of the heavy chains associate to form the Fc portion. Within each variable region are three hypervariable regions. These hypervariable regions are also described as the complementarity determining regions (CDRs) because of their importance in binding of antigen. The four more conserved regions of the variable domains are described as the framework regions (FRs). Each domain of an immunoglobulin consists of two beta-sheets held together by a disulfide bridge, with their hydrophobic faces packed together. The individual beta strands are linked together by loops. The overall appearance can be described as a beta barrel having loops at the ends. The CDRs form the loops at one end of the beta barrel of the variable region.

Natural immunoglobulins have been used in assay, diagnosis and, to a more limited extent, therapy. However, such uses, especially in therapy, have been hindered by the polyclonal nature of natural immunoglobulins. A significant step towards the realization of the potential of immunoglobulins as therapeutic agents was the discovery of techniques for the preparation of monoclonal antibodies (MAbs) of defined specificity, Kohler et al., 1975 [1]. However, most MAbs are produced by fusions of rodent (i.e., mouse, rat) spleen cells with rodent myeloma cells. They are therefore essentially rodent proteins.

By 1990, over 100 murine monoclonal antibodies were in clinical trials, particularly in the U.S. and especially for application in the treatment of cancer. However, by this time it was recognized that rejection of murine monoclonal antibodies by the undesirable immune response in humans termed the HAMA (Human Anti-Mouse Antibody) response was a severe limitation, especially for the treatment of chronic disease. Therefore, the use of rodent MAbs as therapeutic agents in humans is inherently limited by the fact that the human subject will mount an immunological response to the MAb and either remove the MAb entirely or at least reduce its effectiveness. In practice MAbs of rodent origin may not be used in a patient for more than one or a few treatments as a HAMA response soon develops rendering the MAb ineffective as well as giving rise to undesirable reactions. In fact, a HAMA response has been observed in the majority of patients following a single injection of mouse antibody, (Schroff et al., 1985 [2]). A solution to the problem of HAMA is to administer immunologically compatible human monoclonal antibodies. However, the technology for development of human monoclonal antibodies has lagged well behind that of murine antibodies (Borrebaeck et al., 1990 [3]) such that very few human antibodies have proved useful for clinical study.

Proposals have therefore been made for making non-human MAbs less antigenic in humans. Such techniques can be generically termed "humanization" techniques. These techniques generally involve the use of recombinant DNA technology to manipulate DNA sequences encoding the polypeptide chains of the antibody molecule. The use of recombinant DNA technology to clone antibody genes has provided an alternative whereby a murine monoclonal antibody can be converted to a predominantly human-form (i.e., humanized) with the same antigen binding properties (Riechmann et al., 1988 [4]). Generally, the goal of the humanizing technology is to develop humanized antibodies with very little or virtually no murine component apart from the CDRs (see, e.g., Tempest et al., 1991 [5]) so as to reduce or eliminate their immunogenicity in humans.

Early methods for humanizing MAbs involved production of chimeric antibodies in which an antigen binding site comprising the complete variable domains of one antibody is linked to constant domains derived from another antibody. Methods for carrying out such chimerization procedures have been described, for example, in EP 120694 [6], EP 125023 [7], and WO 86/01533 [8]. Generally disclosed are processes for preparing antibody molecules having the variable domains from a non-human MAb such as a mouse MAb and the constant domains from a human immunoglobulin. Such chimeric antibodies are not truly humanized because they still contain a significant proportion of non-human amino acid sequence, i.e., the complete non-human variable domains, and thus may still elicit some HAMA response, particularly if administered over a prolonged period, Begent et al., 1990 [9].

In addition, it is believed that these methods in some cases (e.g., EP 120694 [6]; EP 125023 [7] and U.S. Pat. No. 4,816, 567 [10]) did not lead to the expression of any significant quantities of Ig polypeptide chains, nor the production of Ig activity without in vitro solubilization and chain reconstitution, nor to the secretion and assembly of the chains into the desired chimeric recombinant antibodies. These same problems may be noted for the initial production of non-chimeric recombinant antibodies (e.g., U.S. Pat. No. 4,816,397 [11]).

B. Humanized Recombinant Antibodies and CDR-Grafting Technology

Following the early methods for the preparation of chimeric antibodies, a new approach was described in EP 0239400 [12] whereby antibodies are altered by substitution of their complementarity determining regions (CDRs) for one species with those from another. This process may be used, for example, to substitute the CDRs from human heavy and light chain Ig variable region domains with alternative CDRs from murine variable region domains. These altered Ig variable regions may subsequently be combined with human Ig constant regions to created antibodies which are totally human in composition except for the substituted murine CDRs. Such murine CDR-substituted antibodies would be predicted to be less likely to elicit a considerably reduced immune response in humans compared to chimeric antibodies because they contain considerably less murine components.

The process for humanizing monoclonal antibodies via CDR grafting has been termed "reshaping". (Riechmann et al., 1988 [4]; Verhoeyen et al., 1988 [13]). Typically, complementarity determining regions (CDRs) of a murine antibody are transplanted onto the corresponding regions in a human antibody, since it is the CDRs (three in antibody heavy chains, three in light chains) that are the regions of the mouse antibody which bind to a specific antigen. Transplantation of CDRs is achieved by genetic engineering whereby CDR DNA sequences are determined by cloning of murine heavy and light chain variable (V) region gene segments, and are then transferred to corresponding human V regions by site-directed mutagenesis. In the final stage of the process, human constant region gene segments of the desired isotype (usually gamma 1 for $C_H$ and kappa for $C_L$) are added and the humanized heavy and light chain genes are coexpressed in mammalian cells to produce soluble humanized antibody.

The transfer of these CDRs to a human antibody confers on this antibody the antigen binding properties of the original murine antibody. The six CDRs in the murine antibody are mounted structurally on a V region "framework" region. The reason that CDR-grafting is successful is that framework regions between mouse and human antibodies may have very similar 3-D structures with similar points of attachment for CDRs, such that CDRs can be interchanged. Nonetheless, certain amino acids within framework regions are thought to interact with CDRs and to influence overall antigen binding affinity. The direct transfer of CDRs from a murine antibody to produce a recombinant humanized antibody without any modifications of the human V region frameworks often results in a partial or complete loss of binding affinity.

In Riechmann et al., 1988 [4] and WO 89/07454 [14], it was found that transfer of the CDR regions alone (as defined by Kabat et al., 1991 [15] and Wu et al., 1970 [16]) was not sufficient to provide satisfactory antigen binding activity in the CDR-grafted product. Riechmann et al. 1988 [4] found that it was necessary to convert a serine residue at position 27 of the human sequence to the corresponding rat phenylalanine residue to obtain a CDR-grafted product having satisfactory antigen binding activity. This residue at position 27 of the heavy chain is within the structural loop adjacent to CDR1. A further construct which additionally contained a human serine to rat tyrosine change at position 30 of the heavy chain did not have a significantly altered binding activity over the humanized antibody with the serine to phenylalanine change at position 27 alone. These results indicate that changes to residues of the human sequence outside the CDR regions, for example, in the loop adjacent to CDR1, may be necessary to obtain effective antigen binding activity for CDR-grafted antibodies which recognize more complex antigens. Even so, the binding affinity of the best CDR-grafted antibodies obtained was still significantly less than the original MAb.

More recently, Queen et al., 1989 [17] and WO 90/07861 [18] have described the preparation of a humanized antibody that binds to the interleukin 2 receptor, by combining the CDRs of a murine MAb (anti-Tac) with human immunoglobulin framework and constant regions. They have demonstrated one solution to the problem of the loss of binding affinity that often results from direct CDR transfer without any modifications of the human V region framework residues; their solution involves two key steps. First, the human V framework regions are chosen by computer analysts for optimal protein sequence homology to the V region framework of the original murine antibody, in this case, the anti-Tac MAb. In the second step, the tertiary structure of the murine V region is modelled by computer in order to visualize framework amino acid residues which are likely to interact with the murine CDRs and these murine amino acid residues are then superimposed on the homologous human framework. Their approach of employing homologous human frameworks with putative murine contact residues resulted in humanized antibodies with similar binding affinities to the original murine antibody with respect to antibodies specific for the interleukin 2 receptor (Queen et al., 1989 [17]) and also for antibodies specific for herpes simplex virus (HSV) (Co. et al., 1991 [19]). However, the reintroduction of murine residues into human frameworks (at least 9 for anti-interleukin 2 receptor antibodies, at least 9 and 7 for each of two anti-HSV antibodies) may increase the prospect of HAMA response to the framework region in the humanized antibody. Bruggemann et al., 1989 [20] have demonstrated that human V region frameworks are recognized as foreign in mouse, and so, conversely, murine modified human frameworks might give rise to an immune reaction in humans.

According to the above described two step approach in WO 90/07861 [18], Queen et al. outlined four criteria for designing humanized immunoglobulins. The first criterion is to use as the human acceptor the framework from a particular human immunoglobulin that is usually homologous to the non-human donor immunoglobulin to be humanized, or to use a consensus framework from many human antibodies. The second criterion is to use the donor amino acid rather than the acceptor if the human acceptor residue is unusual and the donor residue is typical for human sequences at a specific residue of the framework. The third criterion is to use the donor framework amino acid residue rather than the acceptor at positions immediately adjacent to the CDRs. The fourth criterion is to use the donor amino acid residue at framework positions at which the amino acid is predicted to have a side chain atom within about 3 Å of the CDRs in a three-dimensional immunoglobulin model and to be capable of interacting with the antigen or with the CDRs of the humanized immunoglobulin. It is proposed that criteria two, three or four may be applied in addition or alternatively to criterion one, or each criteria may be applied singly or in any combination.

In addition, WO 90/07861 [18] details the preparation of a single CDR-grafted humanized antibody, a humanized antibody specificity for the p55 Tac protein of the IL-2 receptor, by employing the combination of all four criteria, as above, in designing this humanized antibody. The variable region frameworks of the human antibody EU (see, Kabat et al., 1991 [15]) were used as acceptor. In the resultant humanized antibody, the donor CDRs were as defined by Kabat et al., 1991 [15] and Wu et al., 1970 [16] and, in addition, the mouse donor residues were used in place of the human acceptor residues, at positions 27, 30, 48, 66, 67, 89, 91, 94, 103, 104, 105 and 107 in heavy chain and at positions 48, 60 and 63 in the light chain, of the variable region frameworks. The humanized anti-Tac antibody obtained was reported to have an affinity for p55 of $3\times10^9$ $M^{-1}$, about one-third of that of the murine MAb.

Several other groups have demonstrated that Queen et al.'s approach of first choosing homologous frameworks followed by reintroduction of mouse residues may not be necessary to achieve humanized antibodies with similar binding affinities to the original mouse antibodies (Riechmann et al., 1988 [4]; Tempest et al., 1991 [5]; Verhoeyen, et al. 1991 [21]). Moreover, these groups have used a different approach and have demonstrated that it is possible to utilize, as standard, the V region frameworks derived from NEWM and REI heavy and light chains respectively for CDR-grafting without radical introduction of mouse residues. However, the determination of which mouse residues should be introduced to produce antibodies with binding efficiencies similar to the original murine MAb can be difficult to predict, being largely empirical and not taught by available prior art. In the case of the humanized CAMPATH-IH antibody, the substitution of a phenylalanine for a serine residue at position 27 was the only substitution required to achieve a binding efficiency similar to that of the original murine antibody (Riechmann, et al., 1988 [4]; WO92/04381 [22]). In the case of a humanized (reshaped) antibody specific for respiratory syncytial virus (RSV) for the inhibition of RSV infection in vivo, substitution of a block of 3 residues adjacent to CDR3 in the CDR-grafted NEWM heavy chain was required to produce biological activity equivalent to the original mouse antibody (Tempest et al., 1991 [5]; WO 92/04381 [22]). The reshaped antibody in which only the mouse CDRs were transferred to the human framework showed poor binding for RSV. An advantage of using the Tempest et al., 1991 [5] approach to construct NEWM and REI based humanized antibodies is that the 3-dimensional structures of NEWM and REI variable regions are known from x-ray crystallography and thus specific interactions between CDRs and V region framework residues can be modelled.

Regardless of the approach taken, the examples of the initial humanized antibodies prepared to date have shown that it is not a straightforward process to obtain humanized antibodies with the characteristics, in particular, the binding affinity, as well as other desirable properties, of the original murine MAb from which the humanized antibody is derived. Regardless of the approach to CDR grafting taken, it is often not sufficient merely to graft the CDRs from a donor Ig onto the framework regions of an acceptor Ig (see, e.g., Tempest et al., 1991 [5], Riechmann et al., 1988 [4], etc., cited herein). In a number of cases, it appears to be critical to alter residues in the framework regions of the acceptor antibody in order to obtain binding activity. However, even acknowledging that such framework changes may be necessary, it is not possible to predict, on the basis of the available prior art, which, if any, framework residues will need to be altered to obtain functional humanized recombinant antibodies of the desired specificity. Results thus far indicate that changes necessary to preserve specificity and/or affinity are for the most part unique to a given antibody and cannot be predicted based on the humanization of a different antibody.

In particular, the sets of residues in the framework region which are herein disclosed as being of critical importance to the activity of the recombinant humanized anti-VLA-4 antibodies constructed in accordance with the teachings of the present invention do not generally coincide with residues previously identified as critical to the activity of other humanized antibodies and were not discovered based on the prior art.

C. Therapeutic Applications of Humanized Antibodies

To date, humanized recombinant antibodies have been developed mainly for therapeutic application in acute disease situations (Tempest, et al., 1991 [5]) or for diagnostic imaging (Verhoeyen, et al., 1991 [21]). Recently, clinical studies have begun with at least two humanized antibodies with NEWM and REI V region frameworks, CAMPATH-IH (Riechmann et al., 1988 [4]) and humanized anti-placental alkaline phosphatase (PLAP) (Verhoeyen et al., 1991 [21]) and these studies have initially indicated the absence of any marked immune reaction to these antibodies. A course of treatment with CAMPATH-IH provided remission for two patients with non-Hodgkin's lymphoma thus demonstrating efficacy in a chronic disease situation (Hale et al., 1988 [23]). In addition, the lack of immunogenicity of CAMPATH-1H was demonstrated after daily treatment of the two patients for 30 and 43 days. Since good tolerance to humanized antibodies has been initially observed with CAMPATH-IH, treatment with humanized antibody holds promise for the prevention of acute disease and to treatment of diseases with low mortality.

D. The VCAM-VLA-4 Adhesion Pathway and Antibodies to VLA-4

Vascular endothelial cells constitute the lining of blood vessels and normally exhibit a low affinity for circulating leukocytes (Harlan, 1985 [24]). The release of cytokines at sites of inflammation, and in response to immune reactions, causes their activation and results in the increased expression of a host of surface antigens. (Collins et al., 1986 [25]; Pober et al., 1986 [26]; Bevilacqua et al., 1987 [27]; Leeuwenberg et al., 1989 [28]). These include the adhesion proteins ELAM-1, which binds neutrophils (Bevilacqua et al., 1989 [29], ICAM-1 which interacts with all leukocytes (Dustin et al., 1986 [30]; Pober et al. 1986, [26]; Boyd et al., 1988 [31]; Dustin and Springer, 1988 [32]), and VCAM-1 which binds lymphocytes (Osborn et al., 1989 [33]). These cytokine-induced adhesion molecules appear to play an important role in leukocyte recruitment to extravascular tissues.

The integrins are a group of cell-extracellular matrix and cell-cell adhesion receptors exhibiting an alpha-beta heterodimeric structure, with a widespread cell distribution and a high degree of conservation throughout evolution (Hynes, 1987 [34]; Marcantonio and Hynes, 1988 [35]). The integrins have been subdivided into three major subgroups; the $\beta_2$ subfamily of integrins (LFA-1, Mac-1, and p150, 95) is mostly involved in cell-cell interactions within the immune system (Kishimoto et al., 1989 [36]), whereas members of the $\beta_1$ and $\beta_3$ integrin subfamilies predominantly mediate cell attachment to the extracellular matrix (Hynes, 1987 [34]; Ruoslahti, 1988 [37]). In particular, the $\beta_1$ integrin family, also termed VLA proteins, includes at least six receptors that specifically interact with fibronectin, collagen, and/or laminin (Hemler, 1990 [38]). Within the VLA family, VLA-4 is atypical because it is mostly restricted to lymphoid and myeloid cells (Hemler et al., 1987 [39]), and indirect evidence had suggested that it might be involved in various cell-cell interactions (Clayberger et al., 1987 [40]; Takada et al., 1989 [41]; Holtzmann et al., 1989 [42]; Bendarczyk and McIntyre, 1990 [43]). In addition, VLA-4 has been shown to mediate T and B lymphocyte attachment to the heparin II binding fragment of human plasma fibronectin (FN) (Wayner et al., 1989 [44]).

VCAM-1, like ICAM-1, is a member of the immunoglobulin gene superfamily (Osborn et al., 1989 [33]). VCAM-1 and VLA-4 were demonstrated to be a ligand-receptor pair that allows attachment of lymphocytes to activated endothelium by Elices et al., 1990 [45]. Thus, VLA-4 represents a singular example of a $\beta_1$ integrin receptor participating in both cell-cell and cell-extracellular matrix adhesion functions by means of the defined ligands VCAM-1 and FN.

VCAM1 (also known as INCAM-110) was first identified as an adhesion molecule induced on endothelial cells by inflammatory cytokines (TNF and IL-1) and LPS (Rice et al., 1989 [46]; Osborn et al., 1989 [33]). Because VCAM1 binds to cells exhibiting the integrin VLA-4 ($\alpha_4\beta_1$) including T and B lymphocytes, monocytes, and eosinophils, but not neutrophils, it is thought to participate in recruitment of these cells from the bloodstream to areas of infection and inflammation (Elices et al, 1990 [45]; Osborn, 1990 [33]). The VCAM1/VLA-4 adhesion pathway has been associated with a number of physiological and pathological processes. Although VLA-4 is normally restricted to hematopoietic lineages, it is found on melanoma cell lines, and thus it has been suggested that VCAM1 may participate in metastasis of such tumors (Rice et al., 1989 [46]).

In vivo, VCAM1 is found on areas of arterial endothelium representing early atherosclerotic plaques in a rabbit model system (Cybulsky and Gimbrone, 1991 [47]). VCAM1 is also found on follicular dendritic cells in human lymph nodes (Freedman et al., 1990 [48]). It is also present on bone marrow stromal cells in the mouse (Miyake et al., 1991 [49]), thus VCAM1 appears to play a role in B-cell development.

The major form of VCAM1 in vivo on endothelial cells, has been referred to as VCAM-7D, and has seven Ig homology units or domains; domains 4, 5 and 6 are similar in amino acid sequence to domains 1, 2 and 3, respectively, suggesting an intergenic duplication event in the evolutionary history of the gene (Osborn et al., 1989 [33]; Polte et al. 1990 [50]; Hession et al., 1991 [51]; Osborn and Benjamin, U.S. Ser. No. 07/821,712 filed Sep. 30, 1991, [52]). A 6-domain form (referred to as VCAM-6D herein) is generated by alternative splicing, in which the fourth domain is deleted (Osborn et al., 1989 [33]; Hession et al. 1991 [51], Cybulsky et al., 1991 [47]; Osborn and Benjamin, U.S. Ser. No. 07/821,712 filed Sep. 30, 1991 [52]). The VCAM-6D, was the first sequenced of these alternate forms, however, later in vivo studies showed that the VCAM-7D form was dominant in vivo. The biological significance of the alternate splicing is not known, however as shown by Osborn and Benjamin, U.S. Ser. No. 07/821,712 filed Sep. 30, 1991 [52], VCAM-6D can bind VLA-4-expressing cells and thus clearly has potential functionality in vivo.

The apparent involvement of the VCAM1/VLA-4 adhesion pathway in infection, inflammation and possibly atherosclerosis has led to continuing intensive research to understand the mechanisms of cell-cell adhesion on a molecular level and has led investigators to propose intervention in this adhesion pathway as a treatment for diseases, particularly inflammation (Osborn et al., 1989 [33]). One method of intervention in this pathway could involve the use of anti-VLA-4 antibodies.

Monoclonal antibodies that inhibit VCAM 1 binding to VLA-4 are known. For example, anti-VLA-4 MAbs HP2/1 and HP1/3 have been shown to block attachment of VLA-4-expressing Ramos cells to human umbilical vein cells and VCAM1-transfected COS cells (Elices et al., 1990 [45]). Also, anti-VCAM1 antibodies such as the monoclonal antibody 4B9 (Carlos et al., 1990 [53]) have been shown to inhibit adhesion of Ramos (B-cell-like), Jurkat (T-cell-like) and HL60 (granulocyte-like) cells to COS cells transfected to express VCAM-6D and VCAM-7D (Hession et al., 1991 [51]).

The monoclonal antibodies to VLA-4 that have been described to date fall into several categories based on epitope mapping studies (Pulido, et al., 1991 [54]). Importantly one particular group of antibodies, to epitope "B", are effective blockers of all VLA-4-dependent adhesive functions (Pulido et al., 1991, [54]). The preparation of such monoclonal antibodies to epitope B of VLA 4, including, for example the HP1/2 MAb, have been described by Sanchez-Madrid et al., 1986, [55]. Antibodies having similar specificity and having high binding affinities to VLA-4 comparable to that of HP1/2, would be particularly promising candidates for the preparation of humanized recombinant anti-VLA-4 antibodies useful as assay reagents, diagnostics and therapeutics.

As stated above, inflammatory leukocytes are recruited to sites of inflammation by cell adhesion molecules that are expressed on the surface of endothelial cells and which act as receptors for leukocyte surface proteins or protein complexes. In particular, eosinophils have recently been found to participate in three distinct cell adhesion pathways to vascular endothelium, binding to cells expressing intercellular adhesion molecule-1 (ICAM-1), endothelial cell adhesion molecule-1 (ELAM-1), and vascular cell adhesion molecule-1 (VCAM-1) (Weller et al., 1991 [56]; Walsh et al., 1991 [57]; Bochner et al., 1991 [58]; and Dobrina et al., 1991 [59]). That eosinophils express VLA-4 differentiates them from other inflammatory cells such as neutrophils, which bind to ELAM-1 and ICAM-1 but not VCAM-1.

The VLA-4-mediated adhesion pathway has been investigated in an asthma model to examine the possible role of VLA-4 in leukocyte recruitment to inflamed lung tissue (Lobb, U.S. Ser. No. 07/821,768 filed Jan. 13, 1992 [60]). Administering anti-VLA-4 antibody inhibited both the late phase response and airway hyperresponsiveness in allergic sheep. Surprisingly, administration of anti-VLA-4 led to a reduction in the number of both neutrophils and eosinophils in the lung at 4 hours after allergen challenge, even though both cells have alternate adhesion pathways by which they can be recruited to lung tissues. Also surprisingly, inhibition of hyperresponsiveness in the treated sheep was observed which continued to 1 week, even though infiltration of leukocytes, including neutrophils and eosinophils, was not significantly reduced over time.

The VLA-4-mediated adhesion model has also been investigated in a primate model of inflammatory bowel disease (IBD) (Lobb, U.S. Ser. No, 07/835,139 filed Feb. 12, 1992 [61]). The administration of anti-VLA-4 antibody surprisingly and significantly reduced acute inflammation in that model, which is comparable to ulcerative colitis in humans.

More recently, anti-VLA-4 antibodies have been used in methods for the peripheralizing of CD34+ cells, including hematopoietic stem cells as described in Papayannopoulou, U.S. Ser. No. 07/977,702, filed Nov. 13, 1992 [62].

Thus, anti-VLA-4 antibodies having certain epitopic specificities and certain binding affinities may be therapeutically useful in a variety of inflammatory conditions, including asthma and IBD. In particular, humanized recombinant versions of such anti-VLA-4 antibodies, if they could be constructed, might be especially useful for administration in humans. Such humanized antibodies would have the desired potency and specificity, while avoiding or minimizing an immunological response which would render the antibody ineffective and/or give rise to undesirable side effects.

SUMMARY OF THE INVENTION

The present invention provides a method of constructing a recombinant anti-VLA-4 antibody molecule. Specifically, recombinant antibodies according to the present invention comprise the antigen binding regions derived from the heavy and/or light chain variable regions of an anti-VLA-4 antibody.

The present invention provides a method for the construction of humanized recombinant antibody molecule using as a first step CDR grafting or "reshaping" technology. Specifically, the humanized antibodies according to the present invention have specificity for VLA-4 and have an antigen binding site wherein at least one or more of the complementarity determining regions (CDRs) of the variable domains are derived from a donor non-human anti-VLA-4 antibody, and in which there may or may not have been minimal alteration of the acceptor antibody heavy and/or light variable framework region in order to retain donor antibody binding specificity. Preferably, the antigen binding regions of the CDR-grafted heavy chain variable domain comprise the CDRs corresponding to positions 31-35 (CDR1), 50-65 (CDR2) and 95-102 (CDR3). Preferably, the antigen binding regions of the CDR-grafted light chain variable domain comprise CDRs corresponding to positions 24-34 (CDR1), 50-56 (CDR2) and 89-97 (CDR3). These residue designations are numbered according to the Kabat numbering (Kabat et al., 1991 [15]). Thus, the residue/position designations do not always correspond directly with the linear numbering of the amino acid residues shown in the sequence listing. In the case of the humanized $V_K$ sequence disclosed herein, the Kabat numbering does actually correspond to the linear numbering of amino acid residues shown in the sequence listing. In contrast, in the case of the humanized $V_H$ sequences disclosed herein, the Kabat numbering does not correspond to the linear numbering of amino acid residues shown in the sequence listing (e.g., for the humanized $V_H$ regions disclosed in the sequence listing, CDR2=50-66, CDR3=99-110).

The invention further provides the recombinant and humanized anti-VLA-4 antibodies which may be detectably labelled.

The invention additionally provides a recombinant DNA molecule capable of expressing the recombinant and humanized anti-VLA-4 antibodies of the present invention.

The invention further provides host cells capable of producing the recombinant and humanized anti-VLA-4 antibodies of the present invention.

The invention additionally relates to diagnostic and therapeutic uses for the recombinant and humanized anti-VLA-4 antibodies of the present invention.

The invention further provides a method for treating inflammation resulting from a response of the specific defense system in a mammalian subject, including humans, which comprises providing to a subject in need of such treatment an amount of an anti-inflammatory agent sufficient to suppress the inflammation wherein the anti-inflammatory agent is a recombinant and humanized anti-VLA-4 antibody of the present invention.

The invention further provides a method for treating nonspecific inflammation in a mammalian subject, including humans using the recombinant and humanized anti-VLA-4 antibodies.

The invention further concerns the embodiment of the above-described methods wherein the recombinant and humanized anti-VLA-4 antibodies of the present invention are derived from the murine monoclonal antibody HP1/2.

DETAILED DESCRIPTION OF SPECIFIC EMBODIMENTS OF THE INVENTION

The technology for producing monoclonal antibodies is well known. Briefly, an immortal cell line (typically myeloma cells) is fused to lymphocytes (typically splenocytes) from a mammal immunized with whole cells expressing a given antigen, e.g., VLA-4, and the culture supernatants of the resulting hybridoma cells are screened for antibodies against the antigen (see, generally, Kohler et al., 1975 [1]).

Immunization may be accomplished using standard procedures. The unit dose and immunization regimen depend on the species of mammal immunized, its immune status, the body weight of the mammal, etc. Typically, the immunized mammals are bled and the serum from each blood sample is assayed for particular antibodies using appropriate screening assays. For example, anti-VLA-4 antibodies may be identified by immunoprecipitation of $^{125}$I-labeled cell lysates from VLA-4-expressing cells (see, Sanchez-Madrid et al., 1986 [55] and Hemler et al., 1987 [39]). Anti-VLA-4 antibodies may also be identified by flow cytometry, e.g., by measuring fluorescent staining of Ramos cells incubated with an antibody believed to recognize VLA-4 (see, Elices et al., 1990 [45]). The lymphocytes used in the production of hybridoma cells typically are isolated from immunized mammals whose sera have already tested positive for the presence of anti-VLA-4 antibodies using such screening assays.

Typically, the immortal cell line (e.g., a myeloma cell line) is derived from the same mammalian species as the lymphocytes. Preferred immortal cell lines are mouse myeloma cell lines that are sensitive to culture medium containing hypoxanthine, aminopterin and thymidine ("HAT medium").

Typically, HAT-sensitive mouse myeloma cells are fused to mouse splenocytes using 1500 molecular weight polyethylene glycol ("PEG 1500"). Hybridoma cells resulting from the fusion are then selected using HAT medium, which kills unfused and unproductively fused myeloma cells (unfused splenocytes die after several days because they are not transformed). Hybridomas producing a desired antibody are detected by screening the hybridoma culture supernatants. For example, hybridomas prepared to produce anti-VLA-4 antibodies may be screened by testing the hybridoma culture supernatant for secreted antibodies having the ability to bind to a recombinant $\alpha_4$-subunit-expressing cell line, such as transfected K-562 cells (see, e.g., Elices et al., 1990 [45]).

To produce anti VLA-4-antibodies, hybridoma cells that tested positive in such screening assays are cultured in a nutrient medium under conditions and for a time sufficient to allow the hybridoma cells to secrete the monoclonal antibodies into the culture medium. Tissue culture techniques and culture media suitable for hybridoma cells are well known. The conditioned hybridoma culture supernatant may be collected and the anti-VLA-4 antibodies optionally further purified by well-known methods.

Alternatively, the desired antibody may be produced by injecting the hybridoma cells into the peritoneal cavity of an unimmunized mouse. The hybridoma cells proliferate in the peritoneal cavity, secreting the antibody which accumulates as ascites fluid. The antibody may be harvested by withdrawing the ascites fluid from the peritoneal cavity with a syringe.

Several anti-VLA-4 monoclonal antibodies have been previously described (see, e.g., Sanchez-Madrid et al., 1986

[55]; Hemler et al., 1987 [39]; Pulido et al., 1991 [54]). HP1/2, for example, is one such murine monoclonal antibody which recognizes VLA-4. VLA-4 acts as a leukocyte receptor for plasma fibronectin and VCAM-1. Other monoclonal antibodies, such as HP2/1, HP2/4, L25 and P4C2, have been described that also recognize VLA-4.

Recombinant antibodies have been constructed and are described herein in which the CDRs of the variable domains of both heavy and light chains were derived from the murine HP1/2 sequence. Preferred starting materials for constructing recombinant humanized antibodies according to the present invention are anti-VLA-4 antibodies, such as HP1/2, that block the interaction of VLA-4 with both VCAM1 and fibronectin. Particularly preferred are those antibodies, such as HP1/2, which in addition, do not cause cell aggregation. Some anti-VLA-4 blocking antibodies have been observed to cause such aggregation. The HP1/2 MAb (Sanchez-Madrid et al., 1986 [55]) is a particularly excellent candidate for humanization since it has an extremely high potency, blocks VLA-4 interaction with both VCAM1 and fibronectin, but does not cause cell aggregation, and has the specificity for epitope B on VLA-4. In the initial experiments, $V_H$ and $V_K$ DNA were isolated and cloned from an HP1/2-producing hybridoma cell line. The variable domain frameworks and constant domains for humanization were initially derived from human antibody sequences.

The three CDRs that lie on both heavy and light chains are composed of those residues which structural studies have shown to be involved in antigen binding. Theoretically, if the CDRs of the murine HP1/2 antibody were grafted onto human frameworks to form a CDR-grafted variable domain, and this variable domain were attached to human constant domains, the resulting CDR-grafted antibody would essentially be a human antibody with the specificity of murine HP1/2 to bind human VLA-4. Given the highly "human" nature of this antibody, it would be expected to be far less immunogenic than murine HP1/2 when administered to patients.

However, following testing for antigen binding of a CDR-grafted HP1/2 antibody in which only the CDRs were grafted onto the human framework, it was shown that this did not produce a CDR-grafted antibody having reasonable affinity for the VLA-4 antigen. It was therefore decided that additional residues adjacent to some of the CDRs and critical framework residues needed to be substituted from the human to the corresponding murine HP1/2 residues in order to generate an antibody with binding affinity in the range of 10% to 100% of the binding affinity of the murine HP1/2 MAb. Empirically, changes of one or more residues in the framework regions of $V_H$ and $V_K$ were made to prepare antibodies of the desired specificity and potency, but without making so many changes in the human framework so as to compromise the essentially human nature of the humanized $V_H$ and $V_K$ region sequences.

Furthermore, VLA-4-binding fragments may be prepared from the recombinant anti-VLA-4 antibodies described herein, such as Fab, Fab', $F(ab')_2$, and F(v) fragments; heavy chain monomers or dimers; light chain monomers or dimers; and dimers consisting of one heavy chain and one light chain are also contemplated herein. Such antibody fragments may be produced by chemical methods, e.g., by cleaving an intact antibody with a protease, such as pepsin or papain, or via recombinant DNA techniques, e.g., by using host cells transformed with truncated heavy and/or light chain genes. Heavy and light chain monomers may similarly be produced by treating an intact antibody with a reducing agent such as dithiothreitol or β-mercaptoethanol or by using host cells transformed with DNA encoding either the desired heavy chain or light chain or both.

The following examples are intended to further illustrate certain preferred embodiments of the invention and are not intended to be limiting in nature. In the following examples, the necessary restriction enzymes, plasmids, and other reagents and materials may be obtained from commercial sources and cloning, ligation and other recombinant DNA methodology may be performed by procedures well-known in the art.

EXAMPLE 1

Isolation of DNA Sequences Encoding

Murine Anti-VLA-4 Variable Regions

A. Isolation of the HP1/2 Heavy and Light Chain cDNA

To design a humanized recombinant antibody with specificity for VLA-4, it was first necessary to determine the sequence of the variable domain of the murine HP1/2 heavy and light chains. The sequence was determined from heavy and light chain cDNA that had been synthesized from cytoplasmic RNA according to methods referenced in Tempest et al., 1991 [5].

1. Cells and RNA Isolation

Cytoplasmic RNA (~200 µg) was prepared by the method of Favaloro et al., 1980 [63], from a semi-confluent 150 cm2 flask of HP1/2-producing hybridoma cells (about 5×105 logarithmic phase cells). The cells were pelleted and the supernatant was assayed for the presence of antibody by a solid phase ELISA using an Inno-Lia mouse monoclonal antibody isotyping kit (Innogenetics, Antwerp, Belgium) using both the kappa conjugate and the lambda conjugate. The antibody was confirmed to be $IgG1/_K$ by this method.

2. cDNA Synthesis cDNAs were synthesized from the HP1/2 RNA via reverse transcription initiated from primers based on the 5' end of either the murine IgG1 $CH_1$ or the murine kappa constant domains using approximately 5 µg RNA and 25 pmol primer in reverse transcriptase buffer containing 1µ 1/50 µl Pharmacia (Milton Keynes, United Kingdom) RNA Guard™ and 250 micromolar dNTPs. The sequence of these primers, CG1FOR and CK2FOR are shown as SEQ ID NO: 1 and SEQ ID NO: 2, respectively. The mixture was heated to 70° C., then allowed to cool slowly to room temperature. Then, 100 units/50 µl MMLV reverse transcriptase (Life Technologies, Paisley, United Kingdom) was added and the reaction was allowed to proceed at 42° C. for one hour.

3. Amplification of $V_H$ and $V_K$ cDNA

Polymerase chain reaction (PCR) of murine MAb variable regions can be achieved using a variety of procedures, for example, anchored PCR or primers based on conserved sequences (see, e.g., Orlandi et al., 1989 [64]). Orlandi et al. [64], Huse et al., 1989 [65] and Jones and Bendig, 1991 [66], have described some variable region primers. We have been unsuccessful, however, in using a number of such primers, particularly those for the light chain PCR of HP1/2 derived $V_K$ sequences.

HP1/2 Ig $V_H$ and $V_K$ cDNAs were amplified by PCR as described by Saiki et al., 1988 [67] and Orlandi et al., 1989 [64]. Reactions were carried out using 2.5 units/50 ul Amplitaq™ polymerase (Perkin Elmer Cetus, Norwalk, Conn.) in 25 cycles of 94° C. for 30 seconds followed by 55° C. for 30 seconds and 75° C. for 45 seconds. The final cycle was followed by five minute incubation at 75° C. The same 3' oligonucleotides used for cDNA synthesis were used in conjunction with appropriate 5' oligonucleotides based on consensus sequences of relatively conserved regions at the 5' end of each V region. $V_H$ cDNA was successfully amplified using the primers VH1BACK [SEQ ID NO: 3] and CG1FOR [SEQ ID NO: 1] and yielded an amplification product of approximately 400 bp. $V_K$ cDNA was successfully amplified using the primers VK5BACK [SEQ ID NO: 4] and CK2FOR [SEQ ID NO: 2] and yielded an amplification product of approximately 380 bp.

4. Cloning and Sequencing $V_H$ DNA

The primers used for the amplification of $V_H$ DNA, contain the restriction enzyme sites PstI and HindIII which facilitate cloning into sequencing vectors. The general cloning and ligation methodology was as described in *Molecular Cloning A Laboratory Manual* 1982, [68]. The amplified DNA was digested with PstI to check for internal PstI sites and an internal PstI site was found. Therefore, the VH DNA was cloned as PstI-PstI and PstI-HindIII fragments into M13 mp18 and 19. The resulting collection of clones from two independent cDNA preparations were sequenced by the dideoxy method (Sanger, et al., 1977, [69] using Sequenase™ (United States Biochemicals, Cleveland, Ohio, USA). The sequence of a region of –100-250 bp was determined from each of 25 clones. Out of more than 4000 nucleotides sequenced, there were three PCR-induced transition mutation in three separate clones. The HP1/2 $V_H$ DNA sequence and its translated amino acid sequence are set forth in SEQ ID NO: 5 and SEQ ID NO: 6, respectively. It should be noted that the first eight amino acids are dictated by the 5' primer used in the PCR. Computer-assisted comparisons indicate that HP1/2 VH [SEQ ID NOS: 5 and 6] is a member of family IIC (Kabat et al., 1991, [15]. A comparison between HP1/2 $V_H$ [SEQ ID NOS: 5 and 6] and a consensus sequence of family IIC revealed that the only unusual residues are at amino acid positions 80, 98 and 121 (79, 94 and 121 in Kabat numbering). Although Tyr 80 is invariant in subgroup IIC other sequenced murine VH regions have other aromatic amino acids at this position although none have Trp. The majority of human and murine VHs have an arginine residue at Kabat position 94. The presence of Asp 94 in HP1/2 $V_H$ is extremely rare; there is only one reported example of a negatively charged residue at this position. Proline at Kabat position 113 is also unusual but is unlikely to be important in the conformation of the CDRs because of its distance from them. The amino acids making up CDR1 have been found in three other sequenced murine $V_H$ regions. However, CDR2 and CDR3 are unique to HP1/2 and are not found in any other reported murine $V_H$.

5. Cloning and Sequencing $V_K$ DNA

The primers used for the amplification of VK DNA contain restriction sites for the enzymes EcoRI and HindIII. The PCR products obtained using primers VK1BACK [SEQ ID NO: 7], VK5BACK [SEQ ID NO: 4] and VK7BACK [SEQ ID NO: 8] were purified and cloned into M13. Authentic kappa sequences were obtained only with VK5BACK [SEQ ID NO: 4]. The sequence of a region of ~200-350 bp was determined by the dideoxy method (Sanger et al., 1977, [69] using Sequenase™ (United States Biochemicals, Cleveland, Ohio, USA) from each of ten clones from two independent cDNA preparations. Out of more than 2 kb sequenced, there were only two clones which each contained one PCR-induced transition mutation.

The HP1/2 $V_K$ DNA sequence and its translated amino acid sequence are set forth in SEQ ID NO: 9 and SEQ ID NO: 10, respectively. The first four amino acids are dictated by the 5' PCR primer but the rest of the sequence is in total agreement with partial protein sequence data. HP1/2 $V_K$ is a member of Kabat family V (Kabat et al., 1991 [15]) and has no unusual residues. The amino acids of CDR1 and CDR3 are unique. The amino acids making up CDR2 have been reported in one other murine $V_K$.

EXAMPLE 2

Design of a CDR-Grafted Anti-VLA-4 Antibody

To design a CDR-grafted anti-VLA-4 antibody, it was necessary to determine which residues of murine HP1/2 comprise the CDRs of the light and heavy chains.

Three regions of hypervariability amid the less variable framework sequences are found on both light and heavy chains (Wu and Kabat, 1970 [16]; Kabat et al., 1991 [15]). In most cases these hypervariable regions correspond to, but may extend beyond, the CDR. The amino acid sequences of the murine HP1/2 $V_H$ and $V_K$ chains are set forth in SEQ ID NO: 6 and SEQ ID NO: 10, respectively. CDRs of murine HP1/2 were elucidated in accordance with Kabat et al., 1991 [15] by alignment with other $V_H$ and $V_K$ sequences. The CDRs of murine HP1/2 $V_H$ were identified and correspond to the residues identified in the humanized $V_H$ sequences disclosed herein as follows:

| CDR1 | $AA_{31}$-$AA_{35}$ |
|---|---|
| CDR2 | $AA_{50}$-$AA_{66}$ |
| CDR3 | $AA_{99}$-$AA_{110}$ |

These correspond to $AA_{31}$-$AA_{35}$, $AA_{50}$-$AA_{65}$, and $AA_{95}$-$AA_{102}$, respectively, in Kabat numbering. The CDRs of murine HP1/2 $V_K$ were identified and correspond to the residues identified in the humanized $V_K$ sequences disclosed herein as follows:

| CDR1 | $AA_{24}$-$AA_{34}$ |
|---|---|
| CDR2 | $AA_{50}$-$AA_{56}$ |
| CDR3 | $AA_{89}$-$AA_{97}$ |

These correspond to the same numbered amino acids in Kabat numbering. Thus, only the boundaries of the $V_K$, but not $V_H$, CDRs corresponded to the Kabat CDR residues. The human frameworks chosen to accept the HP1/2 CDRs were NEWM and REI for the heavy and light chains respectively. The NEWM and the REI sequences have been published in Kabat et al., 1991 [15].

An initial stage of the humanization process may comprise the basic CDR grafting with a minimal framework change that might be predicted from the literature. For example, in Riechmann et al., 1988 [4], the MAb CAMPATH-1H was successfully humanized using direct CDR grafting with only one framework change necessary to obtain an antibody with a binding efficiency similar to that of the original murine antibody. This framework change was the substitution of a Phe for a Ser at position 27. However, using the same humanization strategy by CDR grafting and the single framework change discovered by Riechmann et al., 1988 [4] for the preparation of humanized antibodies having other specificities did not yield antibodies with affinities comparable to the murine antibodies from which they were derived. In such cases, the humanization process must necessarily include additional empirical changes to achieve the desired specificity and potency. Such changes may be related to the unique structure and sequence of the starting murine antibody but are not predictable based upon other antibodies of different specificity and sequence. For example, analysis of the murine $V_H$ amino acid sequence from HP1/2 as set forth in SEQ ID NO: 6 as compared with the other known sequences indicated that residues 79, 94 and 113 (Kabat numbering) were unusual. Of these, only Asp 94 is likely to be important in CDR conformation. Most $V_H$ regions that have been sequenced have an arginine at this position which is able to form a salt bridge with a relatively conserved Asp 101 in CDR3. Because NEWM has an Arg 94 and $V_H$ CDR3 of HP1/2 has an Asp 101, there remains the possibility that a salt bridge would form which would not normally occur. The presence of a negatively charged residue at position 94 is very unusual and therefore it was decided to include the Asp 94 into the putative humanized $V_H$.

A chimeric (murine V/human IgG1/$_K$) HP1/2 antibody may be useful, but not a necessary, intermediate in the initial stages of preparing a CDR grafted construct because (i) its antigen-binding ability may indicate that the correct V regions have been cloned; and (ii) it may act as a useful control in assays of the various humanized antibodies prepared in accordance with the present invention.

For $V_H$, an M13 clone containing full-length HP1/2 $V_H$ was amplified using VH1BACK [SEQ ID NO: 3] and VH1FOR [SEQ ID NO: 11] which contain PstI and BstEII sites respectively at the 5' and 3' ends of the $V_H$ domain. The amplified DNA was cut with BstEII and partially cut with PstI, full-length DNA purified and cloned into M13VHPCR1 (Orlandi et al., 1989 [64]) which had been cut with PstI and BstEII. For $V_K$ an M13 clone containing full-length HP1/2 $V_K$ was amplified using VK3BACK [SEQ ID NO: 12] and VK1FOR [SEQ ID NO: 13] to introduce PvuII and BglII sites respectively at the 5' and 3' ends of the $V_K$ domain. The amplified DNA was cut with PvuII and BglII and cloned into M13VKPCR1 (Orlandi et al., 1989 [64]) which had been cut with PvuII and BclII.

In sum, the 5' primers used for the amplification of the murine $V_H$ and $V_K$ regions contain convenient restriction sites for cloning into our expression vectors. The 3' primers used in the PCRs were from the constant regions. Restriction sites at the 3' end of the variable region genes were introduced into cloned murine variable region genes with PCR primers which introduced BstII or BglII sites in the heavy and light (kappa) variable regions, respectively. Additionally, the $V_H$ primer changed Pro 113 to Ser.

The murine $V_H$ and $V_K$ DNAs were cloned into vectors containing the gpt and hygromycin resistance genes respectively, such as pSVgpt and pSVhyg as described by Orlandi, et al. [64], and appropriate human IgG1, IgG4 or $_K$ constant regions were added, for example, as described by Takahashi et al., 1982 [70], Flanagan and Rabbitts, 1982 [71], and Hieter et al., 1980 [72], respectively. The vectors were cotransfected into the rat myeloma YB2/0 and mycophenolic acid resistant clones screened by ELISA for secretion of chimeric IgG/$_K$ antibody. The YB2/0 cell line was described by Kilmartin et al., 1982 [73] and is available from the American Type Culture Collection (ATCC, Rockville, Md.). ELISA positive clones were expanded and antibody purified from culture medium by protein A affinity chromatography. The chimeric antibody purified from the transfected cells was assayed for anti-VLA-4 antibody activity as described in Example 7 and was found to be equipotent with the murine HP1/2 antibody.

EXAMPLE 3

Transplantation of CDR Sequences and Mutagenesis of Selected Framework Residues

Transplantation of the CDRs into human frameworks was performed using M13 mutagenesis vectors. The human frameworks chosen to accept the CDR sequences outlined in Example 2 were derived from NEWM for $V_H$ and REI for $V_K$, each in an M13 mutagenesis vector. The M13 mutagenesis vectors used for $V_H$ and $V_K$, were M13VHPCR1 and M13VKPCR2, respectively. M13VKPCR2 is identical to M13VKPCR1 as described by Orlandi et al., 1989 [64], except for a single amino acid change from valine (GTG) to glutamine (GAA) in framework 4 of the REI $V_K$ coding sequence. M13VHPCR1 described by Orlandi et al., 1989 [64] is M13 that contains the coding sequence for a $V_H$ region that is an NEWM framework sequence with CDRs derived from an anti-hapten (4-hydroxy-3-nitrophenyl acetyl caproic acid) antibody; the irrelevant $V_H$ CDRs are replaced by site-directed mutagenesis with the CDRs derived from HP1/2 $V_H$ as described below. The $V_H$ region sequence (DNA and amino acid) encoded by M13VHPCR1 is shown as SEQ ID NOS: 14 and 15. M13VKPCR2, like M13VKPCR1 described by Orlandi et al. [64], is M13 that contains the coding sequence for a $V_K$ region that is N-terminal modified REI framework sequence with CDRs derived from an anti-lysozyme antibody; these irrelevant $V_K$ CDRs are replaced by site-directed mutagenesis with the CDRs derived from HP1/2 $V_K$ as described below. The $V_K$ region sequence (DNA and amino acid) encoded by M13PCR2 is shown as SEQ ID NOS: 16 and 17.

Synthetic oligonucleotides were synthesized containing the HP1/2-derived $V_H$ and VK CDRs flanked by short sequences drawn from NEWM and REI frameworks, respectively, and grafted into the human frameworks by oligonucleotide site-directed mutagenesis as follows. For CDR grafting into the human $V_H$ framework, mutagenizing oligonucleotides 598 [SEQ ID NO: 18], 599 [SEQ ID NO: 19] and 600 [SEQ ID NO: 20] were used. For CDR grafting into the human $V_K$ framework, the mutagenizing oligonucleotides were 605 [SEQ ID NO: 21], 606 [SEQ ID NO: 22] and 607 [SEQ ID NO: 23]. To 5 µg of $V_H$ or $V_K$ single-stranded DNA in M13 was added a 2-fold molar excess of each of the three $V_H$ or $V_K$ phosphorylated oligonucleotides together with flanking primers based on M13 sequences, oligo 10 [SEQ ID NO: 24] for $V_H$ and oligo 385 [SEQ ID NO: 25] for $V_K$. Primers were annealed to the template by heating to 70° C. and slowly cooling to 37° C. The annealed DNA was extended and ligated with 2.5 U T7 DNA polymerase (United States Biochemicals) and 1 U T4 DNA ligase (Life Technologies) in 10 mM Tris HCl pH 8.0, 5 mM $MgCl_2$, 10 mM DTT, 1 mM ATP, 250 µM dNTPs in a reaction volume of 50 µl at 16° C. for 1-2 hours.

The newly extended mutagenic strand was preferentially amplified using 1 U Vent DNA polymerase (New England Biolabs) and 25 pmol oligo 11 [SEQ ID NO: 26] or oligo 391 [SEQ ID NO: 27] (for $V_H$ or $V_K$, respectively) in 10 mM KCl, 10 mM $(NH_4)_2SO_4$, 20 mM Tris HCl pH 8.8, 2 mM $MgSO_4$, 0.1% Triton X-100, 25 µM dNTPs in a reaction volume of 50 µl and subjecting the sample to 30 cycles of 94°, 30 s; 50°, 30 s; 75°, 90 s.

A normal PCR was then performed by adding 25 pmol oligo 10 [SEQ ID NO: 24] (for $V_H$) or oligo 385 [SEQ ID NO: 25] (for $V_K$) with 10 thermal cycles. The product DNAs were digested with HindIII and BamHI and cloned into M13 mp19.

Single-stranded DNA was prepared from individual plaques, sequenced and triple mutants were identified.

The resulting Stage 1 $V_H$ construct with the DNA sequence and its translated product set forth in SEQ ID NO: 28 and SEQ ID NO: 29, respectively. In addition to the CDR grafting, the Stage 1 $V_H$ construct contained selected framework changes. Just prior to CDR1, a block of sequences was changed to the murine residues Phe 27, Asn 28, Ile 29 and Lys 30 [compare $AA_{27}$-$AA_{30}$ of SEQ ID NO: 29 with that of murine $V_H$ sequence [SEQ ID NO: 6]]. This included Phe-27 as substituted in the humanization of the rat CAMPATH1-H antibody (Riechmann et al., 1988 [4]), but then also substitutes the next three residues found in the murine sequence. Although these four residues are not nominally included in CDR1 (i.e., are not hypervariable in the Kabat sense), structurally they are a part of the CDR1 loop (i.e., structural loop residues), and therefore included empirically as part of CDR1. In addition, the change from Arg to Asp at residue 94 was made based on the rationale discussed in Example 2. An alignment of the CDR-grafted Stage 1 framework sequences as compared with the NEWM framework is shown in Table I. The resulting VK1 (DQL) construct with the DNA sequence and its translated product are set forth in SEQ ID NO: 30 and SEQ ID NO: 31, respectively. An alignment of the CDR-grafted VK1 (DQL) framework sequences as compared with the REI framework is shown in Table II.

The CDR replaced $V_H$ (Stage 1) and $V_K$ (VK1) genes were cloned in expression vectors according to Orlandi, et al., 1989 [64] to yield the plasmids termed pHuVHHuIgG1, pHuVH-HuIgG4 and pHuVKHuCK. For pHuVHHuIgG1 and pHuVHHuIgG4, the Stage 1 $V_H$ gene together with the Ig heavy chain promoter, appropriate splice sites and signal peptide sequences were excised from the M13 mutagenesis vector by digestion with HindIII and BamHI, and cloned into an expression vector such as pSVgpt as described by Orlandi et al. [64], containing the murine Ig heavy chain enhancer, the SV40 promoter, the gpt gene for selection in mammalian cells and genes for replication and selection in E. coli. A human IgG1 constant region as described in Takahashi et al., 1982 [70] was then added as a BamHI fragment. Alternatively, a human IgG4 construct region as described by Flanagan and Rabbitts, 1982 [71] is added. The construction of the pHuVKHuCK plasmid, using an expression vector such as pSVhyg as described by Orlandi et al. [64], was essentially the same as that of the heavy chain expression vector except that the gpt gene for selection was replaced by the hygromycin resistance gene (hyg) and a human kappa chain constant region as described by Hieter, 1980, [72] was added. The vectors were cotransfected into the rat myeloma YB2/0 and mycophenolic acid resistant clones screened by ELISA for secretion of human IgG/$_K$ antibody. The YB2/0 cell line was described by Kilmartin et al., 1982 [73] and is available from the American Type Culture Collection (ATCC, Rockville, Md.). ELISA positive clones were expanded and antibody purified from culture medium by protein A affinity chromatography. The transfected cells are assayed for anti-VLA-4 antibody activity as described in Example 7.

EXAMPLE 4

Modification of a CDR Grafted Antibody

Beyond the stages of design and preparation to yield anti-VLA-4 antibodies as described above in Examples 2 and 3, additional stages of empirical modifications were used to successfully prepare humanized recombinant anti-VLA-4 antibodies. The Stage 1 modifications as described in Example 3 were based on our analysis of primary sequence and experience in attempting to successfully humanize antibodies. The next modifications, designated as Stage 2, were empirical, based in part on our analysis of 3D modelling data. For the $V_H$ region, further modifications, designated Stage 3, were so-called "scanning" modifications empirically made to correct any remaining defects in affinities or other antibody properties. The modifications that were made in these several stages were empirical changes of various blocks of amino acids with the goal of optimizing the affinity and other desired properties of humanized anti-VLA-4 antibodies. Not every modification made during the various stages resulted in antibodies with desired properties.

1. Additional Heavy Chain Modifications a. Stage 2 Modification

An additional empirical change in the $V_H$ framework was made with the use of computer modelling, to generate a Stage 2 construct with the DNA sequence and its translated product set forth in SEQ ID NO: 32 and SEQ ID NO: 33, respectively. Using computer modelling of the Stage 1 $V_H$ region, we determined to make a single change in the framework for Stage 2, namely a substitution of a Ser for Lys at position 75 (Kabat numbering), that is position 76 in SEQ ID NO: 33. This determination was in part based on the possibility that Lys-75 might project into CDR1 and alter its conformation. The M13 vector containing the Stage 1 CDR grafted HuVH, as described in Example 3, was used as template for two-step PCR-directed mutagenesis using the overlap/extension method as described by Ho et al., 1989 [74]. In the first step, two separate PCRs were set up, one with an end primer, oligo 10, [SEQ ID NO: 24] and a primer containing the desired mutation, 684 [SEQ ID NO: 34], and the other with the opposite end primer, oligo 11 [SEQ ID NO: 26], and a primer, 683 [SEQ ID NO: 35], that is complementary to the first mutagenic primer. The amplification products of this first pair of PCRs were then mixed together and a second PCR step was carried out using only the end primers oligos 10 and 11, SEQ ID NO: 24 and SEQ ID NO: 26, respectively. The mutagenized amplification product of this PCR was then cloned into M13 mp19 and sequenced, and a mutant bearing the Lys to Ser change (Stage 2 or "S mutant") was identified.

This turned out to be a critical change in the humanized heavy chain derived from HP1/2 (see Example 7). However, this critical change in the preparation of humanized recombinant anti-VLA-4 antibodies according to the present invention was not similarly critical in the preparation of other humanized antibodies. Specifically, using the same rationalization and analysis as outlined above, a change in that position was not found to be a beneficial change in the humanization of antibodies of 2 different specificities. An alignment of the CDR-grafted Stage 2 framework sequences as compared with the NEWM, as well as Stage 1 sequences, is shown in Table I.

b. Stage 3 Modifications

Additional empirical changes were made as Stage 3 constructs. In Stage 3, a series of 5 different block changes of amino acids, for largely empirical reasons, were made to try to improve potency. These constructs are designated STAW, KAITAS, SSE, KRS, and AS. All contain the position 75 Ser (Kabat numbering) changed in Stage 2 [position 76 of SEQ ID NO: 35], with other changes as noted. Each of these constructs was prepared by two-step PCR directed mutagenesis using the overlap/extension method of Ho et al., 1989 [74], as described for the Stage 2 Ser mutant, above. For STAW, the additional changes were Gln to Thr at position 77, Phe to Ala at position 78 and Ser to Trp at position 79 (Kabat numbering). These changes were accomplished using end primers, oligos 10 [SEQ ID NO: 24] and 11 [SEQ ID NO: 26] in conjunction with mutagenizing primers 713 [SEQ ID NO: 36] and 716 [SEQ ID NO: 37]. The STAW $V_H$ DNA sequence and its translated amino acid sequence are set forth in SEQ ID NO: 38 and SEQ ID NO: 39, respectively. KAITAS was prepared with additional changes of Arg to Lys (position 66), Val to Ala (67), Met to Ile (69), Leu to Thr (70) and Val to Ala (71) (Kabat numbering), using oligos 10 [SEQ ID NO: 24] and 11 [SEQ ID NO: 26] in conjunction with oligos 706 [SEQ ID NO: 40] and 707 [SEQ ID NO: 41]. The KAITAS $V_H$ DNA sequence and its translated amino acid sequence are set forth in SEQ ID NO: 42 and SEQ ID NO: 43, respectively. SSE had additional changes of Ala to Ser (84) and Ala to Glu (85) (Kabat numbering), effected by oligos 10 and 11 with oligos 768 [SEQ ID NO: 44] and 769 [SEQ ID NO: 45]. The SSE $V_H$ DNA sequence and its translated amino acid sequence are set forth in SEQ ID NO: 46 and SEQ ID NO: 47, respectively. KRS had additional changes of Arg to Lys (38) and Pro to Arg (40) (Kabat numbering), from oligos 10 [SEQ ID NO: 24] and 11 [SEQ ID NO: 26] with oligos 704 [SEQ ID NO: 48] and 705 [SEQ ID NO: 49]. The KRS $V_H$ DNA sequence and its translated amino acid sequence are set forth in SEQ ID NO: 50 and SEQ ID NO: 51, respectively. AS had additional change Val to Ala at position 24 (Kabat numbering) from oligos 10 [SEQ ID NO: 24] and 11 [SEQ ID NO: 26] with oligos 745 [SEQ ID NO: 52] and 746 [SEQ ID NO: 53]. The AS $V_H$ DNA sequence and its translated amino acid sequence are set forth in SEQ ID NO: 54 and SEQ ID NO: 55, respectively. An alignment of the CDR-grafted Stage 3 framework sequences with the NEWM, Stage 0 (see below), Stage 1, and Stage 2 sequences is shown in Table I. Importantly, as shown in Example 7, the potency of STAW and AS humanized antibodies were improved, while KAITAS and KRS humanized antibodies were not of better potency. This could not be predicted.

c. Reverse (Stage 0) Modifications

The two blocks of changes made to generate Stage 1 at positions 28-30 (NIK) and 94 (D) were mutated back to the NEWM sequences at positions 28-30 (TFS), 94 (R), or both positions 27-30 (TFS) and 94 (R). These constructs were designated Stage 0-A, 0-B and 0-C, respectively. Each of these constructs was prepared by two-step PCR directed mutagenesis using the overlap/extension method of Ho et al., 1989 [74], as described for the Stage 2 Ser mutant, above. Stage 0-A and 0-B were generated from Stage 1; Stage 0-C was generated from Stage 0-A, as follows. For Stage 0-A, the change was from Asp to Arg at position 94. This change was accomplished using end primers, oligos 10 [SEQ ID NO: 24] and 11 [SEQ ID NO: 26] in conjunction with mutagenizing primers 915 [SEQ ID NO: 56] and 917 [SEQ ID NO: 57]. For stage 0-B, the changes were from Asn-Ile-Lys to Thr-Phe-Ser at positions 28-30. These changes were accomplished by using end primers 10 [SEQ ID NO: 24] and 11 [SEQ ID NO: 26] in conjunction with mutagenizing primers 918 [SEQ ID NO: 58] and 919 [SEQ ID NO: 59]. Finally, for stage 0-C, to the change of Asp to Arg at position 94 in Stage 0-A were added the changes were from Asn-Ile-Lys to Thr-Phe-Ser at positions 28-30. These changes were accomplished with the same end primers and mutagenizing primers described above for the Stage 0-B construct.

TABLE I

HEAVY CHAIN SEQUENCES

FR1

| | |
|---|---|
| NEWM (SEQ ID NO: 105) | ?VQLXXSGPGLVRPSQTLSLTCTVSGSTFS |
| Humanized Anti-VLA-4: | |
| STAGE 0-A (residues 20-49 of SEQ ID N0: 29) | QVQLQE......................FNIK |
| STAGE 0-B (SEQ ID N0: 109) | QVQLQE.........................F....... |
| STAGE 0-C (SEQ ID NO: 109) | QVQLQE.........................F....... |
| STAGE 1 (residues 20-49 of SEQ ID N0: 29) | QVQLQE......................FNIK |
| STAGE 2 (residues 20-49 of SEQ ID N0: 33) | QVQLQE......................FNIK |
| STAGE 3 (STAW) (residues 20-49 of SEQ ID N0: 39) | QVQLQE......................FNIK |
| (KAITAS) (residues 20-49 of SEQ ID N0: 43) | QVQLQE......................FNIK |
| (SSE) (residues 1-30 of SEQ ID N0: 47) | QVQLQE......................FNIK |
| (KRS) (residues 20-49 of SEQ ID NO: 51) | QVQLQE......................FNIK |
| (AS) (residues 20-49 of SEQ ID NO: 55) | QVQLQE....................A.FNIK |

FR2

| | |
|---|---|
| NEWM | WVRQPPGRGLEWIG (SEQ ID NO: 106) |

TABLE I-continued

HEAVY CHAIN SEQUENCES

Humanized Anti-VLA-4:

STAGE 0-A ................... (SEQ ID NO: 106)

STAGE 0-B ................... (SEQ ID NO: 106)

STAGE 0-C ................... (SEQ ID NO: 106)

STAGE 1 ...................
(residues 55-68 of SEQ ID NO: 29)

STAGE 2 ...................
(residues 55-68 of SEQ ID NO: 33)

STAGE 3 (STAW) ...................
(residues 55-68 of SEQ ID NO: 39)

(KAITAS) ...................
(residues 55-68 of SEQ ID NO: 43)

(SSE) ...................
(residues 36-49 of SEQ ID NO: 47)

(KRS) ....K.R..........
(residues 55-68 of SEQ ID NO: 51)

(AS) ...................
(residues 55-68 of SEQ ID NO: 55)

---
FR3

NEWM                                RVTMLVDTSKNQFSLRLSSVTAADTAVYYCAR
(SEQ ID NO: 107)

Humanized Anti-VLA-4:

STAGE 0-A                           ...............................
(SEQ ID NO: 107)

STAGE 0-B                           ..............................D
(residues 86-117 OF SEQ ID NO: 29)

STAGE 0-C                           ..............................D
(residues 86-117 OF SEQ ID NO: 29)

STAGE 1                             ..............................D
(residues 86-117 OF SEQ ID NO: 29)

STAGE 2                             ........S.....................D
(residues 86-117 OF SEQ ID NO: 33)

STAGE 3 (STAW)                      ........S.TAW.................D
(residues 86-117 OF SEQ ID NO: 39)

(KAITAS)                            .KA.ITA.S.....................D
(residues 86-117 OF SEQ ID NO: 43)

(SSE)                               ........S........SE...........D
(residues 67-98 OF SEQ ID NO: 47)

(KRS)                               ........S.....................D
(residues 86-117 OF SEQ ID NO: 51)

(AS)                                ........S.....................D
(residues 86-117 OF SEQ ID NO: 55)

---
FR4

NEWM                                WGQGSLVTVSS (SEQ ID NO: 108)

Humanized Anti-VLA-4:

STAGE 0-A                           ...TT...... (residues 130-140 OF SEQ ID NO: 29)

STAGE 0-B                           ...TT...... (residues 130-140 OF SEQ ID NO: 29)

STAGE 0-C                           ...TT...... (residues 130-140 OF SEQ ID NO: 29)

TABLE I-continued

HEAVY CHAIN SEQUENCES

| STAGE 1 | ... TT ......... | (residues 130-140 OF SEQ ID NO: 29) |
|---|---|---|
| STAGE 2 | ... TT ......... | (residues 130-140 OF SEQ ID NO: 33) |
| STAGE 3 (STAW) | ... TT ......... | (residues 130-140 OF SEQ ID NO: 39) |
| (KAITAS) | ... TT ......... | (residues 130-140 OF SEQ ID NO: 43) |
| (SSE) | ... TT ......... | (residues 111-121 OF SEQ ID NO: 47) |
| (KRS) | ... TT ......... | (residues 130-140 OF SEQ ID NO: 51) |
| (AS) | ... TT ......... | (residues 130-140 OF SEQ ID NO: 55) |

Note:
X denotes Glx., ?denotes Q or E.

2. Light Chain Modifications

In our experience, the humanized light chain generally requires few, if any, modifications. However, in the preparation of humanized anti-VLA-4 antibodies, it became apparent that the light chain of HP1/2 did require several empirical changes. For example, humanized heavy chain of the Stage 2 construct (the Ser mutant) with murine light chain was about 2.5 fold lower potency than murine HP1/2, while the same humanized heavy chain with humanized light chain was about 4-fold lower potency. The Stage 1 humanized $V_K$ construct was designated VK1 (DQL) and the DNA sequence and its translated amino acid sequence are set forth in SEQ ID NO: 30 and SEQ ID NO: 31, respectively. The DQL mutations arose from the PCR primer used in the initial cloning of the $V_K$ region (see Example 1). Alterations were made in the light chain, generating two mutants, SVMDY and DQMDY (VK2 and VK3, respectively). The SVMDY mutant was prepared from the DQL sequence using oligos 10 [SEQ ID NO: 24] and 11 [SEQ ID NO: 26] for DY sequences with oligos 697 [SEQ ID NO: 60 and 698 [SEQ ID NO: 61] for SVM sequences. The VK2 (SVMDY) DNA sequence and its translated amino acid sequence are set forth in SEQ ID NO: 62 and SEQ ID NO: 63, respectively. The DQMDY sequences were restored to the original REI framework sequences by two-step PCR-directed mutagenesis using end primers 10 [SEQ ID NO: 24] and 11 [SEQ ID NO: 26] with mutagenic primers 803 [SEQ ID NO: 64] and 804 [SEQ ID NO: 65], and using the SVMDY sequence as template. The VK3 (DQMDY) DNA sequence and its translated amino acid sequence are set forth in SEQ ID NO: 66 and SEQ ID NO: 67, respectively. The change in the amino terminus (SVM versus DQM) is not relevant, and relates to the amino terminus of the murine light chain. The other two changes, D and Y, were made to improve potency, and did indeed do so as described in Example 7. An alignment of the CDR-grafted DQL (VK1), SVMDY (VK2) and DQMDY (VK3) framework sequences as compared with the REI sequence is shown in Table II.

When the AS mutant heavy chain was combined with the improved light chain (SVMDY), the resulting humanized antibody was equipotent with murine HP1/2 as shown in Table III.

3. Alternative Humanized $V_H$ and $V_K$ Regions

Alternatively, a humanized $V_H$ region sequence based on HP1/2 $V_H$ region [SEQ ID NO: 5] may be prepared. One such alternative is designated $V_H$-PDLN. The DNA sequence of PDLN $V_H$ and its translated amino acid sequence are set forth as SEQ ID NO: 68 and SEQ ID NO: 69, respectively.

In addition, an alternative humanized $V_K$ region sequence based on the HP1/2 $V_K$ region [SEQ ID NO: 9] may be prepared. One such alternative $V_K$ sequence is designated $V_K$-PDLN and its translated amino acid sequence are set forth as SEQ ID NO: 70 and SEQ ID NO: 71, respectively.

The humanized $V_H$-PDLN was prepared by ligating 12 oligonucleotides, which together span the entire humanized variable region, and by screening for constructs having the correct sequence. The protocol is described in more detail below.

Oligonucleotides 370-119 through 370-130 (SEQ ID NO: 72 through SEQ ID NO: 83, respectively) (20 pmoles each) were dried down, and separately resuspended in 20 μl 1× Kinase Buffer containing 1 mM ATP and 1 μl T4 polynucleotide kinase (10 U/μl). The kinase reaction mixture was incubated for 1 hour at 37° C. The reaction was terminated by incubating at 70° C. for 5 minutes.

The kinase-treated oligonucleotides were combined with each other (240 μl total) and ligated together with 26 μl 10 mM ATP and 2 μl T4 DNA ligase (10 U/μl), and the reaction mixture was incubated at room temperature for 6 hours. The ligation reaction mixture was extracted with phenol:chloroform (1:1) saturated with TE buffer, and then ethanol precipitated and washed 5 times with 70% ethanol.

The dried and washed ethanol precipitate was resuspended in 50 μl 1×150 mM Restriction Enzyme Buffer (10×150 mM Restriction Enzyme Buffer is 100 mM Tris-HCl, pH 8.0, 1.5 M NaCl, 100 mM $MgCl_2$, 1 mg/ml gelatin, 10 mM dithiothreitol) and incubated with restriction enzymes BstE2 and PstI for 16 hours at 37° C. The digestion products were electrophoresed through a 2% agarose gel, and the band corresponding to 330 bp was excised. The fragment was eluted using GENECLEAN II™ and the eluate was ethanol precipitated. The ethanol precipitate was resuspended in 20 μl TE buffer.

Next, the 330 bp fragment was ligated into vector pLCB7 which was prepared for ligation by digesting with PstI and BstE2, dephosphorylating the 5' ends with calf alkaline phosphatase, fractionating on a low melting temperature agarose (LMA) gel, and excising the pLCB7/PstI/BstE2 LMA fragment. The pLCB7 LMA fragment was then ligated to the 330 bp oligonucleotide fragment encoding the humanized $V_H$ region using T4 DNA ligase.

The ligation mixture was used to transform E. coli JA221 (Iq) to ampicillin resistance. Colonies were grown up and mini-prep DNA was prepared. The recombinant plasmids were screened for the presence of an approximately 413 bp NotI/BstE2 fragment. DNA sequence analysis identified vector pMDR1023 as having the designed humanized $V_H$-PDLN sequence.

The humanized $V_K$-PDLN was prepared by ligating 12 oligonucleotides, which together span the entire humanized $V_K$-PDLN variable region, and by screening for constructs having the correct sequence. The protocol is described in more detail below.

Oligonucleotides 370-131 through 370-142 (SEQ ID NO: 84 through SEQ ID NO: 95, respectively) (20 pmoles each) were dried down, and separately resuspended in 20 µl 1× Kinase Buffer containing 1 mM ATP and 1 µl T4 polynucleotide kinase (10 U/µl). The kinase reaction mixture was incubated for 1 hour at 37° C. The reaction was terminated by incubating at 70° C. for 5 minutes.

The kinase-treated oligonucleotides were combined with each other (240 µl total) and ligated together with 26 µl 10 mM ATP and 2 µl T4 DNA ligase (10 U/µl), and the reaction mixture was incubated at room temperature for 6 hours. The ligation reaction mixture was extracted with phenol:chloroform (1:1) saturated with TE buffer, and then ethanol precipitated and washed 5 times with 70% ethanol.

The dried and washed ethanol precipitate was resuspended in 40 µl TE, then electrophoresed through a 2% agarose gel, and the band corresponding to 380 bp was excised. The fragment was eluted using GENECLEAN II™ and the eluate was ethanol precipitated. The ethanol precipitate was resuspended in 20 µl TE buffer.

Next, the 380 bp fragment was ligated into vector pNN03, which was prepared for ligation by linearizing with HindIII and BamHI, dephosphorylating the 5' ends with calf alkaline phosphatase, fractionating on a low melting temperature agarose gel, and excising the band corresponding to linearized pNN03 (2.7 kb). The linearized, dephosphorylated pNN03 was then ligated to the 380 bp oligonucleotide fragment encoding the humanized $V_K$ region using T4 DNA ligase.

The ligation mixture was used to transform *E. coli* JA221 (Iq) to ampicillin resistance. Colonies were grown up and mini-prep DNA was prepared. The recombinant plasmids were screened for the presence of the variable region fragment. DNA sequence analysis identified vector pMDR1025 as having the designed humanized $V_K$-PDLN sequence.

When an antibody with a $V_H$-PDLN containing heavy chain and with a $V_K$-PDLN containing light chain was assayed for potency according to Example 7, the resulting humanized antibody was approximately equipotent with the murine HP1/2 antibody.

TABLE II

| LIGHT CHAIN SEQUENCES | |
|---|---|
| FR1 | |
| REI | DIQMTQSPSSLSASVGDRVTITC (SEQ ID NO: 101) |
| Humanized Anti-VLA-4: | |
| Construct VK1 (DQL) (residues 20-42 of SEQ ID NO: 31) | .....L................. |
| Construct VK2 (SVMDY) (residues 20-42 of SEQ ID NO: 63) | S.VM................... |
| Construct VK3 (DQMDY) (residues 20-42 of SEQ ID NO: 67) | D.QM................... |
| FR2 | |
| REI | WYQQTPGKAPKLLIY (SEQ ID NO: 102) |
| Humanized Anti-VLA-4: | |
| VK1 (DQL) (residues 54-68 of SEQ ID NO: 31) | .........K............. |
| VK2 (SVMDY) (residues 54-68 of SEQ ID NO: 63) | .........K............. |
| VK3 (DQMDY) (residues 54-68 of SEQ ID NO: 67) | .........K............. |
| FR3 | |
| REI (SEQ ID NO: 103) | GVPSRFSGSGSGTDYTFTISSLQPEDIATYYC |
| Humanized Anti-VLA-4: | |
| VK1 (DQL) (residues 76-107 of SEQ ID NO: 31) | ...............................F............ |

TABLE II-continued

LIGHT CHAIN SEQUENCES

| | |
|---|---|
| VK2 (SVMDY) residues 76-107 of SEQ ID NO: 63) | ........D.........Y...................F............................ |
| VK3 (DQMDY) (residues 76-107 of SEQ ID NO: 67) | ........D.........Y...................F............................ |

FR4

| | |
|---|---|
| REI Humanized Anti-VLA-4: | FGQGTKLQIT (SEQ ID NO: 104) |
| VK1 (DQL) | ...............VE.K (residues 117-126 of SEQ ID NO: 31) |
| VK2 (SVMDY) | ...............VE.K (residues 117-126 of SEQ ID NO: 63) |
| VK3 (DQMDY) | ...............VE.K (residues 117-126 of SEQ ID NO: 67) |

EXAMPLE 5

Expression of Recombinant Anti-VLA-4 Antibodies

Each of the $V_H$ region sequences and $V_K$ region sequences prepared according to Examples 1-4, are transferred into expression vectors with constant region sequences, and the vectors are transfected, preferably via electroporation, into mammalian cells. The heavy and light chain sequences may be encoded on separate vectors and co-transfected into the cells or alternatively heavy and light chain sequences may be encoded by and transfected as a single vector. Such a single vector will contain 3 expression cassettes: one for Ig heavy chain, one for Ig light chain and one for a selection marker. Expression levels of antibody are measured following transfection, as described below, or as described in Example 7.

$V_H$ and $V_K$ region sequences as described in Example 4, were inserted into various cloning and expression vectors. For the anti-VLA-4 $V_H$ region sequences, plasmids containing such sequences [as described in Examples 1-4] were digested with PstI and BstE2. The plasmid DNA after digestion with PstI and BstE2, was dephosphorylated and electrophoresed through 2% agarose gel. The band for ligation was excised and the DNA elected using the GENECLEAN™ technique (Bio101, Inc., La Jolla, Calif.), ethanol precipitated and resuspended in 20 µl TE buffer (10 mM Tris-HCl, 1 mM Na₂ EDTA). Then, 10 µl of the resuspended DNA was used for ligation with the PstI/BstE2 digested $V_H$ region sequence.

The ligation mixture was used to transform *E. coli* K 12 JA221 (Iq) to ampicillin resistance. *E. coli* K12 JA221 (Iq) cells have been deposited with the ATCC (accession number 68845). Recombinant colonies were screened for the presence of the $V_H$ insert. Some of the plasmids containing such fragments were sequenced. The $V_H$-containing plasmids were designated pBAG 184 ($V_H$-STAW), pBAG 183 ($V_H$-KAITAS), pBAG 185 ($V_H$-KRS), pBAG 207 ($V_H$-SSE) and pBAG 195 ($V_H$-AS), and were deposited in *E. coli* K12 J221 (Iq) cells with the ATCC as accession nos. 69110, 69109, 69111, 69116 and 69113, respectively. The plasmid containing alternative $V_H$-PDLN region was designated pMDR1023.

For the $V_K$ region sequences, the DNA encoding these sequences were amplified for cloning and transformation using PCR. Prior to amplification, 20 pmoles of each of the $V_K$ chain primers were kinased by incubation with T4 polynucleotide kinase at 37° C. for 60 minutes by a conventional protocol. The kinase reactions were stopped by heating at 70° C. for 10 minutes.

The PCR reactions each contained 10 µl 10×PCR buffer (10×PCR buffer is 100 mM Tris/HCl, pH 8.3, 500 mM KCl, 15 mM MgCl₂, 0.01% gelatin, 20 pmoles each of the appropriate kinased primers, 20 µl cDNA, 0.5 µl Taq polymerase (5 U/µl, Perkin Elmer-Cetus) and 49.5 µl H₂O. The PCR conditions were 30 cycles of incubation for: 1 minute at 94° C.; 2 minutes at 40° C. (for heavy chain PCR) or at 55° C. (for light chain PCR); and 2 minutes at 72° C. For VK1-DQL, primers were 370-247 [SEQ ID NO: 96] and 370-210 [SEQ ID NO: 97]. For VK2-SVMDY, primers were 370-269 [SEQ ID NO: 98] and 370-210 [SEQ ID NO: 97]. For VK3-DQMDY, primers were 370-268 [SEQ ID NO: 99] and 370-210 [SEQ ID NO: 97].

The reaction mixtures were electrophoresed through 2% agarose gel, and the bands corresponding to the expected sizes of the light chain variable region (~330 bp) were excised with AgeI and BamHI. The DNA in those bands were eluted using the GENECLEAN™ technique (Bio101 Inc., La Jolla, Calif.), ethanol precipitated and subsequently each resuspended in 20 µl TE buffer (10 mM Tris-HCl, 1 mM Na₂EDTA).

Klenow fragment of DNA polymerase (New England Biolabs, 5 U/µl) (1 µl) was added to the purified PCR fragments in a reaction volume of 25 µl containing 1× ligation buffer (10× ligation buffer is 0.5 M Tris/HCl, pH 7.5, 100 mM MgCl2 and 40 mM DTT) and 0.125 mM each of dXTPs and the reaction incubated at room temperature for 15 minutes. The reaction was terminated by incubation at 70° C. for 5 minutes, and then stored on ice.

The fragment from each PCR reaction is ligated to a plasmid such as pNN03 or a plasmid derived from pNN03 such as pLCB7, which had been previously linearized by EcoRV, dephosphorylated and fractionated through low temperature melting agarose. Such plasmids, including pNN03 and pLCB7 have been described in co-pending and co-assigned (Burkly et al., U.S. Ser. No. 07/916,098, filed Jul. 24, 1992 [75]).

The ligation mixture was used to transform *E. coli* K12 JA221(Iq) to ampicillin resistance. *E. coli* K12 JA221(Iq) cells are deposited with American Type Culture Collection (accession number 68845). Recombinant colonies were screened for the presence of the $V_K$ insert. Some of the plasmids containing such fragments were sequenced. The $V_K$-containing plasmids were designated pBAG 190 (VK1-DQL), pBAG 198 (VK2-SVMDY) and pBAG 197 (VK3-DQMDY), and were deposited in *E. coli* K12 JA 221 (Iq) cells with the ATCC as accession nos. 69112, 69115 and 69114, respectively. The plasmid containing the alternative VK (PDLN) region was designated pMDR 1025.

In a series of experiments, the expression vectors encoding recombinant anti-VLA-4 heavy and light chains are transfected via electroporation and the cells are then cultured for 48 hours. After 48 hours of culture, the cells are radiolabelled using $^{35}$S-cysteine overnight and then the cell extracts and conditioned media are immunoprecipitated by incubation with protein A-Sepharose. The protein A-Sepharose is washed and the bound proteins are eluted with SDS-PAGE loading buffer. The samples are analyzed via electrophoresis through 10% SDS-PAGE gels under reducing conditions. In this way, light chain expression is detected only as a consequence of the light chains being associated with the heavy chains. The expected sizes of the heavy and light chains as visualized in the 10% gels are 50 kD and 25 kD, respectively.

Since recombinant anti-VLA-4 antibody molecules, prepared as described in Examples 1-4, may be stably expressed in a variety of mammalian cell lines, it is possible to express recombinant antibody genes in nonsecreting myeloma or hybridoma cell lines under the control of Ig-gene promoters and enhancers or in non-lymphoid cells, such as Chinese hamster ovary (CHO) cells, in conjunction with vector amplification using DHFR selection. Recently, Bebbington et al., 1992 [76] have described a method for the high-level expression of a recombinant antibody from myeloma cells using a glutamine synthetase gene as an amplifiable marker. This GS expression system is most preferred for the production of recombinant anti-VLA-4 antibody molecules according to the present invention. The methods, vectors with hCMV promoters and with 5' untranslated sequences from the hCMV-MIE genes including cell lines (most preferably NSO) and media for GS expression of recombinant antibodies is described in detail in Bebbington et al., 1992 [76], WO86/05807 [77], WO87/04462 [78], WO89/01036 [79] and WO89/10404 [80].

In accordance with the teachings of these publications, NSO cells were transfected with a heavy chain sequence having the VH-AS region sequence [SEQ ID NO: 54] and a light chain sequence having the VK-SVMDY sequence [SEQ ID NO: 66] to obtain a stable cell line secreting a humanized recombinant anti-VLA-4 antibody with high potency comparable to the murine HP1/2 antibody. This cell line has been deposited with the ATCC on Nov. 3, 1992 and given accession no. CRL 11175. The AS/SVMDY humanized antibody is at least equipotent with or perhaps more potent than the murine HP1/2 antibody.

EXAMPLE 6

Purification of MAbs from Conditioned Media for Assay

To obtain accurate values for half-maximal binding or inhibition, stock solutions of purified antibodies are needed at known concentrations. Stable cell lines secreting the antibodies of interest were made and the humanized recombinant anti-VLA-4 antibodies were purified from conditioned medium using conventional protein A chromatography. The concentration of the purified antibodies is assessed by their absorption coefficient at 280 nm, which is well established for antibodies.

A cell line producing a humanized anti-VLA-4 antibody is grown in roller bottles in Dulbecco's modified Eagle medium containing 10% fetal bovine serum. A 2 liter batch of conditioned medium is used for each purification run. Cells are removed from the medium by centrifugation in a RC-3B preparative centrifuge (4K, 30 minutes, H4000 rotor) and the supernatant is filtered first through a 0.45µ membrane and then through a 0.22µ membrane. The medium is stored at 4° C. until it can be processed.

Two liters of conditioned medium is concentrated to 220 ml in a spiral ultrafiltration unit (Amicon, Corp., Cherry Hill Drive, Danvers, Mass. 01923) that is equipped with an S1Y30 (YM30) Diaflo cartridge. The concentrate is diluted with 400 ml of protein A binding buffer (3M NaCl, 1.5M glycine pH 8.9) and again concentrated to 200 ml. The concentrate is treated in batch with 0.5 ml Fast Flow Protein A Sepharose 4 (Pharmacia, Inc., 800 Centennial Avenue, Piscataway, N.J. 08854) using a raised stir bar to agitate the mixture. After an overnight incubation at 4° C., the resin is collected by centrifugation (5 minutes, 50 g), washed twice with 20 volumes of protein A binding buffer (using centrifugation to recover the resin), and transferred to a column for subsequent treatment. The column is washed four times with 0.5 ml of protein A binding buffer, two times with 0.25 ml of PBS, and the IgG is eluted with Pierce IgG elution buffer (Pierce Chemical Co., Rockford, Ill. 61105 Cat No. 21004Y or 21009Y). 180 µl fractions are collected, which are neutralized with 20 µl of 1M HEPES pH 7.5. Fractions are analyzed for absorptance at 280 nm and by SDS-PAGE. The gel is stained with Coomassie blue. Peak fractions are pooled. 100 µl (14 ml/ml) is diluted with 100 µl of PBS and subjected to gel filtration on a Superose 6 FPLC column (Pharmacia, Inc., 800 Centennial Avenue, Piscataway, N.J. 08854) in PBS. The column is run at 20 ml/hour and 1.5 minute fractions are collected. Peak column fractions are pooled, aliquoted, frozen on dry ice, and stored at −70° C. SDS-polyacrylamide gel profile of the final product is obtained under reducing and non-reducing conditions. In some cases when the sample is analyzed under non-reducing conditions, about 10% of the product is not an intact antibody. Studies in these cases indicate that this product is a heavy-light chain dimer. This has been previously recognized as a problem with IgG4 antibodies.

EXAMPLE 7

Determination of Relative Binding Affinities of Humanized Recombinant Anti-VLA-4 Antibodies Recombinant antibodies according to the present invention are purified, as described in Example 6, and are assayed to determine their specificity for VLA-4 and their binding affinity or potency. In particular, the potency of a recombinant anti-VLA-4 antibody was assessed by calculating the half-maximal binding constant (reported as ng/ml or µg/ml of purified antibody) using two different assays described as follows.

1. Inhibition of VLA-4-dependent adhesion to VCAM1

The critical function of an anti-VLA-4 antibody is defined by the ability to inhibit the VCAM1/VLA-4 adhesion pathway. It has been previously shown (Lobb et al., 1991a, [81]) that purified recombinant soluble VCAM1 (rsVCAM1) can be immobilized on plastic and is a functional adhesion molecule. Immobilized rsVCAM1 binds VLA-4-expressing cells such as the human B cell line Ramos, and this binding can be inhibited by MAbs to VCAM1, such as 4B9 or MAbs to VLA-4, such as HP1/2. This assay provides a reproducible method to assess the potency of any humanized recombinant antibody. Briefly, the antibody solution is diluted, and the serial antibody dilutions are incubated with Ramos cells, which are then incubated with rsVCAM1-coated plates. The Ramos cells are fluorescently labelled as described by Lobb, 1991b [82], and binding assessed by fluorescence in 96 well cluster plates according to the following protocol.

Recombinant soluble VCAM1 was prepared and purified essentially as described by Lobb et al., 1991a [81]. Soluble VCAM is diluted to 10 µg/ml in 0.05 M $NaHCO_3$, (15 mM $NaHCO_3$, 35 mM $Na_2CO_3$) pH 9.2. Then 50 µl/well is added into a Linbro Titertek polystyrene 96 well plate, flat bottom, Flow Labs catalog #76-231-05. The plate is incubated at 4° C. overnight.

Following this incubation, the contents of the wells are removed by inverting and blotting the plate. To the empty wells, 100 µl/well of 1% of BSA in PBS, 0.02% $NaN_3$ added for 1 hour or longer at room temperature. If the plate is not to be used immediately, it can be blocked and stored for one week at 4° C. BSA is added to some wells to assess non-specific binding.

For binding quantitation, VLA-4 presenting cells, preferably Ramos cells, should be prelabelled. The cells may be radiolabelled or fluorescently labelled. For radiolabelling, prelabelling of the cells may be done overnight using $^3$H-thymidine (0.5 uCi/ml). Alternatively, and preferably, the cells are preincubated with BCECF-AM (chemical name: 2',7'-bis-(2-carboxyethyl)-5(and -6) carboxyfluorescein, acetoxymethyl ester, Molecular Probes Inc., Eugene, Oreg., catalog #B-1150). For this method, cells are suspended to $5 \times 10^6$/ml, 2 µM BCECF-AM is added and the mixture is incubated for 30 minutes at 37° C. Following either method, the cells are washed with RPMI, 2% FBS, pH 7.4. RPMI with 1% FBS may also be used.

For the binding study, $2-4 \times 10^6$ cells/ml in RPMI, 2% FBS are resuspended, then 50 µl of labelled cells are added per well for 10 minutes of binding at room temperature.

After the 10 minute incubation, the contents of the wells are removed by inversion and the plates washed 1-2 times gently with RPMI, 2% FBS. When examined under a light microscope, BSA blank wells should have very few cells bound. A brief inverted spin may be included to remove cells not firmly attached and the plates may be washed again 1-2 times.

For the BCECF-AM method, 100 µl of 1% NP40 is added to each well to solubilize the cells and then the plate is read on a fluorescence plate scanner. (If the radiolabelling method is used, 100 µl of 0.1% NaOH is added to each well and then the contents of each well are transferred to scintillation vials containing cocktail).

A volume of 50 µl of labelled cells should be counted to obtain a total known value added to each well. Then the 50 µl of labelled cells are added to either a well containing only 100 µl of 1% NP40 or to a scintillation vial depending on the method used.

For antibody blocking studies, 100 µl/well of murine HP1/2 MAb (anti-VLA-4) typically at 10 µg/ml in RPMI, 2% FBS are added to the rsVCAM1 coated plates and incubated for 30 minutes at room temperature prior to cell binding as described above. MAb HP1/2 (anti-VLA-4) or any recombinant humanized anti-VLA-4 antibody prepared as described herein must be preincubated with labelled cells for 30 minutes at room temperature prior to the cell binding. Concentrations of the antibodies preincubated will vary, but generally concentrations were in the range of about 1 µg/ml.

In these adhesion assays, murine HP1/2 inhibits Ramos cell binding completely at about 40 ng/ml, and half maximally at about 15 ng/ml (10 µM). The results of adhesion assays as represented by the calculated half-maximal binding constants using humanized recombinant anti-VLA-4 antibodies made according to the present invention are shown in Table III. The number (n) of experiments performed for each value is indicated for the recombinant humanized antibodies. As discussed below, these results generally compare well with the results obtained with the FACS binding assay.

The potency of recombinant Stage 0, Stage 1, Stage 2 and Stage 3 antibodies having the VK1 (DQL) light chain that had been purified from stably transfected YB2/0 cell lines was measured in the adhesion assay, as shown in Table M. The results showed that there was no inhibition detected in concentrations up to 1 µg/ml (1000 ng/ml) with the Stage 0-B and 0-C humanized antibodies. The results with the recombinant Stage 3 antibodies STAW and AS having the improved VK2 (SVMDY) light chain showed that the AS/SVMDY antibody was at least equipotent and perhaps more potent than the murine HP1/2 antibody. Certain Stage 2 and Stage 3 constructs showed potencies of about 20% to about 100% of the potency of the murine HP1/2 antibody.

2. FACS Assays

The binding of humanized recombinant antibodies to the cell surface can be assessed directly by fluorescence activated cell sorter (FACS) analysis, using fluorescently labelled antibodies. This is a standard technique that also provides half-maximal binding information following dose response measurements. The FACS methods are described in Lobb et al., 1991b [82].

Briefly, 25 µl cells ($4 \times 10^6$/ml in FACS buffer (PBS 2% FBS, 0.1% $NaN_3$) on ice are added to 5 µl of 5 µg/ml FITC or phycoerythrin (PE) conjugated antibody in FACS buffer, and incubated in V-bottomed microliter wells on ice for 30 minutes. To the wells, 125 µl of FACS buffer is added, the plates are centrifuged at 350×g for 5 minutes, and the supernatant is shaken off. To each well is added 125 µl FACS buffer, then the cells are transferred to 12×75 mm Falcon polystyrene tubes and resuspended to a final volume of 250 µl in FACS buffer. The mixture is analyzed on a Becton Dickinson FACS tar. The results of the FACS assays as represented by the calculated half-maximal binding constructs using humanized recombinant anti-VLA-4 antibodies made according to the present invention are shown in Table III and the number (n) of experiments performed for each value is indicated for the humanized antibodies. Table III also shows the potency calculated from the combined adhesion and FACS assays. Murine HP1/2 binds half-maximally to Ramos cells at 15 ng/ml. The AS/SVMDY humanized antibody binds half-maximally to Ramos cells at 12 ng/ml. Thus, the two assays (i.e., adhesion and FACS assays) show an excellent correlation for the murine antibody and the humanized AS/SVMDY antibody.

TABLE III

SUMMARY OF HALF-MAXIMAL BINDING CONSTANTS FOR HUMANIZED RECOMBINANT ANTI-VLA-4 ANTIBODIES

| Antibody | Adhesion Assay | FACS Assay | Combination |
|---|---|---|---|
| Murine HP1/2 | 15 ng/ml | 15 ng/ml | 15 ng/ml |
| Stage 0 (Humanized heavy chain) | >1000 ng/ml (n = 3) | — | — |
| Stage 1 (Humanized heavy chain) | 228 ng/ml (n = 6) | — | 228 ng/ml (n = 6) |
| Stage 2 (Ser mutant) | 56 ng/ml (n = 14) | 47 ng/ml (n = 6) | 60 ng/ml (n = 20) |
| Stage 3 | | | |
| (STAW) | 30 ng/ml (n = 3) | 33 ng/ml (n = 3) | 32 ng/ml (n = 6) |
| (KAITAS) | 85 ng/ml (n = 2) | 100 ng/ml (n = 1) | 90 ng/ml (n = 3) |
| (SSE) | 100 ng/ml | 40 ng/ml | 80 ng/ml |

TABLE III-continued

SUMMARY OF HALF-MAXIMAL BINDING CONSTANTS FOR HUMANIZED RECOMBINANT ANTI-VLA-4 ANTIBODIES

| Antibody | Adhesion Assay | FACS Assay | Combination |
|---|---|---|---|
| | (n = 2) | (n = 1) | (n = 3) |
| (KRS) | 50 ng/ml | 70 ng/ml | 57 ng/ml |
| | (n = 2) | (n = 1) | (n = 3) |
| (AS) | 28 ng/ml | 14 ng/ml | 21 ng/ml |
| | (n = 2) | (n = 2) | (n = 4) |
| Constructs with improved light chain | | | |
| STAW/SVMDY | 25 ng/ml | 35 ng/ml | 29 ng/ml |
| | (n = 4) | (n = 3) | (n = 7) |
| AS/SVMDY | 12 ng/ml | 12 ng/ml | 12 ng/ml |
| | (n = 2) | (n = 2) | (n = 4) |

Deposits

The following plasmids in *E. coli* K12 J221 (Iq) cells were deposited under the Budapest Treaty with American Type Culture Collection (ATCC), Rockville, Md. (USA) on Oct. 30, 1992. The deposits are identified as follows:

| Plasmid | Accession No. |
|---|---|
| pBAG 184 ($V_H$-STAW) | 69110 |
| pBAG 183 ($V_H$-KAITAS) | 69109 |
| pBAG 185 ($V_H$-KRS) | 69111 |
| pBAG 207 ($V_H$-SSE) | 69116 |
| pBAG 195 ($V_H$-AS) | 69113 |
| pBAG 190 (VK1-DQL) | 69112 |
| pBAG 198 (VK2-SVMDY) | 69115 |
| pBAG 197 (VK3-DQMDY) | 69114 |

In addition, an NSO cell line producing humanized recombinant anti-VLA-4 antibody was deposited under the Budapest Treaty with American Type Culture Collection (ATCC), Rockville, Md. (USA) on Nov. 3, 1992. The deposit was given ATCC accession no. CRL 11175.

Sequences

The following is a summary of the sequences set forth in the Sequence Listing:

SEQ ID NO: 1 DNA sequence of CG1FOR primer
SEQ ID NO: 2 DNA sequence of CK2FOR primer
SEQ ID NO: 3 DNA sequence of VH1BACK primer
SEQ ID NO: 4 DNA sequence of VH5BACK primer
SEQ ID NO: 5 DNA sequence of HP1/2 heavy chain variable region
SEQ ID NO: 6 Amino acid sequence of HP1/2 heavy chain variable region
SEQ ID NO: 7 DNA sequence of VK1BACK primer
SEQ ID NO: 8 DNA sequence of VK7BACK primer
SEQ ID NO: 9 DNA sequence of HP1/2 light chain variable region
SEQ ID NO: 10 Amino acid sequence of HP1/2 light chain variable region
SEQ ID NO: 11 DNA sequence of VH1FOR primer
SEQ ID NO: 12 DNA sequence of VK3BACK primer
SEQ ID NO: 13 DNA sequence of VK1FOR primer
SEQ ID NO: 14 DNA sequence of VH insert in M13VHPCR1
SEQ ID NO: 15 Amino acid sequence of VH insert in M13VHPCR1
SEQ ID NO: 16 DNA sequence of VK insert in M13VKPCR2
SEQ ID NO: 17 Amino acid sequence of VK insert in M13VKPCR2
SEQ ID NO: 18 DNA sequence of OLIGO598
SEQ ID NO: 19 DNA sequence of OLIGO599
SEQ ID NO: 20 DNA sequence of OLIGO600
SEQ ID NO: 21 DNA sequence of OLIGO605
SEQ ID NO: 22 DNA sequence of OLIGO606
SEQ ID NO: 23 DNA sequence of OLIGO607
SEQ ID NO: 24 DNA sequence of OLIGO10
SEQ ID NO: 25 DNA sequence of OLIGO385
SEQ ID NO: 26 DNA sequence of OLIGO11
SEQ ID NO: 27 DNA sequence of OLIGO391
SEQ ID NO: 28 DNA sequence of Stage 1 heavy chain variable region
SEQ ID NO: 29 Amino acid sequence of Stage 1 heavy chain variable region
SEQ ID NO: 30 DNA sequence of VK1 (DQL) light chain variable region
SEQ ID NO: 31 Amino acid sequence of VK1 (DQL) light chain variable region
SEQ ID NO: 32 DNA sequence of Stage 2 heavy chain variable region
SEQ ID NO: 33 Amino acid sequence of Stage 2 heavy chain variable region
SEQ ID NO: 34 DNA sequence of OLIGO684
SEQ ID NO: 35 DNA sequence of OLIGO683
SEQ ID NO: 36 DNA sequence of OLIGO713
SEQ ID NO: 37 DNA sequence of OLIGO716
SEQ ID NO: 38 DNA sequence of STAW heavy chain variable region
SEQ ID NO: 39 Amino acid sequence of STAW heavy chain variable region
SEQ ID NO: 40 DNA sequence of OLIGO706
SEQ ID NO: 41 DNA sequence of OLIGO707
SEQ ID NO: 42 DNA sequence of KAITAS heavy chain variable region
SEQ ID NO: 43 Amino acid sequence of KAITAS heavy chain variable region
SEQ ID NO: 44 DNA sequence of OLIGO768
SEQ ID NO: 45 DNA sequence of OLIGO769
SEQ ID NO: 46 DNA sequence of SSE heavy chain variable region
SEQ ID NO: 47 Amino acid sequence of SSE heavy chain variable region
SEQ ID NO: 48 DNA sequence of OLIGO704
SEQ ID NO: 49 DNA sequence of OLIGO705
SEQ ID NO: 50 DNA sequence of KRS heavy chain variable region
SEQ ID NO: 51 Amino acid sequence of KRS heavy chain variable region
SEQ ID NO: 52 DNA sequence of OLIGO745
SEQ ID NO: 53 DNA sequence of OLIGO746
SEQ ID NO: 54 DNA sequence of AS heavy chain variable region
SEQ ID NO: 55 Amino acid sequence of AS heavy chain variable region
SEQ ID NO: 56 DNA sequence of OLIGO915
SEQ ID NO: 57 DNA sequence of OLIGO917
SEQ ID NO: 58 DNA sequence of OLIGO918
SEQ ID NO: 59 DNA sequence of OLIOG919
SEQ ID NO: 60 DNA sequence of OLIGO697
SEQ ID NO: 61 DNA sequence of OLIGO698
SEQ ID NO: 62 DNA sequence of VK2 (SVMDY) light chain variable region
SEQ ID NO: 63 Amino acid sequence of VK2 (SVMDY) light chain variable region
SEQ ID NO: 64 DNA sequence of OLIGO803
SEQ ID NO: 65 DNA sequence of OLIGO804
SEQ ID NO: 66 DNA sequence of VK3 (DQMDY) light chain variable region SEQ ID NO: 67 Amino acid sequence of VK3 (DQMDY) light chain variable region
SEQ ID NO: 68 DNA sequence of PDLN heavy chain variable region
SEQ ID NO: 69 Amino acid sequence of PDLN heavy chain variable region
SEQ ID NO: 70 DNA sequence of PDLN light chain variable region
SEQ ID NO: 71 Amino acid sequence of PDLN light chain variable region
SEQ ID NO: 72 DNA sequence of Oligo 370-119
SEQ ID NO: 73 DNA sequence of Oligo 370-120
SEQ ID NO: 74 DNA sequence of Oligo 370-121
SEQ ID NO: 75 DNA sequence of Oligo 370-122
SEQ ID NO: 76 DNA sequence of Oligo 370-123
SEQ ID NO: 77 DNA sequence of Oligo 370-124
SEQ ID NO: 78 DNA sequence of Oligo 370-125
SEQ ID NO: 79 DNA sequence of Oligo 370-126
SEQ ID NO: 80 DNA sequence of Oligo 370-127
SEQ ID NO: 81 DNA sequence of Oligo 370-128
SEQ ID NO: 82 DNA sequence of Oligo 370-129
SEQ ID NO: 83 DNA sequence of Oligo 370-130
SEQ ID NO: 84 DNA sequence of Oligo 370-131
SEQ ID NO: 85 DNA sequence of Oligo 370-132
SEQ ID NO: 86 DNA sequence of Oligo 370-133
SEQ ID NO: 87 DNA sequence of Oligo 370-134
SEQ ID NO: 88 DNA sequence of Oligo 370-135
SEQ ID NO: 89 DNA sequence of Oligo 370-136
SEQ ID NO: 90 DNA sequence of Oligo 370-137
SEQ ID NO: 91 DNA sequence of Oligo 370-138
SEQ ID NO: 92 DNA sequence of Oligo 370-139
SEQ ID NO: 93 DNA sequence of Oligo 370-140
SEQ ID NO: 94 DNA sequence of Oligo 370-141
SEQ ID NO: 95 DNA sequence of Oligo 370-142
SEQ ID NO: 96 DNA sequence of VK1-DQL primer 370-247
SEQ ID NO: 97 DNA sequence of VK1-DQL primer 370-210
SEQ ID NO: 98 DNA sequence of VK2-SVMDY primer 370-269
SEQ ID NO: 99 DNA sequence of VK3-DQMDY primer 370-268

While we have herein before described a number of embodiments of this invention, it is apparent that our basic embodiments can be altered to provide other embodiments that utilize the compositions and processes of this invention. Therefore, it will be appreciated that the scope of this invention includes all alternative embodiments and variations which are defined in the foregoing specification and by the claims appended hereto; and the invention is not to be limited by the specific embodiments that have been presented herein by way of example.

List of References Cited

[1] Kohler, G. and Milstein, 1975, C. Nature 265:295-497, "Continuous Cultures of Fused Cells Secreting Antibody of Predefined Specificity"
[2] Schroff et al., 1985, Cancer Res 45: 879-885, "Human-antimurine immunoglobulin responses in patients receiving monoclonal antibody therapy"
[3] Borrebaeck et al., 1990, in *Therapeutic Monoclonal Antibodies*, Borrebaeck and Larrick (eds.), Stockton Press pp. 1-15
[4] Riechmann et al., 1988, Nature 332: 323-327, "Reshaping human antibodies for therapy"
[5] Tempest et al., 1991, Biotechnology 9: 266-271, "Reshaping a human monoclonal antibody to inhibit human respiratory syncytial virus infection in vivo"
[6] EP 120694 (Celltech Limited)
[7] EP 125023 (Genentech, Inc. and City of Hope)
[8] WO 86/01533 (Celltech Limited)
[9] Begent et al., 1990, Br. J. Cancer 62: 487
[10] U.S. Pat. No. 4,816,567, Cabilly et al., "Recombinant Immunoglobin Preparations", issued Mar. 28, 1989.
[11] U.S. Pat. No. 4,816,397, Boss et al., "Multichain Polypeptides Or Proteins And Processes For Their Production", issued Mar. 28, 1989.
[12] EP 0239400 (Winter)
[13] Verhoeyen et al., 1988, Science 239: 1534-1536, "Reshaping of human antibodies using CDR-grafting in Monoclonal Antibodies"
[14] WO 89/07454 (Medical Research Council)
[15] Kabat et al., 1991, 5th Ed., 4 vol., Sequences of Proteins of Immunological Interest U.S. Department of Health Human Services, NIH, USA
[16] Wu et al., 1970, "An Analysis of the Sequences of the Variable Regions of Bence Jones Proteins and Myeloma Light Chains and Their Implications for Antibody Complementarity", J. Exp. Med. 132: 211-250
[17] Queen et al., 1989, Proc. Natl. Acad. Sci. USA 86: 10029-10033, "A humanized antibody that binds to the interleukin 2 receptor"
[18] WO 90/07861 (Protein Design Labs Inc.)
[19] Co. et al., 1991, Proc. Natl. Acad. Sci. USA 88: 2869-2873, "Humanised antibodies for antiviral therapy"
[20] Bruggemann, et al., 1989., J. Exp. Med. 170:2153-2157, "The immunogenicity of chimeric antibodies"
[21] Verhoeyen et al., 1991, "Reshaping of Human Antibodies Using CDR-Grafting" in *Monoclonal Antibodies*, Chapman and Hall, pp. 37-43.
[22] WO 92/04881 (Scotgen Limited)
[23] Hale et al., 1988, "Remission induction in non-Hodgkin Lymphoma with Reshaped Human Monoclonal Antibody CAMPATH-1H", Lancet ii 1394-1398.
[24] Harlan, J. M, 1985, Blood 65: 513-526, "Leukocyte-endothelial interactions"
[25] Collins, et al., 1986, Proc. Natl. Acad. Sci. USA 83: 446-450, "Recombinant Human Tumor Necrosis Factor Increases mRNA Levels and Surface Expression of HLA-A, B antigens in vascular endothelial cells and dermal fibroblasts in vitro"
[26] Pober et al., 1986, "Overlapping Pattern of Activation of Human Endothelial Cells by Interleukin-1, Tumor Necrosis Factor, and Immune Interferon, J. Immunol. 137: 1893-1896
[27] Bevilacqua, et al., 1987, Proc. Natl. Acad. Sci. USA 84: 9238-9242, "Identification of an Inducible Endothelial-Leukocyte Adhesion Molecule"
[28] Leeuwenberg, et al., 1989, "Induction of an Activation Antigen on Human Endothelial Cells in vitro, Eur. J. Immunol. 19: 715-729
[29] Bevilacqua, et al., 1989, "Endothelial leukocyte adhesion molecule 1; an inducible receptor for neutrophils related to complement regulatory proteins and lectins, Science 243:1160-1165.
[30] Dustin, et al., 1986, "Induction by IL-1 and Interferon-γ: tissue distribution, biochemistry, and function of a natural adherence molecule (ICAM-1), J. Immunol. 137:245-254
[31] Boyd et al., 1988, "Intercellular adhesion molecule 1 (ICAM-1) has a central role in cell-cell contact-mediated immune mechanisms, Proc. Natl. Acad. Sci. USA 85: 3095-3099
[32] Dustin and Springer, 1988, "Lymphocyte function-associated antigen-1 (LFA-1) Interaction with Intercellular Adhesion Molecule-1 (ICAM-1) is one of at least three mechanisms for lymphocyte adhesion to cultured endothelial cells", J. Cell Biol. 107:321-331
[33] Osborn et al., 1989, "Direct Cloning of Vascular Cell Adhesion Molecule 1, a cytokine-induced endothelial protein that binds to lymphocytes, Cell 59: 1203-1211
[34] Hynes, 1987, "Integrins: a family of cell surface receptors" Cell 48: 549-554
[35] Marcantonio and Hynes, 1988, "Antibodies to the conserved cytoplasmic domain of the integrin $\beta_1$ subunit react with proteins in vertebrates, invertebrates and fungi, J. Cell Biol. 106: 1765-1772
[36] Kishimoto et al., 1989, "The leukocyte integrins", Adv. Immunol. 46: 149-182
[37] Ruoslahti, 1988, "Fibronectin and its receptors" Annu. Rev. Biochem. 57: 375-413
[38] Hemler et al., 1990, "VLA proteins in the integrin family: structures, functions and their role on leukocytes" Annu Rev. Immunol. 8:365-400
[39] Hemler et al., 1987, "Characterization of the cell surface heterodimer VLA-4 and related peptides" J. Biol. Chem. 262:11478-11485
[40] Clayberger, et al., 1987, "Identification and Characterization of two novel lymphocyte function-associated antigens, L24 and L25" J. Immunol. 138:1510-1514
[41] Takada et al., 1989, "The Primary Structure of the $\alpha 4$ subunit of VLA-4; homology to other integrins and a possible cell-cell adhesion function:, EMBO J. 8:1361-1368
[42] Holtzmann et al., 1989, "Identification of a murine Peyer's patch-specific lymphocyte homing receptor as an integrin molecule with an $\alpha$ chain homologous to human VLA-4$\alpha$," Cell 56:37-46
[43] Bednarczyk and McIntyre, 1990, "A monoclonal antibody to VLA-4-$\alpha$ chain (CDw49) induces homotypic lymphocyte aggregation", J. Immunol. in press
[44] Wayner et al., 1989, "Identification and characterization of the lymphocyte adhesion receptor for an alternative cell attachment domain in plasma fibronectin", J. Cell Biol. 109:1321-1330
[45] Elices et al., 1990, "VCAM-1 on Activated Endothelium Interacts with the Leukocyte Integrin VLA-4 at a Site Distinct from the VLA-4/Fibronectin Binding Site", Cell 60:577-584
[46] Rice et al., 1989, "An inducible endothelial cell surface glycoprotein mediates melanoma adhesion," Science, 246: 1303-1306
[47] Cybulsky, M. I. and Gimbrone, M. A., Jr. 1991, "Endothelial expression of a mononuclear leukocyte adhesion molecule during atherogenesis," Science, 251:788-791
[48] Freedman et al., 1990, "Adhesion of human B cells to germinal centers in vitro involves VLA-4 and INCAM-110," Science, 249:1030-1033
[49] Miyake et al., 1991, "A VCAM-like adhesion molecule on murine bone marrow stromal cells mediates binding of lymphocyte precursors in culture," J. Cell Biol., 114:557-565
[50] Polte et al., 1990, "Full length vascular cell adhesion molecule 1 (VCAM-1)," Nuc. Ac. Res., 18:5901
[51] Hession et al., 1991, "Cloning of an alternate form of vascular cell adhesion molecule-1 (VCAM1)", J. Biol. Chem., 266:6682-6685
[52] Osborn and Benjamin, U.S. Ser. No. 07/821,712 filed Sep. 30, 1991
[53] Carlos et al., 1990, "Vascular cell adhesion molecule-1 mediates lymphocyte adherence to cytokine-activated cultured human endothelial cells," Blood, 76, 965-970
[54] Pulido et al., 1991, "Functional Evidence for Three Distinct and Independently Inhibitable Adhesion Activities Mediated by the Human Integrin VLA-4," J. Biol. Chem., 266(16):10241-10245
[55] Sanchez-Madrid et al., 1986, "VLA-3: A novel polypeptide association within the VLA molecular complex: cell distribution and biochemical characterization," Eur. J. Immunol., 16:1343-1349
[56] Weller et al., 1991, "Human eosinophil adherence to vascular endothelium mediated by binding to vascular cell adhesion molecule 1 and endothelial leukocyte adhesion molecule 1," Proc. Natl. Acad. Sci. USA, 4488:7430-7433
[57] Walsh et al., 1991, "Human Eosinophil, But Not Neutrophil, Adherence to IL-1-Stimulated Human Umbilical Vascular Endothelial Cells Is $\alpha_4\beta_1$ (Very Late Antigen-4) Dependent," J. Immunol., 146:3419-3423
[58] Bochner et al., 1991, "Adhesion of Human Basophils, Eosinophils, and Neutrophils to Interleukin 1-activated Human Vascular Endothelial Cells: Contributions of Endothelial Cell Adhesion Molecules," J. Exp. Med., 173: 1553-1556
[59] Dobrina et al., 1991, "Mechanisms of Eosinophil Adherence to Cultured Vascular Endothelial Cells," J. Clin. Invest., 88:20-26
[60] Lobb, U.S. Ser. No. 07/821,768 filed Jan. 13, 1992
[61] Lobb, U.S. Ser. No. 07/835,139 filed Feb. 12, 1992
[62] Papayannopoulou, U.S. Ser. No. 07/977,702 filed Nov. 13, 1992
[63] Favoloro et al., 1980, "Transcriptional Maps of Polyome Virus Specific RNA: Analysis by Two-Dimensional Nuclease S1 Gel Mapping", Methods in Enzymology 65:718-749.
[64] Orlandi et al., 1989, "Cloning immunoglobulin variable domains for expression by the polymerase chain reaction", Proc. Natl. Acad. Sci. USA 86:3833-3837.
[65] Huse et al., 1989, "Generation of a Large Combinational Library of Immunoglobulin Repertoire in Phage Lambda", Science 246:1275-1281.
[66] Jones and Bendig, 1991, "Rapid PCR-Cloning of Full-length Mouse Immunoglobulin Variable Regions", Biotechnology 9:88-89
[67] Saiki et al., 1988, "Primer-Directed Enzymatic Amplification of DNA with a Thermostable DNA Polymerase", Science 239:487-491
[68] *Molecular Cloning. A Laboratory Manual,* 1982, eds. T. Maniatis et al., published by Cold Spring Harbor Laboratory, Cold Spring Harbor, N.Y.
[69] Sanger et al., 1977, "DNA Sequencing with Chain-terminating Inhibitors", Proc. Natl. Acad. Sci. USA 74:5463-5467.
[70] Takahashi et al., 1982, "Structure of Human Immunoglobulin Gamma Genes: Implications for Evolution of a Gene Family", Cell 29:671-679,
[71] Flanagan and Rabbitts, 1982, "Arrangement of Human Immunoglobulin Heavy Chain Construct Region Genes Implies Evolutionary Amplification of a Segment Containing $\gamma$, $\epsilon$ and $\alpha$ genes", Nature 300:709-713.
[72] Hieter, 1980, "Cloned Human and Mouse Kappa Immunoglobulin Constant and J. Region Genes Conserve Homology in Functional Segments", Cell 22:197-207
[73] Kilmartin et al., 1982, "Rat Monoclonal Antitubulin Antibodies Derived by Using a New Non-secreting Rat Cell Line", J. Cell Biol. 93:576-582.
[74] Ho et al., 1989, "Site-directed Mutagenesis by Overlap Extension Using The Polymerase Chain Reaction", Gene 77:51-59

[75] Burkly et al., U.S. Ser. No. 07/916,098, filed Jul. 24, 1992
[76] Bebbington et al., 1992, "High-Level Expression of a Recombinant Antibody from Myeloma Cells Using A Glutamine Synthetase Gene as an Amplifiable Selectable Marker", Bio/Technology 10:169-175.
[77] WO86/05807 (Celltech Limited)
[78] WO87/04462 (Celltech Limited)
[79] WO89/01036 (Celltech Limited)
[80] WO89/10404 (Celltech Limited)
[81] Lobb et al., 1991a, "Expression and Functional Characterization of a Soluble Form of Vascular Cell Adhesion Molecule 1", Biochem. Biophys. Res. Comm. 178:1498-1504
[82] Lobb et al., 1991b, "Expression and Functional Characterization of a Soluble Form of Endothelial-Leukocyte Adhesion Molecule 1", J. Immunol. 147:124-129

Each of the above-listed references is hereby incorporated by reference in its entirety.

What is claimed is:

1. A humanized recombinant antibody molecule, or an alpha4-binding fragment thereof, comprising:

at least one antibody heavy chain, or an α4-binding fragment thereof, comprising non-human CDRs at positions 31-35 (CDR1), 50-65 (CDR2) and 95-102 (CDR3) (Kabat numbering) from a mouse anti-α4 antibody and framework regions from a humanized heavy chain variable region based on the HP1/2 heavy chain variable region (SEQ ID NO: 6); and at least one antibody light chain, or an α4-binding fragment thereof, comprising non-human CDRs at positions 24-34 (CDR1), 50-56 (CDR2) and 89-97 (CDR3) from a mouse anti-α4 antibody and framework regions from a humanized light chain variable region based on the HP1/2 light chain variable region (SEQ ID NO: 10), wherein said HP1/2 framework regions have non-human residues at framework positions 60 and 67.

* * * * *

SEQUENCE LISTING

```
<160> NUMBER OF SEQ ID NOS: 109

<210> SEQ ID NO 1
<211> LENGTH: 31
<212> TYPE: DNA
<213> ORGANISM: Artificial Sequence
<220> FEATURE:
<223> OTHER INFORMATION: primer for PCR

<400> SEQUENCE: 1
ggaagcttag acagatgggg gtgtcgtttt g                              31

<210> SEQ ID NO 2
<211> LENGTH: 32
<212> TYPE: DNA
<213> ORGANISM: Artificial Sequence
<220> FEATURE:
<223> OTHER INFORMATION: primer for PCR

<400> SEQUENCE: 2
ggaagcttga agatggatac agttggtgca gc                             32

<210> SEQ ID NO 3
<211> LENGTH: 22
<212> TYPE: DNA
<213> ORGANISM: Artificial Sequence
<220> FEATURE:
<223> OTHER INFORMATION: primer for PCR

<400> SEQUENCE: 3
aggtsmarct gcagsagtcw gg                                        22

<210> SEQ ID NO 4
<211> LENGTH: 32
<212> TYPE: DNA
<213> ORGANISM: Artificial Sequence
<220> FEATURE:
<223> OTHER INFORMATION: primer for PCR

<400> SEQUENCE: 4
ttgaattcgg tgccagakcw sahatygtka tg                             32

<210> SEQ ID NO 5
<211> LENGTH: 360
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(360)

<400> SEQUENCE: 5 gtc aaa ctg cag cag tct ggg gca gag ctt gtg aag cca ggg gcc tca    48
Val Lys Leu Gln Gln Ser Gly Ala Glu Leu Val Lys Pro Gly Ala Ser
```

```
                1               5                  10                 15
gtc aag ttg ttc tgc aca gct tct ggc ttc aac att aaa gac acc tat        96
Val Lys Leu Phe Cys Thr Ala Ser Gly Phe Asn Ile Lys Asp Thr Tyr
             20                  25                 30 atg cac tgg gtg aag cag agg cct caa cag ggc ctg gag tgg att gga       144
Met His Trp Val Lys Gln Arg Pro Gln Gln Gly Leu Glu Trp Ile Gly
         35                  40                 45 agg att gat cct gcg agt ggc gat act aaa tat gac ccg aag ttc cag       192
Arg Ile Asp Pro Ala Ser Gly Asp Thr Lys Tyr Asp Pro Lys Phe Gln
     50                  55                 60 gtc aag gcc act att aca gcg gac acg tcc tcc aac aca gcc tgg ctg       240
Val Lys Ala Thr Ile Thr Ala Asp Thr Ser Ser Asn Thr Ala Trp Leu
 65                  70                 75                  80 cag ctc agc agc ctg aca tct gag gac act gcc gtc tac tac tgt gca       288
Gln Leu Ser Ser Leu Thr Ser Glu Asp Thr Ala Val Tyr Tyr Cys Ala
                 85                  90                 95 gac gga atg tgg gta tca acg gga tat gct ctg gac ttc tgg ggc caa       336
Asp Gly Met Trp Val Ser Thr Gly Tyr Ala Leu Asp Phe Trp Gly Gln
             100                 105                110 ggg acc acg gtc acc gtc tcc tca                                        360
Gly Thr Thr Val Thr Val Ser Ser
         115                 120

<210> SEQ ID NO 6
<211> LENGTH: 120
<212> TYPE: PRT
<213> ORGANISM: Artificial Sequence
<220> FEATURE:
<223> OTHER INFORMATION: heavy chain variable region

<400> SEQUENCE: 6

Val Lys Leu Gln Gln Ser Gly Ala Glu Leu Val Lys Pro Gly Ala Ser
 1               5                  10                 15

Val Lys Leu Phe Cys Thr Ala Ser Gly Phe Asn Ile Lys Asp Thr Tyr
             20                  25                 30

Met His Trp Val Lys Gln Arg Pro Gln Gln Gly Leu Glu Trp Ile Gly
         35                  40                 45

Arg Ile Asp Pro Ala Ser Gly Asp Thr Lys Tyr Asp Pro Lys Phe Gln
     50                  55                 60

Val Lys Ala Thr Ile Thr Ala Asp Thr Ser Ser Asn Thr Ala Trp Leu
 65                  70                 75                  80

Gln Leu Ser Ser Leu Thr Ser Glu Asp Thr Ala Val Tyr Tyr Cys Ala
                 85                  90                 95

Asp Gly Met Trp Val Ser Thr Gly Tyr Ala Leu Asp Phe Trp Gly Gln
             100                 105                110

Gly Thr Thr Val Thr Val Ser Ser
         115                 120

<210> SEQ ID NO 7
<211> LENGTH: 24
<212> TYPE: DNA
<213> ORGANISM: Artificial Sequence
<220> FEATURE:
<223> OTHER INFORMATION: primer for PCR

<400> SEQUENCE: 7
gacattcagc tgacccagtc tcca                                             24

<210> SEQ ID NO 8
<211> LENGTH: 32
<212> TYPE: DNA
```

```
<213> ORGANISM: Artificial Sequence
<220> FEATURE:
<223> OTHER INFORMATION: primer for PCR

<400> SEQUENCE: 8
ttgaattcgg agttgatggg aacattgtaa tg                                      32

<210> SEQ ID NO 9
<211> LENGTH: 318
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)...(318)

<400> SEQUENCE: 9 agt att gtg atg acc cag act ccc aaa ttc ctg ctt gtt tca gca gga        48
Ser Ile Val Met Thr Gln Thr Pro Lys Phe Leu Leu Val Ser Ala Gly
 1               5                  10                  15 gac agg gtt acc ata acc tgc aag gcc agt cag agt gtg act aat gat        96
Asp Arg Val Thr Ile Thr Cys Lys Ala Ser Gln Ser Val Thr Asn Asp
             20                  25                  30 gta gct tgg tac caa cag aag cca ggg cag tct cct aaa ctg ctg ata       144
Val Ala Trp Tyr Gln Gln Lys Pro Gly Gln Ser Pro Lys Leu Leu Ile
         35                  40                  45 tat tat gca tcc aat cgc tac act gga gtc cct gat cgc ttc act ggc       192
Tyr Tyr Ala Ser Asn Arg Tyr Thr Gly Val Pro Asp Arg Phe Thr Gly
     50                  55                  60 agt gga tat ggg acg gat ttc act ttc acc atc agc act gtg cag gct       240
Ser Gly Tyr Gly Thr Asp Phe Thr Phe Thr Ile Ser Thr Val Gln Ala
 65                  70                  75                  80 gaa gac ctg gca gtt tat ttc tgt cag cag gat tat agc tct ccg tac       288
Glu Asp Leu Ala Val Tyr Phe Cys Gln Gln Asp Tyr Ser Ser Pro Tyr
                 85                  90                  95 acg ttc gga ggg ggg acc aag ctg gag atc                                318
Thr Phe Gly Gly Gly Thr Lys Leu Glu Ile
                100                 105

<210> SEQ ID NO 10
<211> LENGTH: 106
<212> TYPE: PRT
<213> ORGANISM: Artificial Sequence
<220> FEATURE:
<223> OTHER INFORMATION: light chain variable region

<400> SEQUENCE: 10

Ser Ile Val Met Thr Gln Thr Pro Lys Phe Leu Leu Val Ser Ala Gly
 1               5                  10                  15

Asp Arg Val Thr Ile Thr Cys Lys Ala Ser Gln Ser Val Thr Asn Asp
             20                  25                  30

Val Ala Trp Tyr Gln Gln Lys Pro Gly Gln Ser Pro Lys Leu Leu Ile
         35                  40                  45

Tyr Tyr Ala Ser Asn Arg Tyr Thr Gly Val Pro Asp Arg Phe Thr Gly
     50                  55                  60

Ser Gly Tyr Gly Thr Asp Phe Thr Phe Thr Ile Ser Thr Val Gln Ala
 65                  70                  75                  80

Glu Asp Leu Ala Val Tyr Phe Cys Gln Gln Asp Tyr Ser Ser Pro Tyr
                 85                  90                  95

Thr Phe Gly Gly Gly Thr Lys Leu Glu Ile
                100                 105
```

<210> SEQ ID NO 11
<211> LENGTH: 34
<212> TYPE: DNA
<213> ORGANISM: Artificial Sequence
<220> FEATURE:
<223> OTHER INFORMATION: primer for PCR

<400> SEQUENCE: 11
tgaggagacg gtgaccgtgg tcccttggcc ccag                              34

<210> SEQ ID NO 12
<211> LENGTH: 17
<212> TYPE: DNA
<213> ORGANISM: Artificial Sequence
<220> FEATURE:
<223> OTHER INFORMATION: primer for PCR

<400> SEQUENCE: 12
gacattcagc tgaccca                                                 17

<210> SEQ ID NO 13
<211> LENGTH: 22
<212> TYPE: DNA
<213> ORGANISM: Artificial Sequence
<220> FEATURE:
<223> OTHER INFORMATION: primer for PCR

<400> SEQUENCE: 13
gttagatctc cagcttggtc cc                                           22

<210> SEQ ID NO 14
<211> LENGTH: 621
<212> TYPE: DNA
<213> ORGANISM: Artificial Sequence
<220> FEATURE:
<223> OTHER INFORMATION: heavy chain variable region insert
<220> FEATURE:
<221> NAME/KEY: CDS
<222> LOCATION: (122)...(167)
<223> OTHER INFORMATION: signal peptide
<220> FEATURE:
<221> NAME/KEY: CDS
<222> LOCATION: (250)...(621)
<223> OTHER INFORMATION: signal peptide
<220> FEATURE:
<221> NAME/KEY: exon
<222> LOCATION: (261)...(621)
<220> FEATURE:
<221> NAME/KEY: mat_peptide
<222> LOCATION: (261)...(621)
<220> FEATURE:
<221> NAME/KEY: TATA_signal
<222> LOCATION: (38)...(45)

<400> SEQUENCE: 14
aagcttatga atatgcaaat cctctgaatc tacatggtaa atataggttt gtctatacca    60
caaacagaaa aacatgagat cacagttctc tctacagtta ctgagcacac aggacctcac   120 c atg gga tgg agc tgt atc atc ctc ttc ttg gta gca aca gct aca g    167
  Met Gly Trp Ser Cys Ile Ile Leu Phe Leu Val Ala Thr Ala Thr
   1               5                  10                  15 gtaaggggct cacagtagca ggcttgaggt ctggacatat atatgggtga caatgacatc   227
cactttgcct ttctctccac ag gt gtc cac tcc cag gtc caa ctg cag gag    278
                         Gly Val His Ser Gln Val Gln Leu Gln Glu
                                          20                  25 agc ggt cca ggt ctt gtg aga cct agc cag acc ctg agc ctg acc tgc    326
Ser Gly Pro Gly Leu Val Arg Pro Ser Gln Thr Leu Ser Leu Thr Cys
             30                  35                  40

```
acc gtg tct ggc agc acc ttc agc agc tac tgg atg cac tgg gtg aga      374
Thr Val Ser Gly Ser Thr Phe Ser Ser Tyr Trp Met His Trp Val Arg
         45                  50                  55 cag cca cct gga cga ggt ctt gag tgg att gga agg att gat cct aat      422
Gln Pro Pro Gly Arg Gly Leu Glu Trp Ile Gly Arg Ile Asp Pro Asn
     60                  65                  70 agt ggt ggt act aag tac aat gag aag ttc aag agc aga gtg aca atg      470
Ser Gly Gly Thr Lys Tyr Asn Glu Lys Phe Lys Ser Arg Val Thr Met
 75                  80                  85 ctg gta gac acc agc aag aac cag ttc agc ctg aga ctc agc agc gtg      518
Leu Val Asp Thr Ser Lys Asn Gln Phe Ser Leu Arg Leu Ser Ser Val
         90                  95                 100                 105 aca gcc gcc gac acc gcg gtc tat tat tgt gca aga tac gat tac tac      566
Thr Ala Ala Asp Thr Ala Val Tyr Tyr Cys Ala Arg Tyr Asp Tyr Tyr
                    110                 115                 120 ggt agc agc tac ttt gac tac tgg ggc caa ggg acc acg gtc acc gtc      614
Gly Ser Ser Tyr Phe Asp Tyr Trp Gly Gln Gly Thr Thr Val Thr Val
                125                 130                 135 tcc tca g                                                            621
Ser Ser <210> SEQ ID NO 15
<211> LENGTH: 139
<212> TYPE: PRT
<213> ORGANISM: Artificial Sequence
<220> FEATURE:
<223> OTHER INFORMATION: heavy chain variable region insert

<400> SEQUENCE: 15

Met Gly Trp Ser Cys Ile Ile Leu Phe Leu Val Ala Thr Ala Thr Gly
 1               5                  10                  15

Val His Ser Gln Val Gln Leu Gln Glu Ser Gly Pro Gly Leu Val Arg
             20                  25                  30

Pro Ser Gln Thr Leu Ser Leu Thr Cys Thr Val Ser Gly Ser Thr Phe
         35                  40                  45

Ser Ser Tyr Trp Met His Trp Val Arg Gln Pro Pro Gly Arg Gly Leu
     50                  55                  60

Glu Trp Ile Gly Arg Ile Asp Pro Asn Ser Gly Gly Thr Lys Tyr Asn
 65                  70                  75                  80

Glu Lys Phe Lys Ser Arg Val Thr Met Leu Val Asp Thr Ser Lys Asn
                 85                  90                  95

Gln Phe Ser Leu Arg Leu Ser Ser Val Thr Ala Ala Asp Thr Ala Val
            100                 105                 110

Tyr Tyr Cys Ala Arg Tyr Asp Tyr Tyr Gly Ser Ser Tyr Phe Asp Tyr
        115                 120                 125

Trp Gly Gln Gly Thr Thr Val Thr Val Ser Ser
130                 135

<210> SEQ ID NO 16
<211> LENGTH: 594
<212> TYPE: DNA
<213> ORGANISM: Artificial Sequence
<220> FEATURE:
<223> OTHER INFORMATION: light chain variable region insert
<220> FEATURE:
<221> NAME/KEY: CDS
<222> LOCATION: (134)...(179)
<220> FEATURE:
<221> NAME/KEY: CDS
<222> LOCATION: (262)...(594)
<220> FEATURE:
<221> NAME/KEY: exon
```

<222> LOCATION: (273)...(594)
<220> FEATURE:
<221> NAME/KEY: mat_peptide
<222> LOCATION: (273)...(594)
<220> FEATURE:
<221> NAME/KEY: TATA_signal
<222> LOCATION: (50)...(57)

<400> SEQUENCE: 16
ctcttaaact tcaagcttat gaatatgcaa atcctctgaa tctacatggt aaatataggt    60
ttgtctatac cacaaacaga aaaacatgag atcacagttc tctctacagt tactgagcac   120
acaggacctc acc atg gga tgg agc tgt atc atc ctc ttc ttg gta gca      169
            Met Gly Trp Ser Cys Ile Ile Leu Phe Leu Val Ala
            1               5                   10 aca gct aca g gtaaggggct cacagtagca ggcttgaggt ctggacatat            219
Thr Ala Thr
         15 atatgggtga caatgacatc cactttgcct ttctctccac ag gt gtc cac tcc gac   275
                                                Gly Val His Ser Asp
                                                              20 atc cag ctg acc cag agc cca agc agc ctg agc gcc agc gtg ggt gac    323
Ile Gln Leu Thr Gln Ser Pro Ser Ser Leu Ser Ala Ser Val Gly Asp
              25                  30                  35 aga gtg acc atc acc tgt aga gcc agc ggt aac atc cac aac tac ctg    371
Arg Val Thr Ile Thr Cys Arg Ala Ser Gly Asn Ile His Asn Tyr Leu
          40                  45                  50 gct tgg tac cag cag aag cca ggt aag gct cca aag ctg ctg atc tac    419
Ala Trp Tyr Gln Gln Lys Pro Gly Lys Ala Pro Lys Leu Leu Ile Tyr
      55                  60                  65 tac acc acc acc ctg gct gac ggt gtg cca agc aga ttc agc ggt agc    467
Tyr Thr Thr Thr Leu Ala Asp Gly Val Pro Ser Arg Phe Ser Gly Ser
  70                  75                  80 ggt agc ggt acc gac ttc acc ttc acc atc agc agc ctc cag cca gag    515
Gly Ser Gly Thr Asp Phe Thr Phe Thr Ile Ser Ser Leu Gln Pro Glu
Ser
 85                  90                  95                 100 gac atc gcc acc tac tac tgc cag cac ttc tgg agc acc cca agg acg    563
Asp Ile Ala Thr Tyr Tyr Cys Gln His Phe Trp Ser Thr Pro Arg Thr
             105                 110                 115 ttc ggc caa ggg acc aag gtg gaa atc aaa c                          594
Phe Gly Gln Gly Thr Lys Val Glu Ile Lys
         120                 125

<210> SEQ ID NO 17
<211> LENGTH: 126
<212> TYPE: PRT
<213> ORGANISM: Artificial Sequence
<220> FEATURE:
<223> OTHER INFORMATION: light chain variable region insert

<400> SEQUENCE: 17

Met Gly Trp Ser Cys Ile Ile Leu Phe Leu Val Ala Thr Ala Thr Gly
1               5                   10                  15

Val His Ser Asp Ile Gln Leu Thr Gln Ser Pro Ser Ser Leu Ser Ala
            20                  25                  30

Ser Val Gly Asp Arg Val Thr Ile Thr Cys Arg Ala Ser Gly Asn Ile
        35                  40                  45

His Asn Tyr Leu Ala Trp Tyr Gln Gln Lys Pro Gly Lys Ala Pro Lys
    50                  55                  60

Leu Leu Ile Tyr Tyr Thr Thr Thr Leu Ala Asp Gly Val Pro Ser Arg
65                  70                  75                  80

Phe Ser Gly Ser Gly Ser Gly Thr Asp Phe Thr Phe Thr Ile Ser Ser

```
                85                  90                  95
Leu Gln Pro Glu Asp Ile Ala Thr Tyr Tyr Cys Gln His Phe Trp Ser
            100                 105                 110

Thr Pro Arg Thr Phe Gly Gln Gly Thr Lys Val Glu Ile Lys
            115                 120                 125

<210> SEQ ID NO 18
<211> LENGTH: 54
<212> TYPE: DNA
<213> ORGANISM: Artificial Sequence
<220> FEATURE:
<223> OTHER INFORMATION: mutagenizing oligonucleotide

<400> SEQUENCE: 18
tgtctcaccc agtgcatata ggtgtcttta atgttgaagc cagacacgct gcag       54

<210> SEQ ID NO 19
<211> LENGTH: 71
<212> TYPE: DNA
<213> ORGANISM: Artificial Sequence
<220> FEATURE:
<223> OTHER INFORMATION: mutagenizing oligonucleotide

<400> SEQUENCE: 19
cagcattgtc actctgacct ggaacttcgg gtcatatttta gtatcgccac tcgcaggatc   60
aatccttcca a                                                         71

<210> SEQ ID NO 20
<211> LENGTH: 70
<212> TYPE: DNA
<213> ORGANISM: Artificial Sequence
<220> FEATURE:
<223> OTHER INFORMATION: mutagenizing oligonucleotide

<400> SEQUENCE: 20
ggtcccttgg ccccagaagt ccagagcata tcccgttgat acccacattc cgtctgcaca   60
ataatagacc                                                           70

<210> SEQ ID NO 21
<211> LENGTH: 51
<212> TYPE: DNA
<213> ORGANISM: Artificial Sequence
<220> FEATURE:
<223> OTHER INFORMATION: mutagenizing oligonucleotide

<400> SEQUENCE: 21
tcccttggcc gaacgtgtac ggagagctat aatcctgctg gcagtagtag g            51

<210> SEQ ID NO 22
<211> LENGTH: 52
<212> TYPE: DNA
<213> ORGANISM: Artificial Sequence
<220> FEATURE:
<223> OTHER INFORMATION: mutagenizing oligonucleotide

<400> SEQUENCE: 22
atctgcttgg gcacaccagt gtagcgattg gatgcatagt agatcagcag ct           52

<210> SEQ ID NO 23
<211> LENGTH: 61
<212> TYPE: DNA
<213> ORGANISM: Artificial Sequence
<220> FEATURE:
<223> OTHER INFORMATION: mutagenizing oligonucleotide
```

-continued

<400> SEQUENCE: 23
tctgctggta ccaagctaca tcattagtca cactctgact ggccttacag gtgatggtca    60
c                                                                    61

<210> SEQ ID NO 24
<211> LENGTH: 17
<212> TYPE: DNA
<213> ORGANISM: Artificial Sequence
<220> FEATURE:
<223> OTHER INFORMATION: primer for PCR

<400> SEQUENCE: 24
gtaaaacgac ggccagt                                                   17

<210> SEQ ID NO 25
<211> LENGTH: 22
<212> TYPE: DNA
<213> ORGANISM: Artificial Sequence
<220> FEATURE:
<223> OTHER INFORMATION: primer for PCR

<400> SEQUENCE: 25
gcgggcctct tcgctattac gc                                             22

<210> SEQ ID NO 26
<211> LENGTH: 16
<212> TYPE: DNA
<213> ORGANISM: Artificial Sequence
<220> FEATURE:
<223> OTHER INFORMATION: primer for PCR

<400> SEQUENCE: 26
aacagctatg accatg                                                    16

<210> SEQ ID NO 27
<211> LENGTH: 22
<212> TYPE: DNA
<213> ORGANISM: Artificial Sequence
<220> FEATURE:
<223> OTHER INFORMATION: synthesized primer

<400> SEQUENCE: 27
ctctctcagg gccaggcggt ga                                             22

<210> SEQ ID NO 28
<211> LENGTH: 429
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(429)

<400> SEQUENCE: 28 atg gac tgg acc tgg agg gtc ttc tgc ttg ctg gct gta gca cca ggt    48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga    96
Ala His Ser Gln Val Gln Leu Gln Glu Ser Gly Pro Gly Leu Val Arg
                20                  25                  30 cct agc cag acc ctg agc ctg acc tgc acc gtg tct ggc ttc aac att   144
Pro Ser Gln Thr Leu Ser Leu Thr Cys Thr Val Ser Gly Phe Asn Ile
             35                  40                  45 aaa gac acc tat atg cac tgg gtg aga cag cca cct gga cga ggt ctt   192

```
Lys Asp Thr Tyr Met His Trp Val Arg Gln Pro Pro Gly Arg Gly Leu
        50                  55                  60 gag tgg att gga agg att gat cct gcg agt ggc gat act aaa tat gac    240
Glu Trp Ile Gly Arg Ile Asp Pro Ala Ser Gly Asp Thr Lys Tyr Asp
 65                  70                  75                  80 ccg aag ttc cag gtc aga gtg aca atg ctg gta gac acc agc aag aac    288
Pro Lys Phe Gln Val Arg Val Thr Met Leu Val Asp Thr Ser Lys Asn
                 85                  90                  95 cag ttc agc ctg aga ctc agc agc gtg aca gcc gcc gac acc gcg gtc    336
Gln Phe Ser Leu Arg Leu Ser Ser Val Thr Ala Ala Asp Thr Ala Val
                100                 105                 110 tat tat tgt gca gac gga atg tgg gta tca acg gga tat gct ctg gac    384
Tyr Tyr Cys Ala Asp Gly Met Trp Val Ser Thr Gly Tyr Ala Leu Asp
            115                 120                 125 ttc tgg ggc caa ggg acc acg gtc acc gtc tcc tca ggt gag tcc        429
Phe Trp Gly Gln Gly Thr Thr Val Thr Val Ser Ser Gly Glu Ser
        130                 135                 140

<210> SEQ ID NO 29
<211> LENGTH: 143
<212> TYPE: PRT
<213> ORGANISM: Artificial Sequence
<220> FEATURE:
<223> OTHER INFORMATION: heavy chain variable region

<400> SEQUENCE: 29

Met Asp Trp Thr Trp Arg Val Phe Cys Leu Leu Ala Val Ala Pro Gly
 1               5                  10                  15

Ala His Ser Gln Val Gln Leu Gln Glu Ser Gly Pro Gly Leu Val Arg
                20                  25                  30

Pro Ser Gln Thr Leu Ser Leu Thr Cys Thr Val Ser Gly Phe Asn Ile
            35                  40                  45

Lys Asp Thr Tyr Met His Trp Val Arg Gln Pro Pro Gly Arg Gly Leu
        50                  55                  60

Glu Trp Ile Gly Arg Ile Asp Pro Ala Ser Gly Asp Thr Lys Tyr Asp
 65                  70                  75                  80

Pro Lys Phe Gln Val Arg Val Thr Met Leu Val Asp Thr Ser Lys Asn
                 85                  90                  95

Gln Phe Ser Leu Arg Leu Ser Ser Val Thr Ala Ala Asp Thr Ala Val
                100                 105                 110

Tyr Tyr Cys Ala Asp Gly Met Trp Val Ser Thr Gly Tyr Ala Leu Asp
            115                 120                 125

Phe Trp Gly Gln Gly Thr Thr Val Thr Val Ser Ser Gly Glu Ser
        130                 135                 140

<210> SEQ ID NO 30
<211> LENGTH: 386
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)...(384)

<400> SEQUENCE: 30 atg ggt tgg tcc tgc atc atc ctg ttc ctg gtt gct acc gct acc ggt     48
Met Gly Trp Ser Cys Ile Ile Leu Phe Leu Val Ala Thr Ala Thr Gly
 1               5                  10                  15 gtt cac tcc gac atc cag ctg acc cag agc cca agc agc ctg agc gcc    96
Val His Ser Asp Ile Gln Leu Thr Gln Ser Pro Ser Ser Leu Ser Ala
                20                  25                  30
```

```
agc gtg ggt gac aga gtg acc atc acc tgt aag gcc agt cag agt gtg         144
Ser Val Gly Asp Arg Val Thr Ile Thr Cys Lys Ala Ser Gln Ser Val
         35                  40                  45 act aat gat gta gct tgg tac cag cag aag cca ggt aag gct cca aag         192
Thr Asn Asp Val Ala Trp Tyr Gln Gln Lys Pro Gly Lys Ala Pro Lys
 50                  55                  60 ctg ctg atc tac tat gca tcc aat cgc tac act ggt gtg cca agc aga         240
Leu Leu Ile Tyr Tyr Ala Ser Asn Arg Tyr Thr Gly Val Pro Ser Arg
 65                  70                  75                  80 ttc agc ggt agc ggt agc ggt acc gac ttc acc ttc acc atc agc agc         288
Phe Ser Gly Ser Gly Ser Gly Thr Asp Phe Thr Phe Thr Ile Ser Ser
                 85                  90                  95 ctc cag cca gag gac atc gcc acc tac tac tgc cag cag gat tat agc         336
Leu Gln Pro Glu Asp Ile Ala Thr Tyr Tyr Cys Gln Gln Asp Tyr Ser
             100                 105                 110 tct ccg tac acg ttc ggc caa ggg acc aag gtg gaa atc aaa cgt aag         384
Ser Pro Tyr Thr Phe Gly Gln Gly Thr Lys Val Glu Ile Lys Arg Lys
         115                 120                 125 tg                                                                      386
```

<210> SEQ ID NO 31
<211> LENGTH: 128
<212> TYPE: PRT
<213> ORGANISM: Artificial Sequence
<220> FEATURE:
<223> OTHER INFORMATION: light chain variable region

<400> SEQUENCE: 31

```
Met Gly Trp Ser Cys Ile Ile Leu Phe Leu Val Ala Thr Ala Thr Gly
 1               5                  10                  15

Val His Ser Asp Ile Gln Leu Thr Gln Ser Pro Ser Ser Leu Ser Ala
             20                  25                  30

Ser Val Gly Asp Arg Val Thr Ile Thr Cys Lys Ala Ser Gln Ser Val
         35                  40                  45

Thr Asn Asp Val Ala Trp Tyr Gln Gln Lys Pro Gly Lys Ala Pro Lys
 50                  55                  60

Leu Leu Ile Tyr Tyr Ala Ser Asn Arg Tyr Thr Gly Val Pro Ser Arg
 65                  70                  75                  80

Phe Ser Gly Ser Gly Ser Gly Thr Asp Phe Thr Phe Thr Ile Ser Ser
                 85                  90                  95

Leu Gln Pro Glu Asp Ile Ala Thr Tyr Tyr Cys Gln Gln Asp Tyr Ser
             100                 105                 110

Ser Pro Tyr Thr Phe Gly Gln Gly Thr Lys Val Glu Ile Lys Arg Lys
         115                 120                 125
```

<210> SEQ ID NO 32
<211> LENGTH: 429
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(429)

<400> SEQUENCE: 32

```
atg gac tgg acc tgg agg gtc ttc tgc ttg ctg gct gta gca cca ggt          48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga          96
Ala His Ser Gln Val Gln Leu Gln Glu Ser Gly Pro Gly Leu Val Arg
```

```
                20                  25                  30
cct agc cag acc ctg agc ctg acc tgc acc gtg tct ggc ttc aac att      144
Pro Ser Gln Thr Leu Ser Leu Thr Cys Thr Val Ser Gly Phe Asn Ile
         35                  40                  45 aaa gac acc tat atg cac tgg gtg aga cag cca cct gga cga ggt ctt      192
Lys Asp Thr Tyr Met His Trp Val Arg Gln Pro Pro Gly Arg Gly Leu
 50                  55                  60 gag tgg att gga agg att gat cct gcg agt ggc gat act aaa tat gac      240
Glu Trp Ile Gly Arg Ile Asp Pro Ala Ser Gly Asp Thr Lys Tyr Asp
 65                  70                  75                  80 ccg aag ttc cag gtc aga gtg aca atg ctg gta gac acc agc agc aac      288
Pro Lys Phe Gln Val Arg Val Thr Met Leu Val Asp Thr Ser Ser Asn
                 85                  90                  95 cag ttc agc ctg aga ctc agc agc gtg aca gcc gcc gac acc gcg gtc      336
Gln Phe Ser Leu Arg Leu Ser Ser Val Thr Ala Ala Asp Thr Ala Val
            100                 105                 110 tat tat tgt gca gac gga atg tgg gta tca acg gga tat gct ctg gac      384
Tyr Tyr Cys Ala Asp Gly Met Trp Val Ser Thr Gly Tyr Ala Leu Asp
        115                 120                 125 ttc tgg ggc caa ggg acc acg gtc acc gtc tcc tca ggt gag tcc          429
Phe Trp Gly Gln Gly Thr Thr Val Thr Val Ser Ser Gly Glu Ser
    130                 135                 140
```

<210> SEQ ID NO 33
<211> LENGTH: 143
<212> TYPE: PRT
<213> ORGANISM: Artificial Sequence
<220> FEATURE:
<223> OTHER INFORMATION: heavy chain variable region

<400> SEQUENCE: 33

```
Met Asp Trp Thr Trp Arg Val Phe Cys Leu Leu Ala Val Ala Pro Gly
 1               5                  10                  15

Ala His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Asn Ile
         35                  40                  45

Lys Asp Thr Tyr Met His Trp Val Arg Gln Pro Pro Gly Arg Gly Leu
 50                  55                  60

Glu Trp Ile Gly Arg Ile Asp Pro Ala Ser Gly Asp Thr Lys Tyr Asp
 65                  70                  75                  80

Pro Lys Phe Gln Val Arg Val Thr Met Leu Val Asp Thr Ser Ser Asn
                 85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140
```

<210> SEQ ID NO 34
<211> LENGTH: 24
<212> TYPE: DNA
<213> ORGANISM: Artificial Sequence
<220> FEATURE:
<223> OTHER INFORMATION: mutagenizing oligonucleotide

<400> SEQUENCE: 34
agacaccagc agcaaccagt tcag                                            24

```
<210> SEQ ID NO 35
<211> LENGTH: 24
<212> TYPE: DNA
<213> ORGANISM: Artificial Sequence
<220> FEATURE:
<223> OTHER INFORMATION: mutagenizing oligonucleotide

<400> SEQUENCE: 35
tgaactggtt gctgctggtg tcta                                          24

<210> SEQ ID NO 36
<211> LENGTH: 37
<212> TYPE: DNA
<213> ORGANISM: Artificial Sequence
<220> FEATURE:
<223> OTHER INFORMATION: mutagenizing oligonucleotide

<400> SEQUENCE: 36
accagcagca acacagcctg gctgagactc agcagcg                            37

<210> SEQ ID NO 37
<211> LENGTH: 38
<212> TYPE: DNA
<213> ORGANISM: Artificial Sequence
<220> FEATURE:
<223> OTHER INFORMATION: mutagenizing oligonucleotide

<400> SEQUENCE: 37
gctgagtctc agccaggctg tgttgctgct ggtgtcga                           38

<210> SEQ ID NO 38
<211> LENGTH: 429
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(429)

<400> SEQUENCE: 38 atg gac tgg acc tgg agg gtc ttc tgc ttg ctg gct gta gca cca ggt     48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga     96
Ala His Ser Gln Val Gln Leu Gln Glu Ser Gly Pro Gly Leu Val Arg
             20                  25                  30 cct agc cag acc ctg agc ctg acc tgc acc gtg tct ggc ttc aac att    144
Pro Ser Gln Thr Leu Ser Leu Thr Cys Thr Val Ser Gly Phe Asn Ile
         35                  40                  45 aaa gac acc tat atg cac tgg gtg aga cag cca cct gga cga ggt ctt    192
Lys Asp Thr Tyr Met His Trp Val Arg Gln Pro Pro Gly Arg Gly Leu
     50                  55                  60 gag tgg att gga agg att gat cct gcg agt ggc gat act aaa tat gac    240
Glu Trp Ile Gly Arg Ile Asp Pro Ala Ser Gly Asp Thr Lys Tyr Asp
 65                  70                  75                  80 ccg aag ttc cag gtc aga gtg aca atg ctg gta gac acc agc agc aac    288
Pro Lys Phe Gln Val Arg Val Thr Met Leu Val Asp Thr Ser Ser Asn
                 85                  90                  95 aca gcc tgg ctg aga ctc agc agc gtg aca gcc gcc gac acc gcg gtc    336
Thr Ala Trp Leu Arg Leu Ser Ser Val Thr Ala Ala Asp Thr Ala Val
            100                 105                 110 tat tat tgt gca gac gga atg tgg gta tca acg gga tat gct ctg gac    384
Tyr Tyr Cys Ala Asp Gly Met Trp Val Ser Thr Gly Tyr Ala Leu Asp
        115                 120                 125
```

```
ttc tgg ggc caa ggg acc acg gtc acc gtc tcc tca ggt gag tcc          429
Phe Trp Gly Gln Gly Thr Thr Val Thr Val Ser Ser Gly Glu Ser
    130                 135                 140
```

<210> SEQ ID NO 39
<211> LENGTH: 143
<212> TYPE: PRT
<213> ORGANISM: Artificial Sequence
<220> FEATURE:
<223> OTHER INFORMATION: heavy chain variable region

<400> SEQUENCE: 39

```
Met Asp Trp Thr Trp Arg Val Phe Cys Leu Leu Ala Val Ala Pro Gly
  1               5                  10                  15

Ala His Ser Gln Val Gln Leu Gln Glu Ser Gly Pro Gly Leu Val Arg
             20                  25                  30

Pro Ser Gln Thr Leu Ser Leu Thr Cys Thr Val Ser Gly Phe Asn Ile
         35                  40                  45

Lys Asp Thr Tyr Met His Trp Val Arg Gln Pro Pro Gly Arg Gly Leu
 50                  55                  60

Glu Trp Ile Gly Arg Ile Asp Pro Ala Ser Gly Asp Thr Lys Tyr Asp
 65                  70                  75                  80

Pro Lys Phe Gln Val Arg Val Thr Met Leu Val Asp Thr Ser Ser Asn
                 85                  90                  95

Thr Ala Trp Leu Arg Leu Ser Ser Val Ala Ala Asp Thr Ala Val
            100                 105                 110

Tyr Tyr Cys Ala Asp Gly Met Trp Val Ser Thr Gly Tyr Ala Leu Asp
            115                 120                 125

Phe Trp Gly Gln Gly Thr Thr Val Thr Val Ser Ser Gly Glu Ser
    130                 135                 140
```

<210> SEQ ID NO 40
<211> LENGTH: 40
<212> TYPE: DNA
<213> ORGANISM: Artificial Sequence
<220> FEATURE:
<223> OTHER INFORMATION: mutagenizing oligonucleotide

<400> SEQUENCE: 40
agttccaggt caaagcgaca attacggcag acaccagcaa          40

<210> SEQ ID NO 41
<211> LENGTH: 40
<212> TYPE: DNA
<213> ORGANISM: Artificial Sequence
<220> FEATURE:
<223> OTHER INFORMATION: mutagenizing oligonucleotide

<400> SEQUENCE: 41
cttgctggtg tctgccgtaa ttgtcgcttt gacctggaac          40

<210> SEQ ID NO 42
<211> LENGTH: 429
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(429)

<400> SEQUENCE: 42

```
atg gac tgg acc tgg agg gtc ttc tgc ttg ctg gct gta gca cca ggt    48
Met Asp Trp Thr Trp Arg Val Phe Cys Leu Leu Ala Val Ala Pro Gly
  1               5                  10                  15
```

```
                1               5                  10                  15
gcc cac tcc cag gtc caa ctg cag gag agc ggt cca ggt ctt gtg aga            96
Ala His Ser Gln Val Gln Leu Gln Glu Ser Gly Pro Gly Leu Val Arg
                20                  25                  30 cct agc cag acc ctg agc ctg acc tgc acc gtg tct ggc ttc aac att           144
Pro Ser Gln Thr Leu Ser Leu Thr Cys Thr Val Ser Gly Phe Asn Ile
            35                  40                  45 aaa gac acc tat atg cac tgg gtg aga cag cca cct gga cga ggt ctt           192
Lys Asp Thr Tyr Met His Trp Val Arg Gln Pro Pro Gly Arg Gly Leu
        50                  55                  60 gag tgg att gga agg att gat cct gcg agt ggc gat act aaa tat gac           240
Glu Trp Ile Gly Arg Ile Asp Pro Ala Ser Gly Asp Thr Lys Tyr Asp
 65                 70                  75                  80 ccg aag ttc cag gtc aaa gcg aca att acg gca gac acc agc agc aac           288
Pro Lys Phe Gln Val Lys Ala Thr Ile Thr Ala Asp Thr Ser Ser Asn
                85                  90                  95 cag ttc agc ctg aga ctc agc agc gtg aca gcc gcc gac acc gcg gtc           336
Gln Phe Ser Leu Arg Leu Ser Ser Val Thr Ala Ala Asp Thr Ala Val
                100                 105                 110 tat tat tgt gca gac gga atg tgg gta tca acg gga tat gct ctg gac           384
Tyr Tyr Cys Ala Asp Gly Met Trp Val Ser Thr Gly Tyr Ala Leu Asp
            115                 120                 125 ttc tgg ggc caa ggg acc acg gtc acc gtc tcc tca ggt gag tcc               429
Phe Trp Gly Gln Gly Thr Thr Val Thr Val Ser Ser Gly Glu Ser
        130                 135                 140
```

<210> SEQ ID NO 43
<211> LENGTH: 143
<212> TYPE: PRT
<213> ORGANISM: Artificial Sequence
<220> FEATURE:
<223> OTHER INFORMATION: heavy chain variable region

<400> SEQUENCE: 43

```
Met Asp Trp Thr Trp Arg Val Phe Cys Leu Leu Ala Val Ala Pro Gly
 1               5                  10                  15

Ala His Ser Gln Val Gln Leu Gln Glu Ser Gly Pro Gly Leu Val Arg
                20                  25                  30

Pro Ser Gln Thr Leu Ser Leu Thr Cys Thr Val Ser Gly Phe Asn Ile
            35                  40                  45

Lys Asp Thr Tyr Met His Trp Val Arg Gln Pro Pro Gly Arg Gly Leu
        50                  55                  60

Glu Trp Ile Gly Arg Ile Asp Pro Ala Ser Gly Asp Thr Lys Tyr Asp
 65                 70                  75                  80

Pro Lys Phe Gln Val Lys Ala Thr Ile Thr Ala Asp Thr Ser Ser Asn
                85                  90                  95

Gln Phe Ser Leu Arg Leu Ser Ser Val Thr Ala Ala Asp Thr Ala Val
                100                 105                 110

Tyr Tyr Cys Ala Asp Gly Met Trp Val Ser Thr Gly Tyr Ala Leu Asp
            115                 120                 125

Phe Trp Gly Gln Gly Thr Thr Val Thr Val Ser Ser Gly Glu Ser
        130                 135                 140
```

<210> SEQ ID NO 44
<211> LENGTH: 36
<212> TYPE: DNA
<213> ORGANISM: Artificial Sequence
<220> FEATURE:
<223> OTHER INFORMATION: mutagenizing oligonucleotide

<400> SEQUENCE: 44

-continued

```
ctcagcagcg tgacatctga ggacaccgcg gtctat                              36
```

<210> SEQ ID NO 45
<211> LENGTH: 36
<212> TYPE: DNA
<213> ORGANISM: Artificial Sequence
<220> FEATURE:
<223> OTHER INFORMATION: mutagenizing oligonucleotide

<400> SEQUENCE: 45

```
atagaccgcg gtgtcctcag atgtcacgct gctgag                              36
```

<210> SEQ ID NO 46
<211> LENGTH: 372
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(372)

<400> SEQUENCE: 46

```
cag gtc caa ctg cag gag agc ggt cca ggt ctt gtg aga cct agc cag     48
Gln Val Gln Leu Gln Glu Ser Gly Pro Gly Leu Val Arg Pro Ser Gln
1               5                   10                  15 acc ctg agc ctg acc tgc acc gtg tct ggc ttc aac att aaa gac acc     96
Thr Leu Ser Leu Thr Cys Thr Val Ser Gly Phe Asn Ile Lys Asp Thr
            20                  25                  30 tat atg cac tgg gtg aga cag cca cct gga cga ggt ctt gag tgg att    144
Tyr Met His Trp Val Arg Gln Pro Pro Gly Arg Gly Leu Glu Trp Ile
        35                  40                  45 gga agg att gat cct gcg agt ggc gat act aaa tat gac ccg aag ttc    192
Gly Arg Ile Asp Pro Ala Ser Gly Asp Thr Lys Tyr Asp Pro Lys Phe
    50                  55                  60 cag gtc aga gtg aca atg ctg gta gac acc agc agc aac cag ttc agc    240
Gln Val Arg Val Thr Met Leu Val Asp Thr Ser Ser Asn Gln Phe Ser
65                  70                  75                  80 ctg aga ctc agc agc gtg aca tct gag gac acc gcg gtc tat tat tgt    288
Leu Arg Leu Ser Ser Val Thr Ser Glu Asp Thr Ala Val Tyr Tyr Cys
                85                  90                  95 gca gac gga atg tgg gta tca acg gga tat gct ctg gac ttc tgg ggc    336
Ala Asp Gly Met Trp Val Ser Thr Gly Tyr Ala Leu Asp Phe Trp Gly
            100                 105                 110 caa ggg acc acg gtc acc gtc tcc tca ggt gag tcc                    372
Gln Gly Thr Thr Val Thr Val Ser Ser Gly Glu Ser
        115                 120
```

<210> SEQ ID NO 47
<211> LENGTH: 124
<212> TYPE: PRT
<213> ORGANISM: Artificial Sequence
<220> FEATURE:
<223> OTHER INFORMATION: heavy chain variable region

<400> SEQUENCE: 47

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Phe Asn Ile Lys Asp Thr
            20                  25                  30

Tyr Met His Trp Val Arg Gln Pro Pro Gly Arg Gly Leu Glu Trp Ile
        35                  40                  45

Gly Arg Ile Asp Pro Ala Ser Gly Asp Thr Lys Tyr Asp Pro Lys Phe
```

```
                    50                  55                  60
Gln Val Arg Val Thr Met Leu Val Asp Thr Ser Ser Asn Gln Phe Ser
 65                  70                  75                  80

Leu Arg Leu Ser Ser Val Thr Ser Glu Asp Thr Ala Val Tyr Tyr Cys
                 85                  90                  95

Ala Asp Gly Met Trp Val Ser Thr Gly Tyr Ala Leu Asp Phe Trp Gly
            100                 105                 110

Gln Gly Thr Thr Val Thr Val Ser Ser Gly Glu Ser
        115                 120

<210> SEQ ID NO 48
<211> LENGTH: 31
<212> TYPE: DNA
<213> ORGANISM: Artificial Sequence
<220> FEATURE:
<223> OTHER INFORMATION: mutagenizing oligonucleotide

<400> SEQUENCE: 48
tgcactgggt gaaacagcga cctggacgag g                                   31

<210> SEQ ID NO 49
<211> LENGTH: 31
<212> TYPE: DNA
<213> ORGANISM: Artificial Sequence
<220> FEATURE:
<223> OTHER INFORMATION: mutagenizing oligonucleotide

<400> SEQUENCE: 49
cctcgtccag gtcgctgttt cacccagtgc a                                   31

<210> SEQ ID NO 50
<211> LENGTH: 429
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(429)

<400> SEQUENCE: 50 atg gac tgg acc tgg agg gtc ttc tgc ttg ctg gct gta gca cca ggt     48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga     96
Ala His Ser Gln Val Gln Leu Gln Glu Ser Gly Pro Gly Leu Val Arg
                20                  25                  30 cct agc cag acc ctg agc ctg acc tgc acc gtg tct ggc ttc aac att    144
Pro Ser Gln Thr Leu Ser Leu Thr Cys Thr Val Ser Gly Phe Asn Ile
            35                  40                  45 aaa gac acc tat atg cac tgg gtg aaa cag cga cct gga cga ggt ctt    192
Lys Asp Thr Tyr Met His Trp Val Lys Gln Arg Pro Gly Arg Gly Leu
        50                  55                  60 gag tgg att gga agg att gat cct gcg agt ggc gat act aaa tat gac    240
Glu Trp Ile Gly Arg Ile Asp Pro Ala Ser Gly Asp Thr Lys Tyr Asp
 65                  70                  75                  80 ccg aag ttc cag gtc aga gtg aca atg ctg gta gac acc agc agc aac    288
Pro Lys Phe Gln Val Arg Val Thr Met Leu Val Asp Thr Ser Ser Asn
                 85                  90                  95 cag ttc agc ctg aga ctc agc agc gtg aca gcc gcc gac acc gcg gtc    336
Gln Phe Ser Leu Arg Leu Ser Ser Val Thr Ala Ala Asp Thr Ala Val
            100                 105                 110 tat tat tgt gca gac gga atg tgg gta tca acg gga tat gct ctg gac    384
Tyr Tyr Cys Ala Asp Gly Met Trp Val Ser Thr Gly Tyr Ala Leu Asp
```

```
Tyr Tyr Cys Ala Asp Gly Met Trp Val Ser Thr Gly Tyr Ala Leu Asp
        115                 120                 125
ttc tgg ggc caa ggg acc acg gtc acc gtc tcc tca ggt gag tcc       429
Phe Trp Gly Gln Gly Thr Thr Val Thr Val Ser Ser Gly Glu Ser
130                 135                 140
```

<210> SEQ ID NO 51
<211> LENGTH: 143
<212> TYPE: PRT
<213> ORGANISM: Artificial Sequence
<220> FEATURE:
<223> OTHER INFORMATION: heavy chain variable region

<400> SEQUENCE: 51

```
Met Asp Trp Thr Trp Arg Val Phe Cys Leu Leu Ala Val Ala Pro Gly
 1               5                   10                  15

Ala His Ser Gln Val Gln Leu Gln Glu Ser Gly Pro Gly Leu Val Arg
            20                  25                  30

Pro Ser Gln Thr Leu Ser Leu Thr Cys Thr Val Ser Gly Phe Asn Ile
        35                  40                  45

Lys Asp Thr Tyr Met His Trp Val Lys Gln Arg Pro Gly Arg Gly Leu
 50                  55                  60

Glu Trp Ile Gly Arg Ile Asp Pro Ala Ser Gly Asp Thr Lys Tyr Asp
65                  70                  75                  80

Pro Lys Phe Gln Val Arg Val Thr Met Leu Val Asp Thr Ser Ser Asn
                85                  90                  95

Gln Phe Ser Leu Arg Leu Ser Ser Val Thr Ala Ala Asp Thr Ala Val
            100                 105                 110

Tyr Tyr Cys Ala Asp Gly Met Trp Val Ser Thr Gly Tyr Ala Leu Asp
        115                 120                 125

Phe Trp Gly Gln Gly Thr Thr Val Thr Val Ser Ser Gly Glu Ser
    130                 135                 140
```

<210> SEQ ID NO 52
<211> LENGTH: 26
<212> TYPE: DNA
<213> ORGANISM: Artificial Sequence
<220> FEATURE:
<223> OTHER INFORMATION: mutagenizing oligonucleotide

<400> SEQUENCE: 52
tgacctgcac cgcgtctggc ttcaac                                       26

<210> SEQ ID NO 53
<211> LENGTH: 26
<212> TYPE: DNA
<213> ORGANISM: Artificial Sequence
<220> FEATURE:
<223> OTHER INFORMATION: mutagenizing oligonucleotide

<400> SEQUENCE: 53
ttgaagccag acgcggtgca ggtcag                                       26

<210> SEQ ID NO 54
<211> LENGTH: 429
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(429)

<400> SEQUENCE: 54

```
atg gac tgg acc tgg agg gtc ttc tgc ttg ctg gct gta gca cca ggt      48
Met Asp Trp Thr Trp Arg Val Phe Cys Leu Leu Ala Val Ala Pro Gly
 1               5                  10                  15 gcc cac tcc cag gtc caa ctg cag gag agc ggt cca ggt ctt gtg aga      96
Ala His Ser Gln Val Gln Leu Gln Glu Ser Gly Pro Gly Leu Val Arg
                20                  25                  30 cct agc cag acc ctg agc ctg acc tgc acc gcg tct ggc ttc aac att     144
Pro Ser Gln Thr Leu Ser Leu Thr Cys Thr Ala Ser Gly Phe Asn Ile
            35                  40                  45 aaa gac acc tat atg cac tgg gtg aga cag cca cct gga cga ggt ctt     192
Lys Asp Thr Tyr Met His Trp Val Arg Gln Pro Pro Gly Arg Gly Leu
 50                  55                  60 gag tgg att gga agg att gat cct gcg agt ggc gat act aaa tat gac     240
Glu Trp Ile Gly Arg Ile Asp Pro Ala Ser Gly Asp Thr Lys Tyr Asp
 65                  70                  75                  80 ccg aag ttc cag gtc aga gtg aca atg ctg gta gac acc agc agc aac     288
Pro Lys Phe Gln Val Arg Val Thr Met Leu Val Asp Thr Ser Ser Asn
                85                  90                  95 cag ttc agc ctg aga ctc agc agc gtg aca gcc gcc gac acc gcg gtc     336
Gln Phe Ser Leu Arg Leu Ser Ser Val Thr Ala Ala Asp Thr Ala Val
               100                 105                 110 tat tat tgt gca gac gga atg tgg gta tca acg gga tat gct ctg gac     384
Tyr Tyr Cys Ala Asp Gly Met Trp Val Ser Thr Gly Tyr Ala Leu Asp
           115                 120                 125 ttc tgg ggc caa ggg acc acg gtc acc gtc tcc tca ggt gag tcc         429
Phe Trp Gly Gln Gly Thr Thr Val Thr Val Ser Ser Gly Glu Ser
           130                 135                 140
```

<210> SEQ ID NO 55
<211> LENGTH: 143
<212> TYPE: PRT
<213> ORGANISM: Artificial Sequence
<220> FEATURE:
<223> OTHER INFORMATION: heavy chain variable region

<400> SEQUENCE: 55

```
Met Asp Trp Thr Trp Arg Val Phe Cys Leu Leu Ala Val Ala Pro Gly
 1               5                  10                  15

Ala His Ser Gln Val Gln Leu Gln Glu Ser Gly Pro Gly Leu Val Arg
                20                  25                  30

Pro Ser Gln Thr Leu Ser Leu Thr Cys Thr Ala Ser Gly Phe Asn Ile
            35                  40                  45

Lys Asp Thr Tyr Met His Trp Val Arg Gln Pro Pro Gly Arg Gly Leu
 50                  55                  60

Glu Trp Ile Gly Arg Ile Asp Pro Ala Ser Gly Asp Thr Lys Tyr Asp
 65                  70                  75                  80

Pro Lys Phe Gln Val Arg Val Thr Met Leu Val Asp Thr Ser Ser Asn
                85                  90                  95

Gln Phe Ser Leu Arg Leu Ser Ser Val Thr Ala Ala Asp Thr Ala Val
               100                 105                 110

Tyr Tyr Cys Ala Asp Gly Met Trp Val Ser Thr Gly Tyr Ala Leu Asp
           115                 120                 125

Phe Trp Gly Gln Gly Thr Thr Val Thr Val Ser Ser Gly Glu Ser
           130                 135                 140
```

<210> SEQ ID NO 56
<211> LENGTH: 29
<212> TYPE: DNA
<213> ORGANISM: Artificial Sequence
<220> FEATURE:

<223> OTHER INFORMATION: mutagenizing oligonucleotide

<400> SEQUENCE: 56
tattattgtg caagaggaat gtgggtatc                                29

<210> SEQ ID NO 57
<211> LENGTH: 29
<212> TYPE: DNA
<213> ORGANISM: Artificial Sequence
<220> FEATURE:
<223> OTHER INFORMATION: mutagenizing oligonucleotide

<400> SEQUENCE: 57
atacccacat tcctcttgca caataatag                                29

<210> SEQ ID NO 58
<211> LENGTH: 41
<212> TYPE: DNA
<213> ORGANISM: Artificial Sequence
<220> FEATURE:
<223> OTHER INFORMATION: mutagenizing oligonucleotide

<400> SEQUENCE: 58
ctgcaccgtg tctggcttca ccttcagcga cacctatatg c                  41

<210> SEQ ID NO 59
<211> LENGTH: 41
<212> TYPE: DNA
<213> ORGANISM: Artificial Sequence
<220> FEATURE:
<223> OTHER INFORMATION: mutagenizing oligonucleotide

<400> SEQUENCE: 59
gcatataggt gtcgctgaag gtgaagccag acacggtgca g                  41

<210> SEQ ID NO 60
<211> LENGTH: 31
<212> TYPE: DNA
<213> ORGANISM: Artificial Sequence
<220> FEATURE:
<223> OTHER INFORMATION: mutagenizing oligonucleotide

<400> SEQUENCE: 60
ggtgtccact ccagcatcgt gatgacccag a                             31

<210> SEQ ID NO 61
<211> LENGTH: 31
<212> TYPE: DNA
<213> ORGANISM: Artificial Sequence
<220> FEATURE:
<223> OTHER INFORMATION: mutagenizing oligonucleotide

<400> SEQUENCE: 61
tctgggtcat cacgatgctg gagtggacac c                             31

<210> SEQ ID NO 62
<211> LENGTH: 386
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)...(384)

<400> SEQUENCE: 62 atg ggt tgg tcc tgc atc atc ctg ttc ctg gtt gct acc gct acc ggt    48

```
Met Gly Trp Ser Cys Ile Ile Leu Phe Leu Val Ala Thr Ala Thr Gly
 1               5                  10                  15 gtc cac tcc agc atc gtg atg acc cag agc cca agc agc ctg agc gcc      96
Val His Ser Ser Ile Val Met Thr Gln Ser Pro Ser Ser Leu Ser Ala
                 20                  25                  30 agc gtg ggt gac aga gtg acc atc acc tgt aag gcc agt cag agt gtg     144
Ser Val Gly Asp Arg Val Thr Ile Thr Cys Lys Ala Ser Gln Ser Val
             35                  40                  45 act aat gat gta gct tgg tac cag cag aag cca ggt aag gct cca aag     192
Thr Asn Asp Val Ala Trp Tyr Gln Gln Lys Pro Gly Lys Ala Pro Lys
         50                  55                  60 ctg ctg atc tac tat gca tcc aat cgc tac act ggt gtg cca gat aga     240
Leu Leu Ile Tyr Tyr Ala Ser Asn Arg Tyr Thr Gly Val Pro Asp Arg
65                  70                  75                  80 ttc agc ggt agc ggt tat ggt acc gac ttc acc ttc acc atc agc agc     288
Phe Ser Gly Ser Gly Tyr Gly Thr Asp Phe Thr Phe Thr Ile Ser Ser
                 85                  90                  95 ctc cag cca gag gac atc gcc acc tac tac tgc cag cag gat tat agc     336
Leu Gln Pro Glu Asp Ile Ala Thr Tyr Tyr Cys Gln Gln Asp Tyr Ser
            100                 105                 110 tct ccg tac acg ttc ggc caa ggg acc aag gtg gaa atc aaa cgt aag     384
Ser Pro Tyr Thr Phe Gly Gln Gly Thr Lys Val Glu Ile Lys Arg Lys
        115                 120                 125 tg                                                                   386

<210> SEQ ID NO 63
<211> LENGTH: 128
<212> TYPE: PRT
<213> ORGANISM: Artificial Sequence
<220> FEATURE:
<223> OTHER INFORMATION: light chain variable region

<400> SEQUENCE: 63

Met Gly Trp Ser Cys Ile Ile Leu Phe Leu Val Ala Thr Ala Thr Gly
 1               5                  10                  15

Val His Ser Ser Ile Val Met Thr Gln Ser Pro Ser Ser Leu Ser Ala
                 20                  25                  30

Ser Val Gly Asp Arg Val Thr Ile Thr Cys Lys Ala Ser Gln Ser Val
             35                  40                  45

Thr Asn Asp Val Ala Trp Tyr Gln Gln Lys Pro Gly Lys Ala Pro Lys
         50                  55                  60

Leu Leu Ile Tyr Tyr Ala Ser Asn Arg Tyr Thr Gly Val Pro Asp Arg
65                  70                  75                  80

Phe Ser Gly Ser Gly Tyr Gly Thr Asp Phe Thr Phe Thr Ile Ser Ser
                 85                  90                  95

Leu Gln Pro Glu Asp Ile Ala Thr Tyr Tyr Cys Gln Gln Asp Tyr Ser
            100                 105                 110

Ser Pro Tyr Thr Phe Gly Gln Gly Thr Lys Val Glu Ile Lys Arg Lys
        115                 120                 125

<210> SEQ ID NO 64
<211> LENGTH: 32
<212> TYPE: DNA
<213> ORGANISM: Artificial Sequence
<220> FEATURE:
<223> OTHER INFORMATION: mutagenizing oligonucleotide

<400> SEQUENCE: 64
ggtgtccact ccgacatcca gatgacccag ag                                  32
```

```
<210> SEQ ID NO 65
<211> LENGTH: 32
<212> TYPE: DNA
<213> ORGANISM: Artificial Sequence
<220> FEATURE:
<223> OTHER INFORMATION: mutagenizing oligonucleotide

<400> SEQUENCE: 65
ctctgggtca tctggatgtc ggagtggaca cc                              32

<210> SEQ ID NO 66
<211> LENGTH: 386
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)...(384)

<400> SEQUENCE: 66 atg ggt tgg tcc tgc atc atc ctg ttc ctg gtt gct acc gct acc ggt      48
Met Gly Trp Ser Cys Ile Ile Leu Phe Leu Val Ala Thr Ala Thr Gly
 1               5                   10                  15 gtc cac tcc gac atc cag atg acc cag agc cca agc agc ctg agc gcc      96
Val His Ser Asp Ile Gln Met Thr Gln Ser Pro Ser Ser Leu Ser Ala
             20                  25                  30 agc gtg ggt gac aga gtg acc atc acc tgt aag gcc agt cag agt gtg     144
Ser Val Gly Asp Arg Val Thr Ile Thr Cys Lys Ala Ser Gln Ser Val
         35                  40                  45 act aat gat gta gct tgg tac cag cag aag cca ggt aag gct cca aag     192
Thr Asn Asp Val Ala Trp Tyr Gln Gln Lys Pro Gly Lys Ala Pro Lys
     50                  55                  60 ctg ctg atc tac tat gca tcc aat cgc tac act ggt gtg cca gat aga     240
Leu Leu Ile Tyr Tyr Ala Ser Asn Arg Tyr Thr Gly Val Pro Asp Arg
 65                  70                  75                  80 ttc agc ggt agc ggt tat ggt acc gac ttc acc ttc acc atc agc agc     288
Phe Ser Gly Ser Gly Tyr Gly Thr Asp Phe Thr Phe Thr Ile Ser Ser
                 85                  90                  95 ctc cag cca gag gac atc gcc acc tac tac tgc cag cag gat tat agc     336
Leu Gln Pro Glu Asp Ile Ala Thr Tyr Tyr Cys Gln Gln Asp Tyr Ser
            100                 105                 110 tct ccg tac acg ttc ggc caa ggg acc aag gtg gaa atc aaa cgt aag     384
Ser Pro Tyr Thr Phe Gly Gln Gly Thr Lys Val Glu Ile Lys Arg Lys
        115                 120                 125 tg                                                                  386

<210> SEQ ID NO 67
<211> LENGTH: 128
<212> TYPE: PRT
<213> ORGANISM: Artificial Sequence
<220> FEATURE:
<223> OTHER INFORMATION: light chain variable region

<400> SEQUENCE: 67

Met Gly Trp Ser Cys Ile Ile Leu Phe Leu Val Ala Thr Ala Thr Gly
 1               5                   10                  15

Val His Ser Asp Ile Gln Met Thr Gln Ser Pro Ser Ser Leu Ser Ala
             20                  25                  30

Ser Val Gly Asp Arg Val Thr Ile Thr Cys Lys Ala Ser Gln Ser Val
         35                  40                  45

Thr Asn Asp Val Ala Trp Tyr Gln Gln Lys Pro Gly Lys Ala Pro Lys
     50                  55                  60
```

```
Leu Leu Ile Tyr Tyr Ala Ser Asn Arg Tyr Thr Gly Val Pro Asp Arg
 65                  70                  75                  80

Phe Ser Gly Ser Gly Tyr Gly Thr Asp Phe Thr Phe Thr Ile Ser Ser
                 85                  90                  95

Leu Gln Pro Glu Asp Ile Ala Thr Tyr Tyr Cys Gln Gln Asp Tyr Ser
            100                 105                 110

Ser Pro Tyr Thr Phe Gly Gln Gly Thr Lys Val Glu Ile Lys Arg Lys
        115                 120                 125
```

```
<210> SEQ ID NO 68
<211> LENGTH: 429
<212> TYPE: DNA
<213> ORGANISM: Artificial Sequence
<220> FEATURE:
<223> OTHER INFORMATION: heavy chain variable region
<220> FEATURE:
<221> NAME/KEY: CDS
<222> LOCATION: (1)...(429)

<400> SEQUENCE: 68
```

```
atg gac tgg acc tgg agg gtc ttc tgc ttg ctg gct gta gca cca ggt    48
Met Asp Trp Thr Trp Arg Val Phe Cys Leu Leu Ala Val Ala Pro Gly
 1               5                  10                  15 gcc cac tcc cag gtc caa ctg cag gag tcc ggt gct gaa gtt gtt aaa    96
Ala His Ser Gln Val Gln Leu Gln Glu Ser Gly Ala Glu Val Val Lys
             20                  25                  30 ccg ggt tcc tcc gtt aaa ctg tcc tgc aaa gct tcc ggt ttc aac atc   144
Pro Gly Ser Ser Val Lys Leu Ser Cys Lys Ala Ser Gly Phe Asn Ile
         35                  40                  45 aaa gac acc tac atg cac tgg gtt aaa cag cgt ccg ggt cag ggt ctg   192
Lys Asp Thr Tyr Met His Trp Val Lys Gln Arg Pro Gly Gln Gly Leu
     50                  55                  60 gaa tgg atc ggt cgt atc gac ccg gct tcc ggt gac acc aaa tac gac   240
Glu Trp Ile Gly Arg Ile Asp Pro Ala Ser Gly Asp Thr Lys Tyr Asp
 65                  70                  75                  80 ccg aaa ttc cag gtt aaa gct acc atc acc gct gac gaa tcc acc tcc   288
Pro Lys Phe Gln Val Lys Ala Thr Ile Thr Ala Asp Glu Ser Thr Ser
                 85                  90                  95 acc gct tac ctg gaa ctg tcc tcc ctg cgt tcc gaa gac acc gct gtt   336
Thr Ala Tyr Leu Glu Leu Ser Ser Leu Arg Ser Glu Asp Thr Ala Val
            100                 105                 110 tac tac tgc gct gac ggt atg tgg gtt tcc acc ggt tac gct ctg gac   384
Tyr Tyr Cys Ala Asp Gly Met Trp Val Ser Thr Gly Tyr Ala Leu Asp
        115                 120                 125 ttc tgg ggt cag ggt acc acg gtc acc gtc tcc tca ggt gag tcc       429
Phe Trp Gly Gln Gly Thr Thr Val Thr Val Ser Ser Gly Glu Ser
    130                 135                 140
```

```
<210> SEQ ID NO 69
<211> LENGTH: 143
<212> TYPE: PRT
<213> ORGANISM: Artificial Sequence
<220> FEATURE:
<223> OTHER INFORMATION: heavy chain variable region

<400> SEQUENCE: 69
```

```
Met Asp Trp Thr Trp Arg Val Phe Cys Leu Leu Ala Val Ala Pro Gly
 1               5                  10                  15

Ala His Ser Gln Val Gln Leu Gln Glu Ser Gly Ala Glu Val Val Lys
             20                  25                  30

Pro Gly Ser Ser Val Lys Leu Ser Cys Lys Ala Ser Gly Phe Asn Ile
         35                  40                  45
```

```
Lys Asp Thr Tyr Met His Trp Val Lys Gln Arg Pro Gly Gln Gly Leu
 50                  55                  60

Glu Trp Ile Gly Arg Ile Asp Pro Ala Ser Gly Asp Thr Lys Tyr Asp
 65                  70                  75                  80

Pro Lys Phe Gln Val Lys Ala Thr Ile Thr Ala Asp Glu Ser Thr Ser
             85                  90                  95

Thr Ala Tyr Leu Glu Leu Ser Ser Leu Arg Ser Glu Asp Thr Ala Val
            100                 105                 110

Tyr Tyr Cys Ala Asp Gly Met Trp Val Ser Thr Gly Tyr Ala Leu Asp
            115                 120                 125

Phe Trp Gly Gln Gly Thr Thr Val Thr Val Ser Ser Gly Glu Ser
130                 135                 140
```

<210> SEQ ID NO 70
<211> LENGTH: 383
<212> TYPE: DNA
<213> ORGANISM: Artificial Sequence
<220> FEATURE:
<223> OTHER INFORMATION: light chain variable region
<220> FEATURE:
<221> NAME/KEY: CDS
<222> LOCATION: (1)...(372)

<400> SEQUENCE: 70

```
atg ggt tgg tcc tgc atc atc ctg ttc ctg gtt gct acc gct acc ggt     48
Met Gly Trp Ser Cys Ile Ile Leu Phe Leu Val Ala Thr Ala Thr Gly
 1               5                  10                  15 gtt cac tcc atc gtt atg acc cag tcc ccg gac tcc ctg gct gtt tcc     96
Val His Ser Ile Val Met Thr Gln Ser Pro Asp Ser Leu Ala Val Ser
             20                  25                  30 ctg ggt gaa cgt gtt acc atc aac tgc aaa gct tcc cag tcc gtt acc    144
Leu Gly Glu Arg Val Thr Ile Asn Cys Lys Ala Ser Gln Ser Val Thr
         35                  40                  45 aac gac gtt gct tgg tac cag cag aaa ccg ggt cag tcc ccg aaa ctg    192
Asn Asp Val Ala Trp Tyr Gln Gln Lys Pro Gly Gln Ser Pro Lys Leu
     50                  55                  60 ctg atc tac tac gct tcc aac cgt tac acc ggt gtt ccg gac cgt ttc    240
Leu Ile Tyr Tyr Ala Ser Asn Arg Tyr Thr Gly Val Pro Asp Arg Phe
 65                  70                  75                  80 tcc ggt tcc ggt tac ggt acc gac ttc acc ttc acc atc tcc tcc gtt    288
Ser Gly Ser Gly Tyr Gly Thr Asp Phe Thr Phe Thr Ile Ser Ser Val
             85                  90                  95 cag gct gaa gac gtt gct gtt tac tac tgc cag cag gac tac tcc tcc    336
Gln Ala Glu Asp Val Ala Val Tyr Tyr Cys Gln Gln Asp Tyr Ser Ser
        100                 105                 110 ccg tac acc ttc ggt ggt ggt acc aaa ctg gag atc taaggatcct         382
Pro Tyr Thr Phe Gly Gly Gly Thr Lys Leu Glu Ile
        115                 120 c                                                                  383
```

<210> SEQ ID NO 71
<211> LENGTH: 124
<212> TYPE: PRT
<213> ORGANISM: Artificial Sequence
<220> FEATURE:
<223> OTHER INFORMATION: light chain variable region

<400> SEQUENCE: 71

```
Met Gly Trp Ser Cys Ile Ile Leu Phe Leu Val Ala Thr Ala Thr Gly
 1               5                  10                  15

Val His Ser Ile Val Met Thr Gln Ser Pro Asp Ser Leu Ala Val Ser
             20                  25                  30
```

```
Leu Gly Glu Arg Val Thr Ile Asn Cys Lys Ala Ser Gln Ser Val Thr
                35                  40                  45

Asn Asp Val Ala Trp Tyr Gln Gln Lys Pro Gly Gln Ser Pro Lys Leu
         50                  55                  60

Leu Ile Tyr Tyr Ala Ser Asn Arg Tyr Thr Gly Val Pro Asp Arg Phe
 65                  70                  75                  80

Ser Gly Ser Gly Tyr Gly Thr Asp Phe Thr Phe Thr Ile Ser Ser Val
                 85                  90                  95

Gln Ala Glu Asp Val Ala Val Tyr Tyr Cys Gln Gln Asp Tyr Ser Ser
            100                 105                 110

Pro Tyr Thr Phe Gly Gly Gly Thr Lys Leu Glu Ile
            115                 120
```

<210> SEQ ID NO 72
<211> LENGTH: 60
<212> TYPE: DNA
<213> ORGANISM: Artificial Sequence
<220> FEATURE:
<223> OTHER INFORMATION: oligonucleotide for vector construction

<400> SEQUENCE: 72
caggttcagc tgcaggagtc cggtgctgaa gttgttaaac cgggttcctc cgttaaactg    60

<210> SEQ ID NO 73
<211> LENGTH: 60
<212> TYPE: DNA
<213> ORGANISM: Artificial Sequence
<220> FEATURE:
<223> OTHER INFORMATION: oligonucleotide for vector construction

<400> SEQUENCE: 73
tcctgcaaag cttccggttt caacatcaaa gacacctaca tgcactgggt taaacagcgt    60

<210> SEQ ID NO 74
<211> LENGTH: 60
<212> TYPE: DNA
<213> ORGANISM: Artificial Sequence
<220> FEATURE:
<223> OTHER INFORMATION: oligonucleotide for vector construction

<400> SEQUENCE: 74
ccgggtcagg gtctggaatg gatcggtcgt atcgacccgg cttccggtga caccaaatac    60

<210> SEQ ID NO 75
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 75
gacccgaaat tccaggttaa agctaccatc accgctgacg aatccacctc caccgcttac    60
ctggaa                                                              66

<210> SEQ ID NO 76
<211> LENGTH: 63
<212> TYPE: DNA
<213> ORGANISM: Artificial Sequence
<220> FEATURE:
<223> OTHER INFORMATION: oligonucleotide for vector construction

<400> SEQUENCE: 76
ctgtcctccc tgcgttccga agacaccgct gtttactact gcgctgacgg tatgtgggtt    60
tcc                                                                63

<210> SEQ ID NO 77
<211> LENGTH: 54
<212> TYPE: DNA
<213> ORGANISM: Artificial Sequence
<220> FEATURE:
<223> OTHER INFORMATION: oligonucleotide for vector construction

<400> SEQUENCE: 77
accggttacg ctctggactt ctggggtcag ggtaccacgg tcaccgtttc ctcc        54

<210> SEQ ID NO 78
<211> LENGTH: 63
<212> TYPE: DNA
<213> ORGANISM: Artificial Sequence
<220> FEATURE:
<223> OTHER INFORMATION: oligonucleotide for vector construction

<400> SEQUENCE: 78
ggaggaaacg gtgaccgtgg taccctgacc ccagaagtcc agagcgtaac cggtggaaac  60
cca                                                                63

<210> SEQ ID NO 79
<211> LENGTH: 47
<212> TYPE: DNA
<213> ORGANISM: Artificial Sequence
<220> FEATURE:
<223> OTHER INFORMATION: oligonucleotide for vector construction

<400> SEQUENCE: 79
cataccgtca gcgcagtagt aaacagcggt gtcttcggaa cgcaggg                47

<210> SEQ ID NO 80
<211> LENGTH: 67
<212> TYPE: DNA
<213> ORGANISM: Artificial Sequence
<220> FEATURE:
<223> OTHER INFORMATION: oligonucleotide for vector construction

<400> SEQUENCE: 80
aggacagttc caggtaagcg gtggaggtgg attcgtcagc ggtgatggta gctttaacct  60
ggaattt                                                            67

<210> SEQ ID NO 81
<211> LENGTH: 60
<212> TYPE: DNA
<213> ORGANISM: Artificial Sequence
<220> FEATURE:
<223> OTHER INFORMATION: oligonucleotide for vector construction

<400> SEQUENCE: 81
cgggtcgtat ttggtgtcac cggaagccgg gtcgatacga ccgatccatt ccagaccctg  60

<210> SEQ ID NO 82
<211> LENGTH: 60
<212> TYPE: DNA
<213> ORGANISM: Artificial Sequence
<220> FEATURE:
<223> OTHER INFORMATION: oligonucleotide for vector construction

<400> SEQUENCE: 82
acccggacgc tgtttaaccc agtgcatgta ggtgtctttg atgttgaaac cggaagcttt  60

```
<210> SEQ ID NO 83
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 83
gcaggacagt taacggagg aacccggttt aacaacttca gcaccggact cctgcagctg      60
aacctg                                                                66

<210> SEQ ID NO 84
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 84
agcttaccat gggttggtcc tgcatcatcc tgttcctggt tgctaccgct accggtgttc      60
actcca                                                                66

<210> SEQ ID NO 85
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 85
tcgttatgac ccagtccccg gactccctgg ctgtttccct gggtgaacgt gttaccatca      60
actgca                                                                66

<210> SEQ ID NO 86
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 86
aagcttccca gtccgttacc aacgacgttg cttggtacca gcagaaaccg ggtcagtccc      60
cgaaac                                                                66

<210> SEQ ID NO 87
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 87
tgctgatcta ctacgcttcc aaccgttaca ccggtgttcc ggaccgtttc tccggttccg      60
gttacg                                                                66

<210> SEQ ID NO 88
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 88
gtaccgactt caccttcacc atctcctccg ttcaggctga agacgttgct gtttactact      60
```

```
gccagc                                                              66

<210> SEQ ID NO 89
<211> LENGTH: 54
<212> TYPE: DNA
<213> ORGANISM: Artificial Sequence
<220> FEATURE:
<223> OTHER INFORMATION: oligonucleotide for vector construction

<400> SEQUENCE: 89
aggactactc ctccccgtac accttcggtg gtggtaccaa actggagatc taag         54

<210> SEQ ID NO 90
<211> LENGTH: 63
<212> TYPE: DNA
<213> ORGANISM: Artificial Sequence
<220> FEATURE:
<223> OTHER INFORMATION: oligonucleotide for vector construction

<400> SEQUENCE: 90
gatccttaga tctccagttt ggtaccacca ccgaaggtgt acggggagga gtagtcctgc   60
tgg                                                                 63

<210> SEQ ID NO 91
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 91
cagtagtaaa cagcaacgtc ttcagcctga acggaggaga tggtgaaggt gaagtcggta   60
ccgtaa                                                              66

<210> SEQ ID NO 92
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 92
ccggaaccgg agaaacggtc cggaacaccg gtgtaacggt tggaagcgta gtagatcagc   60
agtttc                                                              66

<210> SEQ ID NO 93
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 93
ggggactgac ccggtttctg ctggtaccaa gcaacgtcgt tggtaacgga ctgggaagct   60
ttgcag                                                              66

<210> SEQ ID NO 94
<211> LENGTH: 66
<212> TYPE: DNA
<213> ORGANISM: Artificial Sequence
<220> FEATURE:
<223> OTHER INFORMATION: oligonucleotide for vector construction

<400> SEQUENCE: 94
```

```
ttgatggtaa cacgttcacc cagggaaaca gccagggagt ccggggactg ggtcataacg      60
atggag                                                                66
```

<210> SEQ ID NO 95
<211> LENGTH: 57
<212> TYPE: DNA
<213> ORGANISM: Artificial Sequence
<220> FEATURE:
<223> OTHER INFORMATION: oligonucleotide for vector construction

<400> SEQUENCE: 95

```
tgaacaccgg tagcggtagc aaccaggaac aggatgatgc aggaccaacc catggta       57
```

<210> SEQ ID NO 96
<211> LENGTH: 51
<212> TYPE: DNA
<213> ORGANISM: Artificial Sequence
<220> FEATURE:
<223> OTHER INFORMATION: synthesized primer

<400> SEQUENCE: 96

```
accgctaccg gtgttcactc cgacatccag ctgacccaga gcccaagcag c              51
```

<210> SEQ ID NO 97
<211> LENGTH: 56
<212> TYPE: DNA
<213> ORGANISM: Artificial Sequence
<220> FEATURE:
<223> OTHER INFORMATION: synthesized primer

<400> SEQUENCE: 97

```
ctgaggatcc agaaagtgca cttacgtttg atttccacct tggtcccttg gccgaa         56
```

<210> SEQ ID NO 98
<211> LENGTH: 51
<212> TYPE: DNA
<213> ORGANISM: Artificial Sequence
<220> FEATURE:
<223> OTHER INFORMATION: synthesized primer

<400> SEQUENCE: 98

```
ctctccaccg gtgtccactc cagcatcgtg atgacccaga gcccaagcag c              51
```

<210> SEQ ID NO 99
<211> LENGTH: 51
<212> TYPE: DNA
<213> ORGANISM: Artificial Sequence
<220> FEATURE:
<223> OTHER INFORMATION: synthesized primer

<400> SEQUENCE: 99

```
ctctccaccg gtgtccactc cgacatccag atgacccaga gcccaagcag c              51
```

<210> SEQ ID NO 100
<211> LENGTH: 108
<212> TYPE: PRT
<213> ORGANISM: Artificial Sequence
<220> FEATURE:
<223> OTHER INFORMATION: light chain peptide

<400> SEQUENCE: 100

```
Asp Ile Gln Met Thr Gln Ser Pro Ser Ser Leu Ser Ala Ser Val Gly
  1               5                  10                  15

Asp Arg Val Thr Ile Thr Cys Gln Ala Ser Gln Asp Ile Ile Lys Tyr
             20                  25                  30
```

```
Leu Asn Trp Tyr Gln Gln Thr Pro Gly Lys Ala Pro Lys Leu Leu Ile
            35                  40                  45

Tyr Glu Ala Ser Asn Leu Gln Ala Gly Val Pro Ser Arg Phe Ser Gly
 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Tyr Gln Ser Leu Pro Tyr
                85                  90                  95

Thr Phe Gly Gln Gly Thr Lys Leu Gln Ile Thr Arg
            100                 105
```

<210> SEQ ID NO 101
<211> LENGTH: 23
<212> TYPE: PRT
<213> ORGANISM: Artificial Sequence
<220> FEATURE:
<223> OTHER INFORMATION: light chain peptide

<400> SEQUENCE: 101

```
Asp Ile Gln Met Thr Gln Ser Pro Ser Ser Leu Ser Ala Ser Val Gly
 1               5                  10                  15

Asp Arg Val Thr Ile Thr Cys
            20
```

<210> SEQ ID NO 102
<211> LENGTH: 15
<212> TYPE: PRT
<213> ORGANISM: Artificial Sequence
<220> FEATURE:
<223> OTHER INFORMATION: light chain peptide

<400> SEQUENCE: 102

```
Trp Tyr Gln Gln Thr Pro Gly Lys Ala Pro Lys Leu Leu Ile Tyr
 1               5                  10                  15
```

<210> SEQ ID NO 103
<211> LENGTH: 32
<212> TYPE: PRT
<213> ORGANISM: Artificial Sequence
<220> FEATURE:
<223> OTHER INFORMATION: light chain peptide

<400> SEQUENCE: 103

```
Gly Val Pro Ser Arg Phe Ser Gly Ser Gly Ser Gly Thr Asp Tyr Thr
 1               5                  10                  15

Phe Thr Ile Ser Ser Leu Gln Pro Glu Asp Ile Ala Thr Tyr Tyr Cys
                20                  25                  30
```

<210> SEQ ID NO 104
<211> LENGTH: 10
<212> TYPE: PRT
<213> ORGANISM: Artificial Sequence
<220> FEATURE:
<223> OTHER INFORMATION: light chain peptide

<400> SEQUENCE: 104

```
Phe Gly Gln Gly Thr Lys Leu Gln Ile Thr
 1               5                  10
```

<210> SEQ ID NO 105
<211> LENGTH: 29
<212> TYPE: PRT
<213> ORGANISM: Artificial Sequence
<220> FEATURE:

```
<223> OTHER INFORMATION: heavy chain peptide
<220> FEATURE:
<221> NAME/KEY: VARIANT
<222> LOCATION: (1)...(29)
<223> OTHER INFORMATION: Xaa = Any Amino Acid

<400> SEQUENCE: 105

Val Gln Leu Xaa Xaa Ser Gly Pro Gly Leu Val Arg Pro Ser Gln Thr
  1               5                  10                  15

Leu Ser Leu Thr Cys Thr Val Ser Gly Ser Thr Phe Ser
             20                  25

<210> SEQ ID NO 106
<211> LENGTH: 6
<212> TYPE: PRT
<213> ORGANISM: Artificial Sequence
<220> FEATURE:
<223> OTHER INFORMATION: heavy chain peptide

<400> SEQUENCE: 106

Gln Val Gln Leu Gln Glu
  1               5

<210> SEQ ID NO 107
<211> LENGTH: 4
<212> TYPE: PRT
<213> ORGANISM: Artificial Sequence
<220> FEATURE:
<223> OTHER INFORMATION: heavy chain peptide

<400> SEQUENCE: 107

Phe Asn Ile Lys
  1

<210> SEQ ID NO 108
<211> LENGTH: 14
<212> TYPE: PRT
<213> ORGANISM: Artificial Sequence
<220> FEATURE:
<223> OTHER INFORMATION: heavy chain peptide

<400> SEQUENCE: 108

Trp Val Arg Gln Pro Pro Gly Arg Gly Leu Glu Trp Ile Gly
  1               5                  10

<210> SEQ ID NO 109
<211> LENGTH: 43
<212> TYPE: PRT
<213> ORGANISM: Artificial Sequence
<220> FEATURE:
<223> OTHER INFORMATION: heavy chain peptide

<400> SEQUENCE: 109

Arg Val Thr Met Leu Val Asp Thr Ser Lys Asn Gln Phe Ser Leu Arg
  1               5                  10                  15

Leu Ser Ser Val Thr Ala Ala Asp Thr Ala Val Tyr Tyr Cys Ala Arg
             20                  25                  30

Trp Gly Gln Gly Ser Leu Val Thr Val Ser Ser
         35                  40
```